(12) United States Patent
Zhang

(10) Patent No.: US 11,458,329 B2
(45) Date of Patent: Oct. 4, 2022

(54) COMPONENTRY AND DEVICES FOR LIGHT THERAPY DELIVERY AND METHODS RELATED THERETO

(71) Applicant: Z2020, LLC, Houston, TX (US)

(72) Inventor: Jack K. Zhang, Houston, TX (US)

(*) Notice: Subject to any disclaimer, the term of this patent is extended or adjusted under 35 U.S.C. 154(b) by 0 days.

(21) Appl. No.: 17/203,308

(22) Filed: Mar. 16, 2021

(65) Prior Publication Data

US 2021/0196977 A1 Jul. 1, 2021

Related U.S. Application Data

(63) Continuation of application No. 17/064,017, filed on Oct. 6, 2020, which is a continuation of application
(Continued)

(51) Int. Cl.
*A61N 5/06* (2006.01)
*A61N 5/067* (2006.01)

(52) U.S. Cl.
CPC ............ *A61N 5/0616* (2013.01); *A61N 5/067* (2021.08); *A61N 2005/0651* (2013.01); *A61N 2005/0659* (2013.01)

(58) Field of Classification Search
CPC ...... A61B 18/20–18/28; A61N 5/06–2005/073
(Continued)

(56) References Cited

U.S. PATENT DOCUMENTS 5,616,140 A 4/1997 Prescott
5,989,245 A 11/1999 Prescott
(Continued)

FOREIGN PATENT DOCUMENTS

EP 0627243 12/1994
GB 2532189 5/2016
(Continued)

OTHER PUBLICATIONS

Keiser, Gerd, et al. "Review of diverse optical fibers used in biomedical research and clinical practice." Journal of biomedical optics 19.8 (2014): 080902.
(Continued)

*Primary Examiner* — Jonathan T Kuo
*Assistant Examiner* — Vynn V Huh
(74) *Attorney, Agent, or Firm* — Barry Choobin; Patent 360

(57) ABSTRACT

The invention comprises componentry and devices for light therapy application to a patient in need thereof. The present invention relates to controllers for light therapy devices, light delivery elements, light guides, light guide arrangements configured to deliver personalized light therapy to one or more patients, with related componentry, dosage, and configurations of light therapy delivery elements (e.g., bandages, garments, braces, inserts etc.) suitable to deliver light therapy to one or more patient body areas and associated tissues, as well as sensors for monitoring treatment progress and dosage optimization. Methods of delivering light therapy to a patient and treatment of associated medical indications are also set out herein. Personalized LLLT dosage configurations and telemedicine LLLT treatment platforms and systems are also provided herein.

1 Claim, 44 Drawing Sheets

Related U.S. Application Data

No. 16/110,688, filed on Aug. 23, 2018, now abandoned, which is a continuation of application No. PCT/US2017/043988, filed on Jul. 26, 2017, which is a continuation-in-part of application No. 15/645,467, filed on Jul. 10, 2017, now abandoned.

(60) Provisional application No. 62/499,674, filed on Feb. 3, 2017, provisional application No. 62/499,612, filed on Jan. 31, 2017, provisional application No. 62/498,401, filed on Dec. 27, 2016, provisional application No. 62/496,714, filed on Oct. 27, 2016, provisional application No. 62/494,065, filed on Jul. 27, 2016.

(58) Field of Classification Search
USPC ................................ 606/2–19; 607/88–94
See application file for complete search history.

(56) References Cited

U.S. PATENT DOCUMENTS

| | | |
|---|---|---|
| 5,997,569 A | 12/1999 | Chen et al. |
| 6,210,425 B1 | 4/2001 | Chen |
| 6,238,426 B1 | 5/2001 | Chen |
| 6,312,451 B1 | 11/2001 | Streeter |
| 6,353,763 B1 | 3/2002 | George et al. |
| 6,454,789 B1 | 9/2002 | Chen et al. |
| 6,454,791 B1 | 9/2002 | Prescott |
| 6,494,900 B1 | 12/2002 | Salansky et al. |
| 6,848,822 B2 | 2/2005 | Ballen et al. |
| 6,986,782 B2 | 1/2006 | Chen et al. |
| 7,100,615 B1 | 9/2006 | Kert |
| 7,118,563 B2 | 10/2006 | Weckwerth et al. |
| 7,374,569 B2 | 5/2008 | Whatcott et al. |
| 7,686,839 B2 | 3/2010 | Parker |
| 7,842,075 B2 | 11/2010 | Kahn et al. |
| 7,970,624 B2 | 6/2011 | Anderson et al. |
| 8,109,981 B2 | 2/2012 | Gertner et al. |
| 8,136,531 B2 | 3/2012 | Chariff |
| 8,192,473 B2 | 6/2012 | Tucker et al. |
| 8,286,639 B2 | 10/2012 | Seckel |
| 8,308,784 B2 | 11/2012 | Streeter et al. |
| 8,351,750 B2 | 1/2013 | Fine et al. |
| 8,492,448 B2 | 7/2013 | Dewa et al. |
| 8,535,361 B2 | 9/2013 | Lim et al. |
| 8,585,707 B2 | 11/2013 | Rogers |
| 8,636,726 B1 | 1/2014 | Wells et al. |
| 8,652,061 B2 | 2/2014 | Yu et al. |
| 3,702,772 A1 | 4/2014 | Luzon et al. |
| 8,702,291 B2 | 4/2014 | Stephan |
| 8,724,942 B2 | 5/2014 | Logunov et al. |
| 8,760,295 B2 | 6/2014 | Forster |
| 8,778,002 B2 | 7/2014 | Moy |
| 8,784,462 B2 | 7/2014 | Deroberts |
| 8,805,141 B2 | 8/2014 | Fewkes et al. |
| 8,858,477 B2 | 10/2014 | Pylyp |
| 8,864,362 B2 | 10/2014 | Sherman et al. |
| 8,900,282 B2 | 12/2014 | Brawn |
| 8,912,142 B2 | 12/2014 | Sprecher et al. |
| 8,929,965 B2 | 1/2015 | Leboeuf et al. |
| 8,936,630 B2 | 1/2015 | Denison et al. |
| 8,945,196 B2 | 2/2015 | Huttemann et al. |
| 8,974,486 B2 | 3/2015 | Kotler |
| 8,989,830 B2 | 3/2015 | Leboeuf et al. |
| 9,005,101 B1 | 4/2015 | Van Erlach |
| 9,056,198 B2 | 6/2015 | Gerlitz et al. |
| 9,061,135 B1 | 6/2015 | Keller et al. |
| 9,067,061 B2 | 6/2015 | Samuel et al. |
| 9,144,690 B2 | 9/2015 | McDaniel |
| 9,153,934 B2 | 10/2015 | Takada et al. |
| 9,160,132 B2 | 10/2015 | Takada et al. |
| 9,204,805 B2 | 12/2015 | Panasyuk et al. |
| 9,215,980 B2 | 12/2015 | Tran et al. |
| 9,216,300 B2 | 12/2015 | Pryor et al. |
| 9,265,576 B2 | 2/2016 | Srinivasan |
| 9,295,854 B2 | 3/2016 | Mersch |
| 9,352,169 B2 | 5/2016 | Boo et al. |
| 9,476,637 B2 | 10/2016 | Sherman et al. |
| 9,579,521 B2 | 2/2017 | Ferraz Rigo et al. |
| 9,687,669 B2 | 6/2017 | Stephan |
| 9,724,536 B1 | 8/2017 | Rabin et al. |
| 9,737,727 B2 | 8/2017 | Unger |
| 2001/0008973 A1* | 7/2001 | Van Zuylen ......... A61N 5/0616 607/88 |
| 2002/0198576 A1 | 12/2002 | Chen et al. |
| 2003/0032900 A1 | 2/2003 | Ella |
| 2004/0073278 A1 | 4/2004 | Pachys |
| 2004/0077977 A1 | 4/2004 | Ella et al. |
| 2004/0167500 A1 | 8/2004 | Weckwerth et al. |
| 2004/0260209 A1 | 12/2004 | Ella et al. |
| 2004/0260210 A1 | 12/2004 | Ella et al. |
| 2005/0080465 A1 | 4/2005 | Zelickson et al. |
| 2005/0177093 A1 | 8/2005 | Barry et al. |
| 2005/0203592 A1 | 9/2005 | Teichert |
| 2006/0047330 A1 | 3/2006 | Whatcott et al. |
| 2006/0085223 A1 | 4/2006 | Anderson et al. |
| 2006/0089629 A1* | 4/2006 | Howe ..................... A61B 90/96 606/16 |
| 2006/0095098 A1 | 5/2006 | Shanks et al. |
| 2006/0173514 A1 | 8/2006 | Biel et al. |
| 2006/0200211 A1 | 9/2006 | Lin |
| 2006/0217787 A1 | 9/2006 | Olson et al. |
| 2006/0235346 A1 | 10/2006 | Prescott |
| 2006/0241495 A1 | 10/2006 | Kurtz |
| 2006/0257095 A1 | 11/2006 | Walt et al. |
| 2007/0021807 A1 | 1/2007 | Kurtz |
| 2007/0079838 A1 | 4/2007 | Seckel |
| 2007/0106192 A1 | 5/2007 | Johnson |
| 2007/0129776 A1 | 6/2007 | Robins et al. |
| 2007/0162092 A1 | 7/2007 | Yen |
| 2007/0208395 A1 | 9/2007 | Leclerc et al. |
| 2007/0208396 A1 | 9/2007 | Whatcott et al. |
| 2007/0233208 A1 | 10/2007 | Kurtz et al. |
| 2007/0233209 A1 | 10/2007 | Whitehurst |
| 2007/0239232 A1 | 10/2007 | Kurtz et al. |
| 2007/0255358 A1 | 11/2007 | Kahn et al. |
| 2007/0260297 A1 | 11/2007 | Chariff |
| 2007/0282401 A1 | 12/2007 | Kahn et al. |
| 2008/0096857 A1 | 4/2008 | Curaudeau et al. |
| 2008/0103563 A1 | 5/2008 | Powell et al. |
| 2008/0119913 A1 | 5/2008 | Powell et al. |
| 2008/0125836 A1* | 5/2008 | Streeter ............... A61N 5/0618 607/89 |
| 2008/0269849 A1 | 10/2008 | Lewis |
| 2009/0076844 A1 | 3/2009 | Koegen |
| 2009/0099459 A1 | 4/2009 | Svanberg et al. |
| 2009/0216300 A1 | 8/2009 | Keltner et al. |
| 2009/0254154 A1 | 10/2009 | De Taboada et al. |
| 2009/0319008 A1 | 12/2009 | Mayer |
| 2010/0056982 A1 | 3/2010 | Curaudeau et al. |
| 2010/0106077 A1* | 4/2010 | Rabin ................... A61N 5/0616 604/20 |
| 2010/0121419 A1 | 5/2010 | Douglas |
| 2010/0160904 A1 | 6/2010 | McMillan et al. |
| 2010/0242155 A1 | 9/2010 | Carullo, Jr. |
| 2010/0318161 A1 | 12/2010 | Brawn |
| 2010/0324632 A1 | 12/2010 | Lim et al. |
| 2011/0040355 A1 | 2/2011 | Francis |
| 2011/0066213 A1 | 3/2011 | Huttemann et al. |
| 2011/0087312 A1 | 4/2011 | Shanks et al. |
| 2011/0112613 A1 | 5/2011 | Gerlitz et al. |
| 2011/0143286 A1 | 6/2011 | Takada et al. |
| 2011/0176325 A1 | 7/2011 | Sherman et al. |
| 2011/0176326 A1 | 7/2011 | Stephan |
| 2011/0206752 A1 | 8/2011 | Carreno Serraima et al. |
| 2011/0212411 A1 | 9/2011 | Sinofsky |
| 2011/0218595 A1 | 9/2011 | McMillan |
| 2011/0245898 A1 | 10/2011 | Takada et al. |
| 2011/0270092 A1 | 11/2011 | Kang et al. |
| 2011/0301673 A1 | 12/2011 | Hoffer et al. |
| 2012/0116274 A1 | 5/2012 | Grasso, IV |
| 2012/0116485 A1 | 5/2012 | Burgmann |
| 2012/0148975 A1 | 6/2012 | Brawn |

(56) References Cited

U.S. PATENT DOCUMENTS

| | | |
|---|---|---|
| 2012/0215120 A1 | 8/2012 | Yu et al. |
| 2012/0275178 A1 | 11/2012 | Logunov et al. |
| 2012/0275180 A1 | 11/2012 | Button et al. |
| 2012/0319010 A1 | 12/2012 | Bornstein et al. |
| 2013/0018442 A1 | 1/2013 | Irwin |
| 2013/0041431 A1 | 2/2013 | Gerlitz et al. |
| 2013/0057828 A1 | 3/2013 | De Smet |
| 2013/0083185 A1 | 4/2013 | Coleman, III |
| 2013/0116612 A1* | 5/2013 | Stephan ............... A61F 13/107 602/43 |
| 2013/0144278 A1 | 6/2013 | Papac et al. |
| 2013/0165912 A1 | 6/2013 | Jay |
| 2013/0289670 A1 | 10/2013 | Thiberg et al. |
| 2014/0074193 A1 | 3/2014 | Luzon et al. |
| 2014/0092623 A1 | 4/2014 | Logunov et al. |
| 2014/0105834 A1 | 4/2014 | Seckel |
| 2014/0107493 A1 | 4/2014 | Yuen et al. |
| 2014/0135874 A1 | 5/2014 | Dean et al. |
| 2014/0198520 A1 | 7/2014 | Bennett et al. |
| 2014/0243612 A1 | 8/2014 | Li et al. |
| 2014/0330351 A1 | 11/2014 | Jay |
| 2014/0355295 A1 | 12/2014 | Kuchinisky et al. |
| 2015/0009704 A1 | 1/2015 | Knight et al. |
| 2015/0045843 A1 | 2/2015 | Asah |
| 2015/0104141 A1 | 4/2015 | Logunov et al. |
| 2015/0133832 A1 | 5/2015 | Courtion et al. |
| 2015/0147229 A1 | 5/2015 | Fewkes et al. |
| 2015/0290470 A1 | 10/2015 | Tapper et al. |
| 2015/0297914 A1 | 10/2015 | Hamid et al. |
| 2015/0335905 A1 | 11/2015 | Bonizzoni |
| 2016/0008628 A1 | 1/2016 | Morries et al. |
| 2016/0010833 A1 | 1/2016 | Fewkes et al. |
| 2016/0038762 A1 | 2/2016 | Lin |
| 2016/0059034 A1 | 3/2016 | Klang |
| 2016/0103261 A1 | 4/2016 | Bauco et al. |
| 2016/0106999 A1* | 4/2016 | Michaels .............. A61M 37/00 604/20 |
| 2016/0113941 A1 | 4/2016 | Berns et al. |
| 2016/0129279 A1 | 5/2016 | Ferolito |
| 2016/0263395 A1 | 9/2016 | Siegel et al. |
| 2016/0335910 A1 | 11/2016 | Baumann |
| 2017/0014640 A1 | 1/2017 | Kariguddaiah |
| 2017/0028213 A1 | 2/2017 | Courtion et al. |
| 2017/0095398 A1 | 4/2017 | Courtion et al. |
| 2017/0106206 A1 | 4/2017 | Seckel |
| 2017/0216617 A1 | 8/2017 | Kariguddaiah |
| 2017/0319870 A1 | 11/2017 | Liebert et al. |

FOREIGN PATENT DOCUMENTS

| | | |
|---|---|---|
| WO | 2000041768 | 7/2000 |
| WO | 2010026422 | 3/2010 |
| WO | 2011051467 | 5/2011 |

OTHER PUBLICATIONS

Cotler, Howard B., et al. "The use of low level laser therapy (LLLT) for musculoskeletal pain." MOJ orthopedics & rheumatology 2.5 (2015).

Molding for Medical Silicone LED Lighting Devices, (n.d.). Retrieved from https://albrightsilicone.com/molding-for-medical-silicone-led-lighting-devices/.

Kalleit, David; et al. "Wearable Light Management System for Light Stimulated Healing of Large Area Chronic Wounds." SPIE Photonics West (2016). http://www.medilight-project.eu/wp-content/uploads/2016/02/PW2016_RFi_20160213.pdf.

Philips Bluetouch Pain Relief Patch (Nov. 2015) Weblink: https://www.download.p4c.philips.com/files/p/pr3092_00/or3092_00_pss_.pdf.

Manessis D. "MEDILIGHT: Miniaturized smart system for light stimulation and monitoring of wound healing" Technical University Berlin. (Oct. 2015) Technology Translation into Usable & Marketable Systems & Services Session.

\* cited by examiner

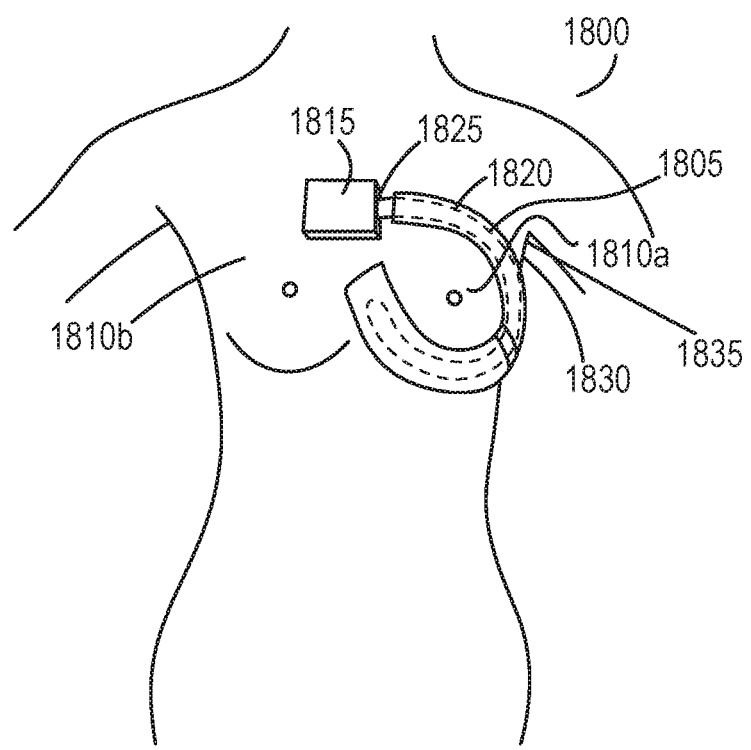
FIG. 18A
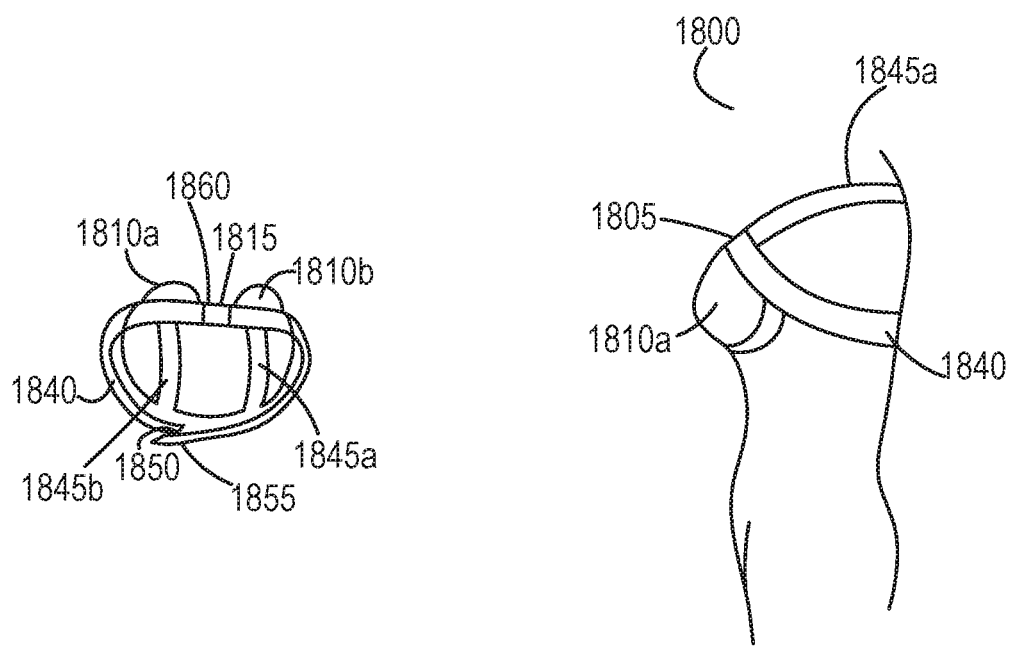
FIG. 18B
FIG. 18C

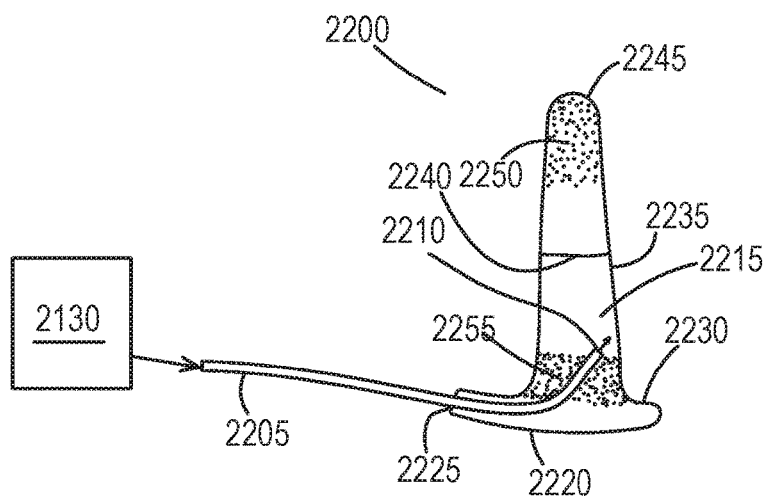
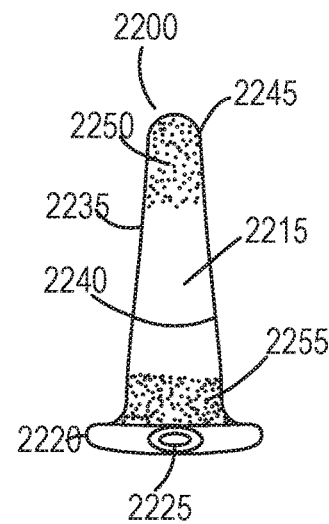
FIG. 22A  FIG. 22B
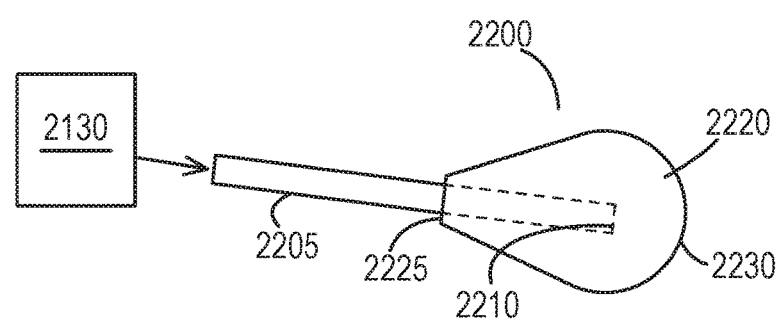
FIG. 22C

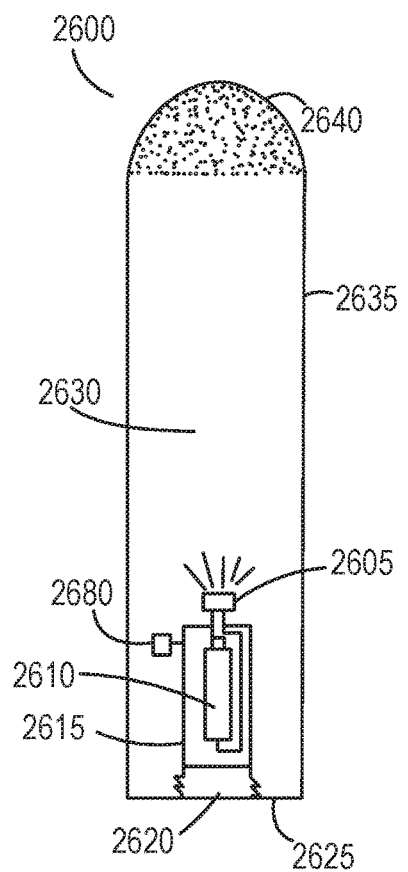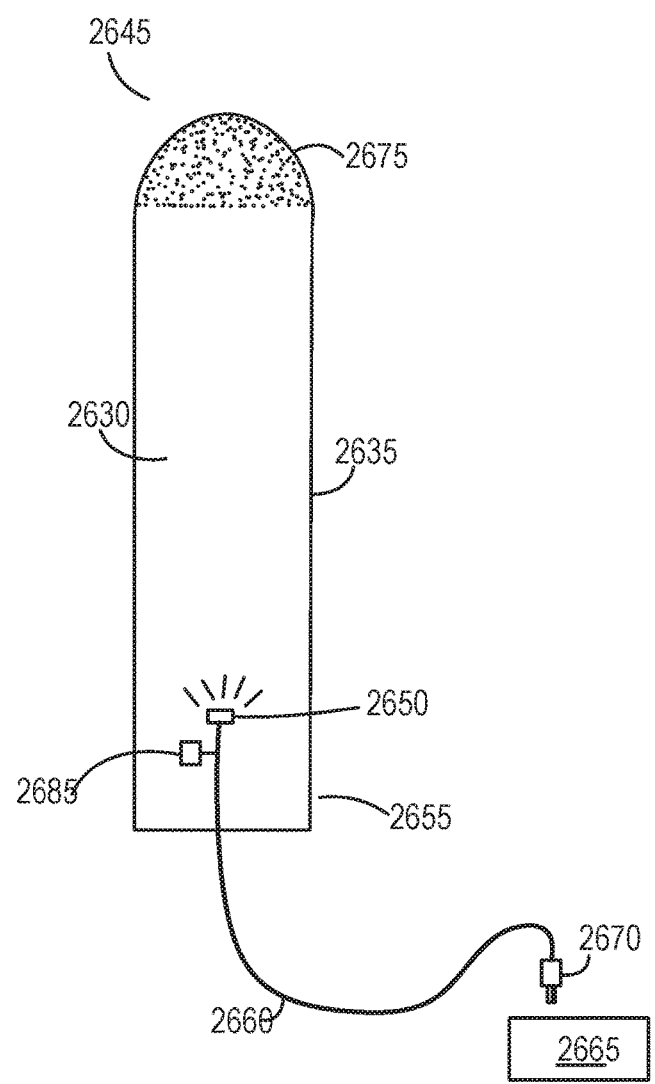
FIG. 26A
FIG. 26B

COMPONENTRY AND DEVICES FOR LIGHT THERAPY DELIVERY AND METHODS RELATED THERETO

CROSS REFERENCE TO RELATED APPLICATIONS

This application is a continuation of co-pending U.S. application Ser. No. 17/064,017, filed Oct. 6, 2020, which claims priority to, and the benefit of, U.S. Utility application Ser. No. 16/110,688, filed Aug. 23, 2018, which claims priority to, and the benefit of, PCT Application No. PCT/US/2017/043988 (hereafter "the PCT '988 application"), filed Jul. 26, 2017, which is hereby incorporated by reference in its entirety. The PCT '988 application claims priority to US Provisional Patent Application Nos. 62/494,065 filed on Jul. 27, 2016; 62/496,714 filed on Oct. 27, 2016; 62/498,401 filed on Dec. 27, 2016, 62/499,612 filed on Jan. 31, 2017; and 62/499,674 filed on Feb. 3, 2017. The PCT '988 application also claims priority to U.S. Utility application Ser. No. 15/645,467, filed Jul. 10, 2017. The disclosures of each of these applications are incorporated herein in their entireties by this reference. All references cited herein are incorporated by reference.

FIELD OF THE INVENTION

The invention comprises componentry and devices for light therapy application to a patient in need thereof. The present invention relates to control modules for light therapy devices, light guides, and light guide arrangements configured to deliver light therapy to one or more areas on a patient, related componentry. Yet further, the invention relates to configurations of light therapy delivery elements (e.g., bandages, garments, blankets, braces, inserts etc.) suitable to deliver therapeutic amounts of light therapy to one or more patient areas and associated tissues. Methods and systems for delivering light therapy to a patient and treatment of associated medical indications are also set out herein. Personalized LLLT dosage configurations and telemedicine LLLT treatment platforms and systems are also provided herein.

BACKGROUND OF THE INVENTION

Low level light therapy ("LLLT") relates, in some aspects, to the exposing of cells or tissue to low levels of red and near infrared ("NIR") light. When the applied light is laser sourced, LLLT is also known as "low level laser" or "cold laser" therapy, as the power densities used are lower than those needed to produce heating of tissue. In this regard, light application is at relatively low energy densities, typically below about 500 mW, as compared to other forms of laser therapy that are used for ablation, cutting, and thermally coagulating tissue. Other types of LLLT can also apply wavelengths in the blue or ultraviolet regions, especially for treatment of conditions that occur at the skin surface, such as psoriasis or infection. While it was originally believed that effective LLLT required the use of coherent laser light, more recently, light emitting diodes ("LEDs") have been introduced as an alternative light source. Today, the term "low level light therapy" refers to light generated from both laser and LED sources. Super luminous diodes ("SLD") have also found some application in LLLT treatments.

Irrespective of the type of light source utilized, at the most basic level, LLLT is believed to affect a biological change in living tissue by inducing a photochemical reaction in the cell, a process referred to medically as "photobiomodulation" or "PBM." From clinical observation, it appears that LLLT can hold a wide range of effects at the molecular, cellular, and tissue levels. In addition, the specific modes of action can vary among different applications. As reported in "Effects of Low-Power Light Therapy on Wound Healing: Laser LED, *An Bras. Dermatol.* 2014; 89(4): 616-23, the disclosure of which is incorporated in its entirety by this reference, the biological effects of LLLT appear to be largely dependent on the treatment parameters of applied light wavelength(s) and dosage(s). While wavelengths of light and dosage parameters specifically defined for an experimental condition have been elucidated by way of many studies described in this referenced review article, the authors indicate that what constitutes a therapeutic dose across medical indications, patients, and the like remains largely unresolved.

Although LLTT has been recognized to be efficacious to treat a wide variety of indications, LLLT nonetheless remains underutilized as a therapy for several reasons. First, since the underlying biochemical mechanisms are poorly understood today, many use cases remain anecdotal and reported results are largely empirical in nature. Accordingly, for applications where clinical efficacy must be demonstrated, LLLT will generally not be prescribed by a medical healthcare provider. Next, for LLLT to be properly applied to a patient in need of treatment, several variables must be selected and repeatedly monitored throughout the course of the treatment. These parameters include wavelength, energy density, power density, pulse structure, and timing of the applied light, as well as the patient medical indication and any associated patient-specific parameters. Each of these features can contribute to the effectiveness of an applied LLLT treatment. A less than optimal choice of parameters can result in reduced effectiveness of the treatment, or even adverse therapeutic outcomes. The multiplicity of treatment variables that can affect LLLT treatment effectiveness likely contributes to the dearth of unambiguous and repeatable results that allow a LLLT treatment to be prescribed regularly in clinical settings. Indeed, many of the published results on LLLT treatments actually demonstrate negative clinical efficacy, possibly because of an inappropriate choice of light source and dosage for the patients being treated.

There is also evidence to suggest that the effectiveness of the treatment varies greatly in relation to both the energy and power density used: there appears to be upper and lower thresholds for both parameters within which LLLT is effective. Outside of these thresholds, the light is either too weak to have any effect, or is so strong that its harmful effects outweigh its benefits. For example, it has been reported that too low of a dose does not promote biological effects, and doses that are too high result in the inhibition of cellular functions. LLLT can therefore be characterized by a biphasic dose response that indicates a range within which beneficial effects can be generated with light application. Notwithstanding this knowledge, to date, there has been no meaningful resolution of dosage parameters for specific medical indications.

Delivery systems associated with LLLT treatment have not lent themselves to well-defined dose application of LLLT to a patient in need of treatment. Lasers have typically been difficult to implement outside of the clinical setting due to need to generate and reliably deliver an effective dose of laser light to a patient. Moreover, the periodic and longitudinal nature of LLLT treatment has made it generally infeasible to treat people cost effectively. Until recently, lasers and the associated componentry have been expensive and have required mains power to generate suitable energy to power the componentry. In addition, most LLLT treatment modalities would require people to travel regularly to a medical provider's office or a hospital and stay for and return to enough times to affect a full course of LLLT treatment that would result in the intended therapeutic outcome.

A number of wearable or home treatment LLLT treatment devices have been proposed to better effect patient treatment over an extended period in an attempt to reduce the historically high cost or time constraints. These devices and associated methods are disclosed in, for example, U.S. Pat. Nos. 5,616,140, 6,986,782, 7,102,615, 8,399,731, 8,702,291, 8,784,462, 9,067,061, 9,295,854, and 9,687,669 and US Patent Publication Nos. 20060173514, 20070208395, 20070208396, 20120116274, 20140135874, 20150148734, 20150290470, and 2017001464, and UK Patent Application No. GB 2532189, the disclosures of which are incorporated herein in their entireties by this reference. Notwithstanding these myriad of proposed LLLT treatment implementations, which include both "cold laser" and LED light sources, wearable LLLT treatment devices have not been widely introduced for use by patients for treatments of pain, wounds, and other forms of therapeutic activity.

One commercially available LLLT treatment device sold under the name LaserWRAP® appears from a website representation (http://(wearablelaserwrap.com/TheLASER-wrapAdvantage/LaserTherapy retrieved May 17, 2017) similar to that disclosed in U.S. Pat. No. 9,687,669, previously incorporated by reference. As shown in the '669 Patent, the device utilizes a polymeric light guide that appears to be in operational engagement with a laser, control module and battery. The '669 Patent device appears to be configured to function much like a wearable, battery powered heating pad or TENS device. To this end, each example of the device use is directed toward general body areas, as opposed to specific medical indications that would give rise to a patient's area or body part needing to be treated in the first place. The laser light is distributed along the interior length of the illustrated devices therein. It follows that delivery of a therapeutic dosage would only be incidental to use of the devices disclosed therein. The '669 Patent provides no disclosure of an interface for a user to provide feedback other than a power switch. The device therefore can only apply a set dose that is generally defined irrespective of a specific patient. Moreover, there is no remote communications capability incorporated into the Laser-WRAP device nor are there any sensor means to collect data for treatment compliance, progress or dosage effectiveness monitoring. As a result, there is no way for a provider to monitor patient usage and treatment progress after the LLLT treatment starts, nor is there any way for the provider to manage, such as by modifying the dosage during a longitudinal treatment that occurs outside of a healthcare facility. There also is no way to collect data during the treatment regimen related to the progression of treatment. As such, the LLLT treatment device configuration of the '669 Patent and the referenced website description of a similar device should be considered "universal" or "generic" LLLT treatment device design that does not address selection of a specific medical indication, nor does it contemplate definition of specific dosage parameters for the selected indication and a specific patient or patient population.

There remains a need for improvements in LLLT treatment devices and methods for the treatment of pain, wounds and other medical indications. There also remains a need for improvements in the systems and methods in which LLLT is delivered to patients in need of treatment thereof. Still further, there is a need for improvements in the definition of suitable dosing of LLLT in patients in need of such treatment. Still further, improvements are needed in the management of dosing of LLLT during treatment of a patient, and in providing subsequent treatments for that patient, as well as a population of patients. The present invention provides this and other benefits.

SUMMARY OF THE INVENTION

In broad constructs, the invention comprises componentry and devices for LLLT application to a patient in need thereof. In significant aspects, the devices of the present invention are wearable by a patient in need of treatment or the devices are otherwise highly portable. The present invention relates to controller modules for light therapy devices, light guides, light guide arrangements, and light delivery componentry configured to deliver light therapy to one or more areas on a patient, related componentry, and configurations of light therapy delivery elements (e.g., bandages, garments, braces, inserts etc.) suitable to deliver light therapy to one or patient areas and tissues. Methods of delivering light therapy to a patient and the treatment of associated medical indications are also set out herein.

In some aspects, the inventions relate to a control module for application of LLLT to a patient in need of treatment, the control module comprising: a microprocessor, at least one light source, wherein the at least one light source is configurable to generate light in one or more wavelengths of from about 200 nm to about 1000 nm (or other wavelengths or wavelength ranges appropriate to effect LLLT treatment in a patient in need of treatment), a power source configured to provide power to the control module, a memory module, a communications module, at least one engagement port configured to provide engagement of a single light delivery element with the at least one light source, wherein the light delivery element is configured to deliver LLLT generated from the at least one light source directly or indirectly to one or more areas on a patient in need of treatment with LLLT, and a housing or containment structure configured to contain each of these components. To enhance wearability or portability, the LLLT device is powered by a battery. The control module can comprise one or a plurality of light sources configured to deliver LLLT in one or more desired wavelengths to a patient in need of treatment. The LLLT treatment device can further be configured to collect light emitted from a patient's wound or treatment area for collection in one or more sensors associated with the LLLT devices that can provide information about the effectiveness of a LLLT treatment.

In further aspects, the control module is configured to store and/or deliver a LLLT prescription for a patient, whereby that prescription is suitable to provide a therapeutic amount of LLLT to the patient over individual treatment periods or throughout an overall treatment regimen. The control module can be configured to store or transfer LLLT dosage information from a device or remote server associated with a provider prior to or during a LLLT treatment delivered to the patient.

Appropriate matching of a patient with a prescribed LLLT treatment and LLLT treatment device can be facilitated by incorporation of functionality that validates a LLLT delivery element associated with light guide element(s) as being authorized for use by a patient. If the validation is not successfully completed, LLLT treatment can be prevented from being delivered to the patient. The control module can also comprise validation functionality, such as requiring a user to input an authorization code prior to the control module being activated.

The LLLT componentry, devices, and methods herein have applicability to a wide variety of medical and cosmetic indications. Device configurations such as bandages, garments, braces, wraps, and body cavity inserts can be configured using the inventions herein. Such devices and methods can have applicability to treating acute wound conditions resulting from surgeries, accidents or the like. Chronic wounds are also treatable with the devices and methods herein. Surface, body cavity, internal, mucosal, subcutaneous and other body areas are treatable with the inventions herein. Human and animal patients are treatable.

The LLLT componentry, devices and methods herein have utility in enhancing the time required for wound healing, as well as demonstrating reduction in the amount of swelling and pain in patients exhibiting a variety of medical indications. Disinfection of wounds to reduce infections is also possible with the inventions herein.

Personalized LLLT dosage configurations and telemedicine LLLT treatment platforms and systems are also provided herein.

Additional advantages of the invention will be set forth in part in the description that follows, and in part will be apparent from the description, or may be learned by practice of the invention. The advantages of the invention will be realized and attained by means of the elements and combination particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIGS. 18A-18C illustrate a LLLT device for treatment of a breast area.

FIGS. 22A-22C illustrate different views and componentry associated with an insertable vaginal light therapy device.

FIGS. 26A-26B illustrate alternative implementations of insertable vaginal light delivery devices.

DETAILED DESCRIPTION OF THE INVENTION

Figure 1:
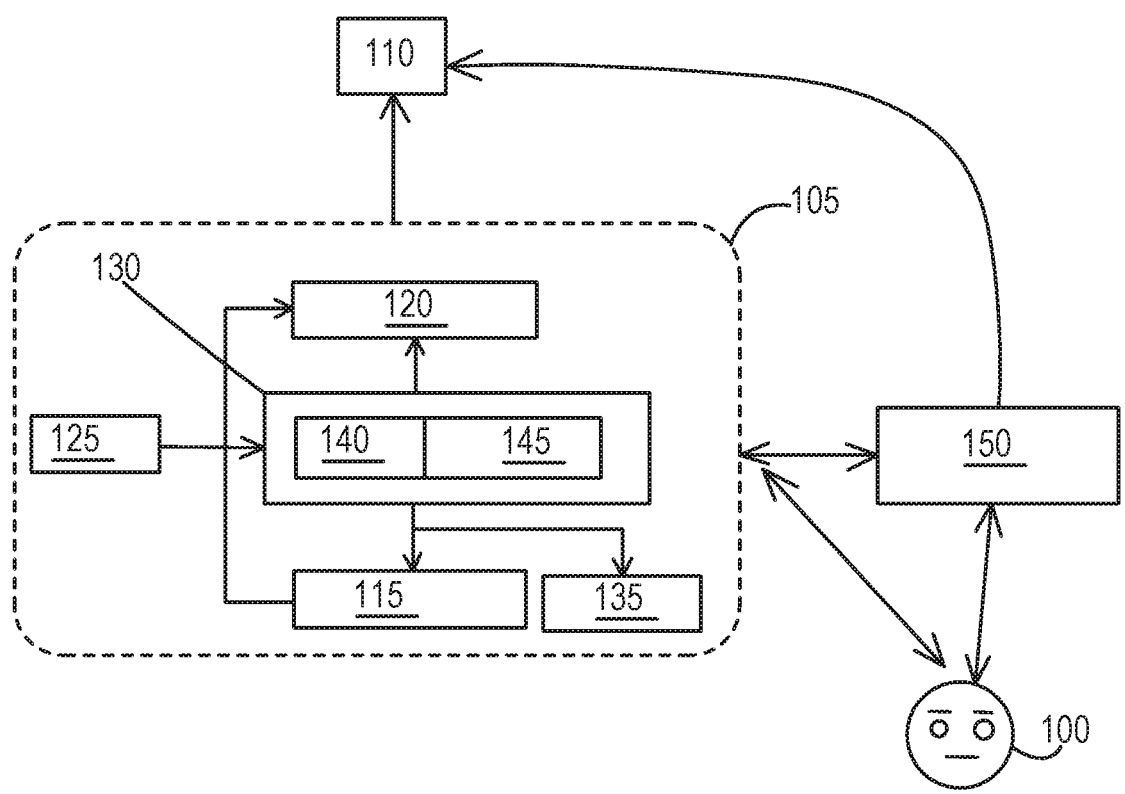
FIG. 1 illustrates an implementation of the present invention whereby LLLT treatment is delivered to a patient.

In the following detailed description, reference is made to the accompanying drawings, which form a part hereof, and within which are shown by way of illustration certain embodiments by which the subject matter of this disclosure may be practiced. It is to be understood that other embodiments may be utilized and structural changes may be made without departing from the scope of the disclosure. In other words, illustrative embodiments and aspects are described below. But it will of course be appreciated that in the development of any such actual embodiment, numerous implementation-specific decisions must be made to achieve the developers' specific goals, such as compliance with system-related and business-related constraints, which may vary from one implementation to another. Moreover, it will be appreciated that such development effort might be somewhat complex and time-consuming, but would nevertheless be a routine undertaking for those of ordinary skill in the art having the benefit of this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common patent law definition of "comprising" and is therefore interpreted to be an open term meaning "at least the following" and is also interpreted not to exclude additional features, limitations, aspects, etc.

The term "about" is meant to account for variations due to experimental error. All measurements or numbers are implicitly understood to be modified by the word "about," even if the measurement or number is not explicitly modified by the word "about."

The term "substantially" (or alternatively "effectively") is meant to permit deviations from the descriptive term that do not negatively impact the intended purpose. Descriptive terms are implicitly understood to be modified by the word "substantially," even if the term is not explicitly modified by the word "substantially."

As used herein, "low level light therapy" ("LLLT") is the use of light comprising a plurality of application parameters, such as emitted wavelength(s), pulse frequencies, duty cycle/pulse width, intensity, individual treatment duration, total treatment duration, number of individual treatments during a total treatment regimen, time between individual treatments in a total treatment regimen, first LLLT administration time from an event (such as a surgery), time-course dosage, maintenance treatments, with the goal of optimal treatment, management, and/or cure of wounds or delay/reverse tissue degeneration at one or more locations on a patient in need of such treatment, management, or cure. Both humans and animals can comprise patients that can be treated according to the inventions herein.

"LLLT" as provided herein includes light generated by "low power" lasers (or "cold lasers") and that generated by LED, SLDs, or a combination thereof. Laser light, LED, and SLD light having therapeutic effects can be generated in a variety of wavelengths or wavelength ranges suitable for use in the inventions herein.

A "laser" is a device that emits light through a process of optical amplification based on the stimulated emission of photons. As would be recognized, the term "laser" originated as an acronym for light amplification by stimulated emission of radiation. The emitted laser light is notable for its high degree of spatial and temporal coherence. Lasers are classified as Class 1, Class 2, Class 3, and Class 4 by the American National Standards Institute. Such classifications are detailed in publication ANSI 7136.1-2000, the disclosure of which is incorporated herein in its entirety by this reference. The present invention utilizes Class 1, 2 and 3 lasers as light sources for LLLT.

A "light-emitting diode" (LED) comprises a two-lead semiconductor light source that is a p-n junction diode that emits light when activated. When a suitable voltage is applied to the leads, electrons are able to recombine with electron holes within the device, releasing energy in the form of photons. This effect is called "electroluminescence," and the color of the light (corresponding to the energy of the photon) is determined by the energy band gap of the semiconductor. LEDs are typically small and integrated optical components may be used to shape the light emitting pattern. LEDs can be provided that emit various wavelengths and intensities of light, thus making them suitable for the inventive light therapies herein. More detail about wavelengths suitable for use in the present invention is disclosed hereinafter. They emit a beam of light that is non-collimated (less focused) and non-coherent. LEDs have lower power levels (mW) than laser diodes. The LED depth of penetration (up to several mm) makes them suited for the treatment of very superficial tissue.

Super luminous diodes ("SLD") emit a beam of light that is fairly monochromatic and moderately collimated. However, the SLD can not be referred to as a laser because it does not comprise coherent light, which is a key parameter of laser light. An SLD light beam is less focused than the laser diode, but more focused than the LED. Super luminous diodes typically have lower power levels (mW) than laser diodes. The SLD depth of penetration (up to 1 cm) is less than the laser diode, but greater than what is typically seen with LED.

Light guides suitable for use herein can be fabricated from moldable optical silicone resins, such as those made by Krayden® (Dow Corning, Corning N.Y.). Suitable flexible light guides can also be fabricated from polyurethane, as set out in U.S. Pat. No. 7,433,565, the disclosure of which is incorporated herein in its entirety by this reference. Flexible light guides can also be made of clear TPE (thermoplastic elastomer) such as TPX™ Polymethylpentene (PMP) from Mitsui Chemicals America. Materials suitable for use as light guides can be molded into lengths appropriate for various LLLT treatment devices of the present invention using known methods.

Yet further, light guides suitable for delivering LLLT to an area of a patient in need of treatment can comprise light emitting fiber optic fibers having side diffusion features, as disclosed, for example, in US Patent Publication No. 20150148734, the disclosure of which is incorporated herein in their entireties. Suitable side diffusing fiber optics are sold, for example, by Corning (Corning, N.Y.) under the trade name Fibrance®.

In some configurations, as set out in more detail hereinafter, both polymeric light guides or side diffusing fiber optics and non-side diffusing fiber optics—that is, conventional fiber optic cables used to transmit light with substantially no loss along the light transmission path—can be used in one or more implementations. In this regard, fiber optics can be utilized to deliver light from a PBM control module substantially without loss or transmission of light prior to delivery of such light to engagement with a light guide or light guide arrangement that is configurable to deliver LLLT proximally to the area on a patient being treated. The fiber optic light transmission element, which can comprise a first light transmission portion when directly engaged with the control module, can be engageable with at least one polymeric light guide element or side diffusing fiber optic element that is arranged deliver light proximally to one or more patient areas. The at least one light guide or side diffusing fiber optic element is a "second light transmission portion" when not directly engaged with a control module but, rather, is engaged indirectly with the control module via a first light transmission portion. In other aspects, a first light transmission portion can be comprised from a polymeric light guide, as long as the length of polymeric light guide that is not intended to deliver LLLT to an area of the patient is configurable to substantially not transmit light from the surface thereof, such as being coated etc.

A "light guide arrangement" can comprise one or more polymeric light guides or side diffusing fiber optic light delivery elements operationally and optically engageable with a control module (as such componentry is defined herein), where such light guide arrangement is configurable to deliver LLLT to a patient in need of treatment when the arrangement is associated with a LLLT delivery element.

Various wound definitions can be used herein. As described in US Patent Application No. 20070239232, the disclosure of which is incorporated herein in its entirety, wounds can be characterized in various ways. For example, "acute wounds" are those that heal normally within a few weeks, while chronic wounds are those that linger for months or even years.

Wounds can also be characterized by the stage of healing and the functional parameters therewith. The line of closure fills with clotted blood (hemostasis), and, following the progression, in order, of inflammation, proliferation and maturation. For non-chronic wounds, the wound typically heals within a few weeks. Wounds that heal by secondary union (or secondary intention) typically involve large tissue defects, with more inflammation and granulation. Granulated tissue is needed to close the defect, and is gradually transformed into stable scar tissue. Such wounds are typically large open wounds as can occur from trauma, burns, and pressure ulcers. While surgical wounds are typically stitched, or stapled shut, which reduces the burden on the wound closing functionality, a subsequent infection or wound geometry can result in granulation occurring. While such a wound may require a prolonged healing time, but will not necessarily be chronic.

Mucosal healing, such as in a vaginal cavity or nasal cavity, is mechanistically similar to that for the skin. However, associated scarring and wound closure rates are different in mucosal healing, possibly due to differences in apoptosis. If granulated tissue is torn or otherwise damaged during the healing process, bleeding can result.

In a "chronic wound," normal healing is not occurring, with progress stalled in one or more of the phases of healing. A variety of factors, including age, poor health and nutrition, diabetes, incontinence, immune deficiency problems, poor circulation, and infection can all cause a wound to become chronic. Typical chronic wounds include pressure ulcers, friction ulcers, and venous stasis ulcers. Stage 3 and Stage 4 pressure ulcers are open wounds that can occur whenever prolonged pressure is applied to skin and tissues covering bony outcrops of the body. Chronic wounds are also categorized, according to the National Pressure Ulcer Advisory Panel (NPUAP) relative to the extent of the damage.

In broad constructs, the present invention comprises devices and methods to treat, manage, and/or cure a patient in need of such treatment using LLLT. The indications for which the patient can be in need of treatment for can include one or more of open wounds, closed wounds, or chronic wounds. Such wounds can be intentionally created (e.g., by way of a surgery etc.), accidentally caused, or chronic in nature.

In a significant aspect, the LLLT treatment devices of the present invention are configured to be wearable by a patient on a specific part of the body in need of treatment, and the LLLT can be applied with such devices over an extended period. Such wearability has been found by the inventors herein to enhance the efficacy of LLLT in a patient in need of treatment over prior delivery methods, when such LLLT is applied in conjunction with one or more treatment parameters described herein.

Moreover, the inventions herein enable application of a set of defined LLLT dosages over an extended period as applied by a wearable device, where the dosage is defined in relation to the medical condition/indication for which the patient is being treated. In some aspects, the inventions relate to selection of one or more patient medical indications in need of treatment. The methods and devices herein can also incorporate patient specific information into the definition and delivery of dosage to the patient. The inventions herein can therefore also relate to identification of one or more patient-specific parameters, whereby information associated with such patient-specific parameters is incorporated into a patient LLLT treatment regimen. Patient feedback and compliance information can be generated for incorporation into the treatment regimen. The devices and methods herein can also allow LLLT treatment protocol to be readily and timely monitored by a healthcare provider and, if applicable, modified during a treatment regimen, thereby enhancing patient outcomes.

Yet further, the devices and methods of the present invention can provide enhanced information about the course and effects of a LLLT treatment program in a single patient, and among a plurality of patients, thereby improving the ability to manage LLLT in a single patient or in a population of patients by use of data associated with medical indication, dosage, treatment compliance, progress, outcome, physiological conditions, among other information. Therefore, in some aspects, the inventions herein relate to the generation of information associated with an applied LLLT treatment or program from the patient who is undergoing treatment for one or more medical indications suitable for treatment with LLLT, and incorporation of at least some of that patient generated information into a subsequent treatment for that patient, for another patient or for a group of patients.

The inventive LLLT treatment devices comprise at least one low level light source in operational engagement with at least one light guide configured to deliver a therapeutic amount of LLLT substantially proximal to a wound in need of treatment and, optionally, any areas associated with healing of the wound. Such substantially proximal LLLT delivery is provided by incorporating the at least one light guide or light guide arrangement on or among a LLLT delivery element, as such terms are described in more detail herein.

The control modules suitable for use in the present invention are referred to as "photobiomodulation ("BM") control modules," which is a convenient framework for referring to the LLLT componentry suitable to provide operation of the treatment devices of the present invention. PBM control modules suitable for use in the devices and methods of the present invention can comprise at least one light source suitable to generate a therapeutic amount of LLLT to a patient in need of treatment, at least one data communications module, at least one memory module, at least one light guide engagement port, and at least one battery power source. Operational engagement between and among these various components is provided by a controller associated with the PBM control module. Further description of the functionality of the inventive PBM control modules in described hereinafter. As discussed elsewhere herein, one or more sensors suitable to measure conditions of the patient or elsewhere can also be in operational engagement with the PBM control module.

The PBM control module can be configured in as one or more physical enclosures, such as a housing, in which each of the components are incorporated. Alternatively, the various components of the PBM control module can be distributed in a band or strip of fabric or plastic envelope or the like to provide a containment structure. Therefore, as used herein, "PBM control module" is intended to mean the operational features of the individual components associated with this aspect of the LLLT treatment devices, not just a specific format or configuration in which the operational components can be arranged in a LLLT treatment device. The components in the PBM control module should be configurable to substantially prevent moisture from contacting the internal operational components. The PBM control module can be configurable to substantially enclose electrical connections and power functionality to substantially prevent such connections and functionality from contacting the skin or tissues of the patient being treated with the LLLT treatment device. Yet further, the components should be protectable from contamination, especially if the PBM control module is intended for re-use. In further aspects, the PBM control module may be configured for use in a single LLLT treatment for some medical applications.

Regardless of whether the various aspects of the PBM control module are configured in the form of a housing or containment structure, at least one light guide engagement port is in operational communication with the at least one light source in the PBM control module. Each of the light guide engagement ports associated with a PBM control module are configurable to allow the light source(s) to be in operational and optical engagement with an associated light guide or light guide arrangement, where each of the light guides or light guide arrangements are configurable to distribute a therapeutic dosage of LLLT treatment to a patient in need of such treatment when the patient is associated with the LLLT treatment device associated therewith.

In one aspect, each of the at least one engagement port can each, independently, be configurable to deactivate or close off each of the at least one light sources when there is no associated light guide or light guide arrangement engaged with a port. This can better ensure that battery power is not expended inadvertently by the LLLT treatment device being turned on when therapeutic use is not intended. The device can also be configured to deactivate substantially all electrical functions when one or more of the light guides or all or part of the light guide arrangement(s) are not engaged an associated engagement port. Yet further, deactivation of the at least one light source when light guides or light guide arrangements are not engaged with the engagement port(s) can better ensure that harmful light, for example, laser light over class 1 is substantially prevented from contacting a person's eyes.

A wide variety of light guide and light guide arrangement configurations are suitable for use in the present invention, as long as such are configurable to dispense a desired therapeutic light therapy dosage in the inventive devices and methods described herein. Application of appropriate therapeutic dosages has been found by the inventor herein to be enhanced by the ability to configure the LLLT treatment devices to provide an optimal amount of LLLT proximal to the area of the patient in need of treatment. In this regard, it has been found to be significantly more beneficial to use light guides or light guide arrangements that are purposefully designed to be conformable to the specific body area in need of treatment for better dosage delivery, wearability, compliance and outcome.

For example, with a total knee replacement ("TKA"), the patient's incision with Standard Medial Parapatellar Approach will be generally in a "I" shape over patella (also known as the kneecap). The surgically "internally wounded areas" inside the knee are more extensive. In order to provide an effective dose—that is, a therapeutic dose in a patient having a TKA—the LLLT should at least be applied to the entire area substantially proximal to the incision and "internally wounded areas" in need of healing.

The inventor herein has determined that light guide or light guide arrangements configured to enable LLLT treatment to be applied proximally to both the external incision and the associated internally wounded areas can enhance the effectiveness of LLLT therapies. Moreover, it has been found that some LLLT delivery configurations that do not conform to allow LLLT to be applied proximally to each of the incision areas and associated "healing vital areas" can be even harmful when treating a patient post-surgically or for other wound healing in some situations.

Using TKA as an example, first, use of a non-conformable LLLT delivery configuration may not allow the therapeutic light to be suitably placed proximally to the incision and "internally wounded areas" or "healing vital areas," that is, the areas that are affected by the surgical treatment, such as associated lymph areas and circulation areas. Second, the non-specific dosage deliverable from a "generic" LLLT delivery device will be unlikely to be effective to treat TKA in a specific patient having unique physical and medical characteristics. Third, a light guide that is not configured appropriately for a TKA patient could interfere with the required function of the part of the body requiring treatment. For example, a substantially non-flexible light guide delivery configuration, in the course of delivering the light energy, can prevent the knee from bending, which is typically encouraged during recovery. Further, a substantially non-flexible light guide delivery configuration can be uncomfortable or painful to wear for a specific treatment, thus discouraging patient compliance. Moreover, LLLT treatment applied to other areas not proximal to a wound area have been found to not be suitably effective, or may be wholly ineffective with inappropriate dosage, to enhance wound healing in that patient of a specific medical indication. Energy will thus be wasted, which will diminish the usability of the device because battery power will be depleted more quickly than if the LLLT delivery was provided efficiently.

In one aspect, the invention provides a wearable LLLT treatment device configured to provide a therapeutic dosage of LLLT to a person in need of treatment. In this regard, at least one substantially flexible light guide or light guide arrangement that is suitably conformable to the body area being treated is used.

The typical human skin surface has an average Shore A hardness from greater than zero to 30 or less, or greater 0 to about 20. In this regard, the materials used to fabricate polymeric light guides or light guide arrangements can have a Shore A hardness of from greater than 0 to about 30 for direct contact with skin in sensitive areas of the body for desirable comfort, flexibility, wearability and to prevent pressure injuries to the body. The polymeric light guides or light guide arrangements can optionally be provided with a lining material positioned between the skin surface and the light guide or light guide arrangements to reduce patient friction, as long as the lining material suitably allows LLLT treatment to reach the patient. For less tactically sensitive parts of the body or where more rigid light guide configurations are suitable, a light guide or light guide arrangements can be fabricated from materials with Shore A hardness up to about 75, optionally with a light transmissive lining material positioned between the skin surface and the light guide. In some aspects, even for direct skin contact in the sensitive area, harder materials, that is having Shore A hardness of greater than about 75 can be appropriate. For example, vaginal dilators for vaginal therapy as discussed elsewhere herein can use materials in the about Shore A 80 to about 100 range. It is known to people in the art the various hardness scales can be used to express the same material characteristics. For clarity, the Shore A and Shore D scales are used for this disclosure as indicated.

Flexible polymeric light guides or light guide arrangements suitable for use herein can be fabricated from moldable optical silicone resins, such as those made by Krayden® (Dow Corning, Corning N.Y.) or such as TPX™ Polymethylpentene (PMP) from Mitsui Chemicals America. Suitably flexible light guides or light guide arrangements can also be fabricated from polyurethane, as set out in U.S. Pat. No. 7,433,565, the disclosure of which is incorporated herein in its entirety by this reference. Flexible light guides or light guide arrangements can also be made with appropriate hardness (optimally Shore A 0 to about 30 for most parts of the body, may be higher for less tactile sensitive or thicker skin, such as the soles of the feet) and high elasticity (up to about 500% deformation with tension). Materials suitable for use as light guides or light guide arrangements can be molded into lengths appropriate for various LLLT treatment devices of the present invention using known methods.

For effective delivery of adequate light and scattering to the skin area, the cross-sectional area of a polymeric light guide or light guide arrangement must be appropriately sized. In some aspects, the light guides can have dimensions of at least about 1 mm by about 3 mm in a cross section. In some applications, the inventor has found that larger dimensions may increase the risk of pressure wound to the skin of a treated patient. However, the specific diameter appropriate for each indication can be readily determined by one of ordinary skill in the art without undue experimentation.

For some configurations, each of the at least one light guide or light guide arrangement can emit light substantially uniformly along the length thereof. Optimally, such uniform distribution can better ensure that only a small portion of the light entering each of the light guides or light guide arrangements is lost prior to delivery of the LLLT to the wound and associated areas. In other designs, the light guide or light guide arrangement is configured to emit light substantially non-uniformly along the length thereof, with certain sections to side-emit light while other sections to be non-emitting. With polymeric light guides or light guide arrangements, one or more areas on the interior surface thereof can be treated with a coating material to minimize light from exiting in areas where such light exit is not indicated. Such coating is optimally a reflective or mirrored coating while leaving the remainder of the light guide or light guide arrangement areas free of such reflective coating to allow light to exit to reach the patient treatment area. Such coating can be achieved using a physical vapor deposition process, such as evaporation or sputter deposition, or a chemical process such as chemical vapor deposition. The advantages of such coating application can be, in some aspects: (1) enhancing the efficiency of delivered light to targeted area from the light source, thereby achieving the same level of light energy density with lower power/battery requirement, which can allow smaller and, therefore more comfortably wearable and discrete PBM control modules; and (2) improving treatment outcomes by minimizing the effects of certain light wavelengths, (UV light for example), from unintentionally reaching areas on the patient where such light might cause damage or reduce LLLT treatment overall effectiveness.

As noted, fiber optics having side light emitting characteristics can be used in some implementations. When used, these side emitting fiber optics should also be suitably sized to enhance patient comfort during LLLT treatment.

Each of the at least one light guide or light guide arrangements are each, independently, operationally and optically coupled into an associated light guide engagement port on the PBM control module. Each light guide engagement port is configured to allow light generated by the at least one light source to be suitably introduced into each of the at least one associated light guide or light guide arrangement for distribution along the length thereof to provide LLLT treatment to an area proximal to the patient area in need of treatment and, optionally, any areas associated with healing of the wound.

In some configurations, the light guides or light guide arrangements comprise an external diameter along the length therein. In other aspects, the light guide or light guide arrangements can have an internal diameter and an external diameter. For example, for use in a nasal cavity, a light guide or light guide arrangement can have an internal diameter along the length therein to allow air to travel through the light guide or light guide arrangement to allow the patient to breathe while a least part of the insert is engaged with the patient's nasal cavity.

In a further aspect, a second, or terminal end, of each of the light guides or light guide arrangements can be coated to generate a total or partial mirror at one or more terminal ends of the light guide or light guide arrangement. The plane of a terminal end of the light guide or light guide arrangement can also be angled to provide an angle at the terminal end of from about 65 degrees to about 85 degrees so that light reflected from the terminal end will travel in the opposite direction in the light guide or light guide arrangement. Alternatively, the reflective coating at the end thereof can be in another shape, such as concave or convex mirror. Such mirrored coating at the end of a light guide or light guide arrangement has been found by the inventor herein to enhance light delivery from a patient facing side of the light guide or light guide arrangement. This, in turn, conserves energy, as well as improving the positioning of the reflected light beams at angles that can be more suitable for exiting the patient facing side when needed at areas closer to the LLLT treatment target(s).

The LLLT treatment is suitably dispensed from the at least one flexible light guide or light guide arrangement in a location substantially proximal to the wound in need of being treated. Each light guide or light guide arrangement can be configured to dispense LLLT from a patient facing side along a wound-facing side or relevant patient area substantially proximally to the selected treatment location on the patient, where the selected location comprises a medical indication in need of treatment. The ability to provide a LLLT dosage substantially configured to treat a selected area of a patient in need of treatment can be facilitated by using more than one light guide or light guide arrangement, where each light guide or light guide arrangement, independently, can be conformable or placed proximally to the patient area(s) being treated.

Each of the at least one light guide or light guide arrangements are engageable with the LLLT delivery element prior to use by the patient, for example, at the point of manufacture or at the point of care, to ensure that the desired LLLT treatment dosage delivery parameters are suitably provided to allow accurate dosages to be provided for a specific type of patient and the associated patient indication(s). In this regard, the at least one light guide or light guide arrangement can be engageably attached to the LLLT delivery element at the time of manufacture in a configuration that is appropriate for a specific medical indication. The LLLT treatment device can be pre-sized and pre-shaped for an assortment of patient relevant configurations for treatment of one or more specific medical indications.

For example, a LLLT treatment device can come preconfigured for use in treating a knee replacement (TKA) post-surgical condition. Accordingly, at the time of manufacture, the at least one light guide or light guide arrangement from which LLLT is delivered from the at least one light source in the PBM control module can be attached to the flexible brace material in the configuration that can distribute light in an area proximate to the incision in need to treatment with LLLT. In broader constructs, the LLLT delivery element (brace/garment/cast, bandage, insertable device) can be provided for selection in range of shapes (e.g., small, medium, large etc.) to accommodate a range of wound sizes, wound types, patient sizes, and the like.

As would be recognized, a therapeutic amount of LLLT treatment is suitably deliverable from the at least one light source to an associated light guide or light guide arrangement. Given the relatively low power nature of the light sources herein, such transmission to the patient treatment area must occur without significant light energy loss to maintain effectiveness of the dosage as prescribed or directed. In this regard, the connection between the at least one light source and a first end of each of the at least one light guide or light guide arrangement can be configured to result in low loss from the light source(s). Direct connection of a polymeric light guide or light guide arrangement to an associated engagement port can reduce effectiveness of light transmission due to the patient, at least in part, to the presence of an air gap between the at least one light source and the engagement end of an associated light guide. To counter, at least in part, such loss of light, a connector made of flexible optically transparent silicone, glass or other suitably hard and clear material can be used to connect the at least one light source to each of the at least one light guide or light guide arrangement to provide an effective operational and optical engagement or communication between the light source and first end of each of an associated light guide or light guide arrangement. Such optical connector is configured to have a diameter that is suitable to fit within each of the diameters of the engagement port and the light guide or light guide arrangement connectable therewith.

In a further aspect, and to provide a light guide or light guide arrangement with highly efficient connection for ease of exchanging light guides or light guide arrangements while still maintain high efficiency of light transmission, wearability and comfort for patient using a LLLT treatment delivery element, a light guide or light guide arrangement can comprise at least two levels of hardness incorporated therein. In this regard, a first section can comprise an area proximal to a light source engagement end having a Shore A hardness of greater than about 30 to greater than about 50, such as from about 60 to about 95. Such stiffer area can assist in reduction of light loss by providing a suitably tight connection between the optical coupler to thereby minimize the air gap between the engagement port area and an associated light guide or light guide arrangement to achieve higher light delivery efficiency from the light source(s) to the patient. A second portion of the light guide or light guide arrangement can be configured to be softer in the area that contacts the patient treatment areas, such as the incision or the skin. In this regard, the second portion can comprise a hardness rating more compatible with the hardness of normal skin tissue, for example greater than 0 to about 30 on the Shore A scale. The light guide or light guide arrangement having two sections two or more of differing Shore A hardness ratings can be produced by connecting the harder section with the softer section using a two-step injection molding or an ultrasonic welding process. Alternatively, the two or more hardness sectioned light guide or light guide arrangement can be created at once with dual-material simultaneous injection or pour molding.

A LLLT treatment device can be configured with a plurality of light guides or light guide arrangements configured for treating a plurality of conditions with assurance for compliance, monitoring and adjustment for LLLT treatment effectiveness. Such plurality can each, independently, be associated with a corresponding engagement port on one or more PBM control modules, where each engagement port is, independently, in communication with one or more light sources configured to provide LLLT treatment to a patient in need of treatment thereof.

Still further, when initiating a LLLT treatment for a patient, a provider can customize the treatment by prescribing and arranging at least one LLLT delivery element with associated light guides or light guide arrangements in a configuration to substantially match—that is, to conform to the size and shape of the patient area—in need of treatment. For example, a knee replacement patient in need of LLLT treatment can be specifically configured with a customized or patient-specific LLLT delivery element paired with specific dosage personalized for her specific needs.

The light delivery configurations herein can facilitate effective placement of a therapeutic dosage proximal to the patient area in need of treatment, as well as any associated "healing vital areas" (as such areas are described hereinafter), by the enhanced conformability of the LLLT light delivery to the area of the patient needing treatment. A further benefit of the configuration of the PBM control module and the delivery of the LLLT treatment herein is that there is substantially no source of electricity in the areas proximal to the wounds in need of treatment, and any associated healing vital areas. In this regard, the LLLT treatment devices and methods substantially differ from those methodologies that incorporate powered laser or LED lights etc. to provide power thereto, by way of direct wiring to a battery or a power cord, for example, in an area proximal to the patient body area being treated that may have the presence of electrically conductive liquid, such as blood, biological drainage, or sweat. Such arrangement of lights or lasers proximal to an open wound or proximal to the patient's skin, as opposed to the light delivery configurations of the present invention, substantially increase the risk of electrocution/shock and reduces the conformability of the LLLT delivery element, at least in part because of the structural aspects of the lights themselves. Such lack of conformability can be seen, for example, in U.S. Pat. No. 7,100,615, the disclosure of which is incorporated herein in its entirety by this reference.

Further, wounds are typically sensitive to temperature. Removing the lights or laser from the open wound reduces a potential point of discomfort for the patient leading to an improvement in compliance. In this regard, there is substantially no heat delivered from the light guides or light guide arrangements when these elements are delivering light to a patient treatment area.

Power or energy density of the light applied is a highly relevant parameter for the LLLT of the devices and methods herein. To this end, power density can be adjustable by a number of methods such as increasing the power output from the light source, changing the coupling between the light source and each of the associated light guides or light guide arrangements, coating a portion of the light guides or light guide arrangements along a length thereof, or modifying the areas of the patient that are treated with LLLT.

Energy density, which provides a relative dosage for an individual regimen, is also a relevant factor in the invention herein. For treatment administered over an extended period, an overall therapeutic dosage can range from about 0.1 $J/cm^2$ to about 15 $J/cm^2$, with the amount of energy applied per individual dosage period depending, at least in part, on the patient's condition, location on the body, phenotype, BMI, among others parameters, being treated. For example, pain treatment provided shortly after a medical procedure may require a higher initial dosage. A therapeutic dosage range for wound healing has been found to be from about 2 to about 5 $J/cm^2$.

A variety of light wavelengths can be appropriate for LLLT treatments herein. Generally, light in the ultraviolet, various visible ranges, and infrared light can each be, individually, indicated for treatment of a wound or other patient indication at certain stages of patient treatment. Accordingly, at least one aspect of the invention herein comprises selection of at light having a wavelength or wavelength range appropriate for treating of a patient wound or medical condition in need of treatment.

Depth of LLLT penetration into a patient's tissues in need of treatment can be enhanced by using wavelengths in the infrared range, increasing the power, and by using laser light that comprises a collimated beam, as opposed to SLD and LED that generally do not.

In one aspect, the PMB control module of the present invention for post-surgical care comprises at least one, or two, or three or more light generating components (i.e., light sources), a controller, on-board memory, one or more sensors, a communications module, a battery power source, at least one light guide engagement port, and a housing or other containment structure. The light generating components, which can be in the form of a laser diode or an LED or other suitable source, can be configured to generate light in one or a plurality of wavelengths or in wavelength ranges of from about 200 nm to about 1000 nm. Still further, the light generating components can generate light in at least three wavelengths: for example, 590 nm, 650 nm, and 808 nm, individually or simultaneously. The ratings on laser diodes used in the present invention can be from about 5 mW to about 250 mW and the rating for LED light sources can be from about 3 mW to about 120 mW. The PBM control module is configurable to provide signaling and control to each of the components and functions associated with generation and monitoring of a LLLT treatment regimen. The at least one light guide or light guide arrangement is in operational and optical engagement and, therefore, communication, with the PBM control module.

In some configurations, on-board memory can store the programs and instructions to execute the desired functions as well as storing the time, number of completed treatments, any information from the sensors and instructions from physicians or the remote servers associated with the LLLT treatment delivery system in response to changes detected or patient input received. Alternatively, data associated with the operation of the LLLT treatment devices can be transmitted or delivered to a remote device and/or server substantially in real time. Yet further, data associated with operation of the devices can be stored in the on-board memory module for a period of time, and then transmitted to and from a remote device and/or server. Such information associated with patient treatment can be valuable to manage treatment and outcome to monitor patient compliance and for the adjusting of treatment parameters based on real-time progress and feedback. Data with respect to treatment duration and cycles can be used to facilitate billing including reduction of billing fraud by ensuring that a device was in fact used.

Sensors associated with a PBM control module can include, but are not limited to, identification sensors that are associated with the light guide or light guide arrangement engagement port(s), wound condition sensors, accelerometer, dosage, wavelength and temperature sensors. The wireless communication module can employ any available technologies, such as Wi-Fi or Bluetooth®, with HIPPA compliance or secure encryption suitably present to enable authorized and predetermined data transmission between a PMB control module to another PMB control module, or to the server of the system, or directly to other devices to enable and to ensure optimal outcome with LLLT treatment. The housing can be made of plastic or metal or a combination thereof.

The PBM control module can be powered by one or more batteries a rechargeable lithium ion battery having sufficient capacity to power the power module for a sufficient time to provide a wearable treatment. In this regard, the capacity of the battery can be suitable to provide at least about 6, 12, 18, or 36 hours of operation for the device between recharging. Battery charging can be provided by a plug or wireless charger. In some aspects, the battery pack can be exchanged to allow substantially continuous use for the device. The battery capacity can be balanced between the need for long times between charges and the weight of the battery. In this regard, the battery capacity can be from about 0.5 Ah to about 3 Ah, with about 2 Ah being particularly suitable.

The PBM control module can be configurable to collect data associated with treatment compliance, healing progress, patient safety, as well as to activate, deactivate or modify certain functions or treatment parameters. Such intelligence can improve ongoing operation of the LLLT treatment devices and methods of the present invention. For instance, if an accelerometer is associated with the LLLT treatment device, generated accelerometer movement data may be used to trigger a delivery of LLLT to the knee to reduce pain as indicated by a patient's measured degree of mobility over time after the surgery.

In another example, a wound healing progress sensor associated with a PBM control module may be most effective when the room is dark. Accordingly, the PBM control module can be configured to use information related to the combination of movement, temperature and ambient photosensor data to control the optic sensor designed to detect treatment progress using blue light reflection from the skin and wound when the patient is in a darkened environment. Alternatively, the sensor can be configured with an opaque or black out material to create an artificially darkened microenvironment around the sensor.

In some aspects, software instructions associated with the PBM control module can be configured to perform some or all of the clinically appropriate treatment functions, such as treatment programs, data storage, sensor operation and a dosage meter. The "dosage meter" feature can allow the PBM control module to better ensure patient safety by shutting off the light source to avoid over exposure and alert the provider, for override or for receipt of other instructions. Such dosage provision limitation feature, along with one or more associated features of light guide or light guide arrangement recognition, LLLT power limitation, sensor feedback and battery capacity limitation to a predetermined charge interval, can be useful provide a multi-layer of built-in safety measure for avoiding unintended "overdose."

Further, the PBM control module can include functionality to generate new or to modify a prescription in real or near real time, based on patient feedback. Such modification can enable provider intervention in response to the delivered dosage history and compliance log of a patient. As a non-limiting example of this aspect, a patient being treated for wound recovery after a Cesarean section, can be provided with a Visual Analog Scale (VAS) pain tracking interface on the app on her mobile phone which interacts with PBM Control module. On post-op days 0 to about 14, she can be prompted to enter her pain level at predetermined times each day on the VAS. Such pain information can be used to allow remote monitoring of the patient via telemetry, for example. The patient then may be able to leave the hospital earlier with her baby.

Alternatively, the monitoring interface can incorporate a Global Rate of Change chart (GRC). Information related to treatment time, time since treatment start, patient input, and the general trend, among other factors, can be used to recommend adjustments to the PBM control module operation, such as by being incorporated into software instructions, to improve pain treatment in one or more subsequent treatments. A provider can remotely approve and enable the new treatment regimen, such as LLLT treatment dosage, and such new treatment can be delivered via updated instructions to the PBM control module for application of such new dosage to the patient.

The wearability of the LLLT treatment devices enable a plurality of dosage treatments to be administered to a patient in need of treatment during an overall treatment protocol. The PBM control module can configure the one or more light sources to deliver light to the light guide arrangements, and thus the patient tissues in need of treatment, in continuous or pulsed mode during a particular dosage period.

The overall power delivered to the patient during a treatment period can be decreased by pulsing the light. Overall power delivered to the patient during an individual dosage period can be varied by pulsing the light. When pulsed mode is used the average power delivered will decrease proportional to the pulse frequency that is selected. Setting the pulse frequency determine the number of pulses delivered per second during a pulsed LLLT treatment. Pulse frequency is measured in Hertz (Hz). When a low pulse frequency is selected the pause between laser pulses is greater so less power is delivered. When high pulse frequencies are selected there is less of a pause between laser pulses e.g., it is closer to continuous output. The average (or mean) power is used to describe the net power delivered after factoring for both the on and off time of the beam.

Selecting a duty cycle that pulses the laser beam will decrease the net power (mW) delivered. Generally, for LLLT treatment intended to reach deeper into the surface tissues of a patient, continuous or substantially continuous treatment during an individual dosage period can be selected. The amount of pulsing, and therefore the power applied to the patient's tissues can be modified—that is, decreased or increased—during an overall patient treatment protocol as described elsewhere herein.

Power density describes the average power per unit area of the light beam that reaches the tissues. It is measured in $W/cm^2$ or $mW/cm^2$. The power density is determined by dividing the power level of the laser by the area that the beam is emitted from the light guides.

Energy is the power multiplied by the treatment time. It is measured in Joules (J). The amount of energy delivered in Joules does not account for the area of the laser beam or the area of the surfaces being treated.

Figure 17:
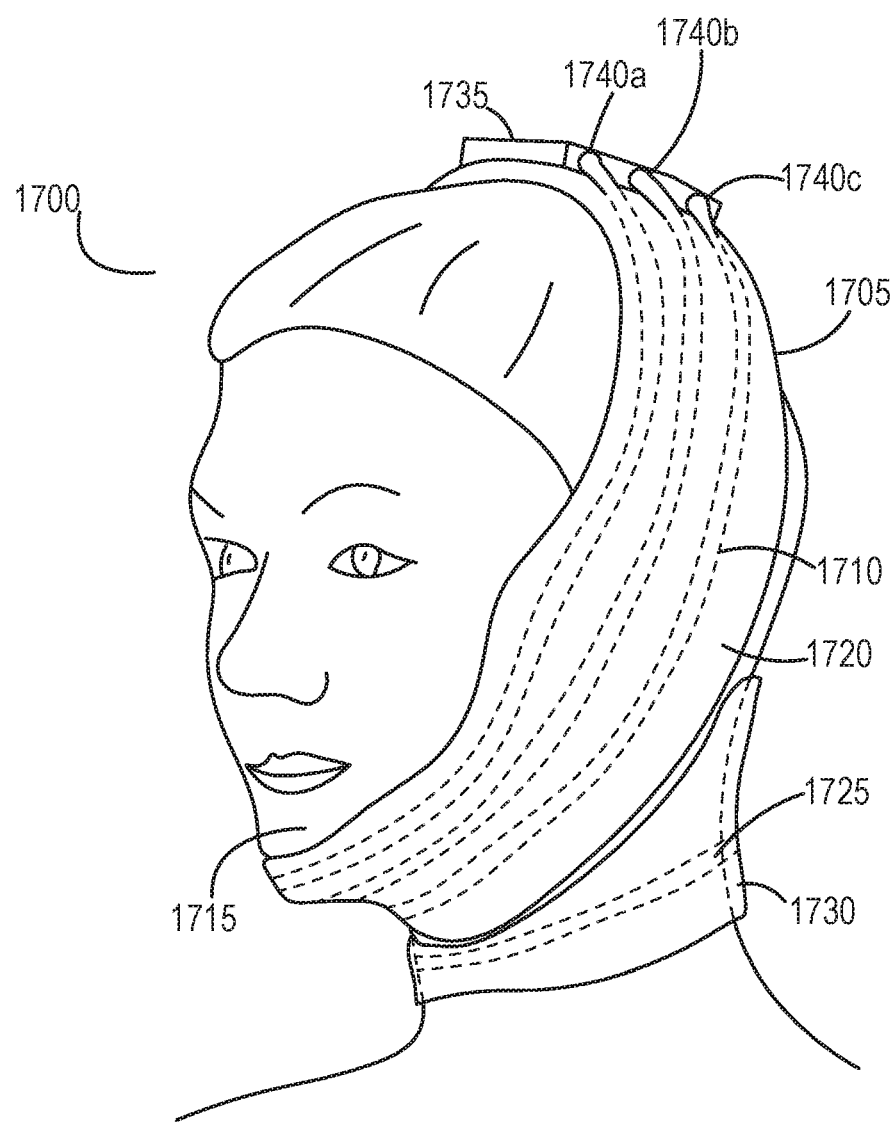
FIG. 17 illustrates a LLLT device for treatment of facial and neck areas.

Various wavelengths of light associated with wound healing have been reported at generally being effective between wavelengths of about 600 to about 900 nm (see e.g., FIG. 17 of U.S. Pat. No. 8,784,462, the disclosure of which is incorporated herewith in its entirety by this reference). The specific wavelengths identified in the '462 Patent as being most effective for healing were reported to be about 620, 680, 760, and 820 nm. Laser diodes, SLD, and LED lights are readily available to emit light in these indicated wavelengths.

Blue light in the range of from about 450 to about 495 nm is further known to be effective for disinfection. Since wound disinfection is also relevant to wound healing, light in this nm range is also contemplated with the LLLT treatment devices and methods of the present invention. Wavelengths in the UV spectrum can also be effective in disinfecting a wound when signs of infection is detected or confirmed by the healthcare provider. For a disinfection application, direct UV-emitting laser diodes are available at 375 nm are available to use. A UVC LED can be used for disinfection. For sensor applications, LED at about 365 nm or about 395 nm with up to about 20% input to light efficiency, and power outputs at these longer UV wavelengths are suitable.

It may be desirable to provide a PMB control module(s) that is capable of delivering more than one light wavelength. For example, atopic dermatitis can be treated with a device using, for example, a combination of UVB and UVA wavelengths. Multiple wavelengths can also be advantageous in the case of a wound farther below the surface since the use of light in the red spectrum to provide light energy to the tissue immediately below the skin; while the use of a light in the infrared range can travel deeper into the patient's body to aid in healing the broken bone, for example. For deep incisions like C-sections, a deep tissue effective wavelength and wound relevant wavelengths can also be beneficial.

Different wavelengths, such as a first, second, third, fourth etc. wavelengths or wavelength ranges, can be used for different stages of the wound healing. For example, during the hemostasis and inflammatory phases, red light near the about 650 nm range provide benefits of reduction in bruising and swelling. While red and near infrared of about 810 nm can provide significant pain relief at a higher dosage, as much as 15 J/cm$^2$ delivered during the inflammatory phase during the first about 24 to about 72 hours depending on the individual patient's condition. During the proliferative phase of wound healing, infrared spectrum near about 810 nm can improve wound closure by, for example, stimulating endothelia genesis, growth factor, myofibroblasts and collagen production to regains to the level of about 80% of the skin's original strength. During the scar maturation phase, a combination of amber light at about 590 nm can be delivered with red light at near about 650 nm at a low level (0.1-1 J/cm$^2$) on a daily basis for up to about 120 days to reduce or prevent the formation of keloid or hypertrophic scars.

Alternatively, it may be desirable to provide a first light wavelength for a first-time period, followed by a second, third, fourth etc. light wavelength at respective second, third, fourth etc. time periods that are each, independently, different from one or more of the other applied wavelengths and/or time periods. Still further, different applied wavelengths can be varied within multiple patient locations on the same patient during a single LLLT treatment regimen, for example one wavelength can be selected for the wound site, and one or more second wavelength grouping(s) for sites associated with healing of the wound site or for locations deeper below the skin surface, such as blood supply to and from the wound, or lymph nodes with drainage from the wound.

LLLT light delivery can be operated by the microprocessor that controls activation of the laser diode(s) or LED(s) or SLDs at predetermined duty cycles or frequencies in accordance with the treatment regimen(s) generated by a provider for that patient. The software instructions associated with a LLLT treatment regimen or protocol can define a total treatment period, one or plurality of individual treatment periods to occur over the total treatment period and one or more wavelengths of light to be emitted by the light sources in each PMB control module for delivery to the patient from the light guide(s) or light guide arrangement, among other things.

A notable aspect of the present invention is that the at least one light guide or light guide arrangement is configurable to be associated with a corresponding validation component, where the validation component is in operational engagement with the control model and the associated componentry. In this regard, prior to dispensing the LLLT to a patient, the device is configured to validate that each of the at least one light guide or light guide arrangements and/or control module are suitably configured in an appropriate delivery element. When the at least one light guide or light guide arrangement and/or PBM control module is validated as being appropriately configured to dispense a desired LLLT dosage to a patient, the device can be configured to proceed with a LLLT treatment. If the at least one light guide or light guide arrangement is not appropriately associated with the delivery element, the control module can be configured to not to deliver the LLLT.

In further aspects, one or more of the light guides or light guide arrangement configurable with one or more PBM control modules is each, independently, configurable to communicatively identify itself when the light guide or light guide arrangement engagement end is engaged with an associated engagement port. In this regard, instructions associated with the PBM control module can be configured to match or validate an associated light guide(s) or light guide arrangement(s) that is engaged with a corresponding engagement port. If the expected engagement port/light guide or light guide arrangement match is not generated when the light guide or light guide arrangement is engaged in the engagement port, the PBM can be configured to not activate. A signal can be sent to the provider and/or patient notifying them of the lack of validation.

In some aspects, each delivery element for use with the PBM control module and the LLLT delivery element is durably validatable via one or more methods. For example, each at least one light guides or light guide arrangements incorporated into the delivery element can incorporate a light guide/light guide arrangement identification tagging or code that is transmittable to a signal receiver associated with the PBM control module. Such tagging or identification can be by a validation module associated with a PBM control module suitably configured to read RFID information, bar code scanning, color coding, direct connection circuit (e.g., wires directly connected between the machine and a small chip on the mold), physical (such as physical teeth and groves as a key on a light guide) and active systems where communications (e.g., Wi-Fi, Bluetooth) are natively embedded with the at least one light guide or light guide arrangement. The validation tag or code associated with a light guide/light guide arrangement and the validation module can be durably incorporated into the light guide or light guide arrangement during the molding process, for example. Alternatively, or in conjunction therewith, the LLLT delivery element can incorporate an RFID tag etc. that is in operational communication with the validation module.

In some aspects, the light guide or light guide arrangement validation element and/or delivery element validation functionality can allow confirmation that a particular light guide or light guide arrangement and associated LLLT treatment delivery elements are authorized for use with the PBM control module and dosing instructions associated therewith. To this end, an authorization code can be incorporated into software instructions provided to the PMB control module. To ensure that patients are authorized to receive a LLLT treatment and any associated dosage, as well as to ensure that the desired therapeutic amount of LLLT can be provided to the patient in need of treatment as directed by the medical provider, the PBM control module's power source can be configured to lockout or otherwise disable any non-validatable light guides/light guide arrangements and associated LLLT delivery elements from being operational. In other words, the PBM control module can be configured to render each of the components individually and collective inoperable unless either or both of the light guide(s) and/or LLLT delivery elements can be validated as authorized for use to provide a therapeutic patient treatment.

As would be recognized, non-validatable (that is, non-approved or unregulated) LLLT treatment devices might not be configured to the necessary specifications needed to ensure that a patient will receive an appropriate dosage. Such specifications can include parameters such as treatment time, total energy, energy density, power density, cycle time, light application frequency, light intensity, wavelength, among others. For certain light wavelengths, such as UVC, too little or too much application of light therapy can result in harm to patients or lack of benefits from an applied LLLT treatment.

Software instructions associated with the PBM control modules of the present invention can be configurable to identify the treatment delivery element and light guide or light guide arrangement configurations engagable with the communications module via a unique identification code that is transmittable to and detectable by a light guide or light guide arrangement identification signal receiver associated with the PBM control module as authorized for use. If the unique identifier provided by the at least one light guide or light guide arrangement (or if the unique identifier is missing) determines that the light guide or light guide arrangement is not authorized, instructions associated with the PBM control module is configurable to lockout the LLLT treatment device from use, such as by deactivating one or more aspects of the PBM control module, such as power source and/or light source until the mismatch is corrected by attaching an authorized light guide or light guide arrangement. The instructions optionally include an override that can allow the device to allow operation without the at least one light guide or light guide arrangement having an authorized identifier code, however, that override should only be operable by the device manufacturer or the medical provider with access authorization permission, such as with an access code, or a key.

When the provider is defining a treatment regimen for a patient in need of treatment, information associated with the LLLT delivery element and light guide/light guide arrangement identification, that is, a unique code that is registered to an appropriate data source, can be incorporated into instructions associated with the device. Each of the delivery elements and/or light guides or light guide arrangements used in a particular treatment can be identified, with data representing type, size, configuration, and authenticated serial number that a PBM control module can use to associate with a treatment, a legitimate purchase of the treatment element by a patient, a medical institution, or a provider, therefore, as being authorized for use. Such delivery elements and/or light guides/light guide arrangements will not be registerable for use with another patient's LLLT treatment, thereby reducing the possibility that the device will be reused in an unauthorized manner.

The LLLT delivery element (e.g., brace/cast, bandage, or insertable element) can also be configured with a unique identification code that can be transmittable to the communications module. The LLLT treatment device can therefore be configured to be inoperable unless the delivery element is suitably matched to a unique LLLT delivery element identifier defined as authorized for use with the PBM control module, and any associated LLLT patient treatment regimen.

As with the light guide/light guide arrangement identification code, the LLLT delivery element identification code can allow a match to be ensured prior to the delivery of a LLLT dosage to a patient. Accordingly, the software instructions associated with the LLLT treatment devices of the present invention can be configurable to identify the delivery element engaged with the communications module via a delivery element identification code that is transmittable to a delivery element identification signal receiver associated with the PBM control module as authorized for use in the delivery element. If the unique identifier provided by the delivery element (or if the unique identifier is missing) determines that the delivery element is not authorized, the software associated with the LLLT treatment device is configurable to notify the server, provider or other parties of such incidents of attempt for unauthorized use, to lockout the communications device from use, such as by deactivating the power source and/or light source until the delivery element mismatch is corrected. The software optionally includes an override that can allow the device to operate without the delivery element identification code being authorized. However, that override should only be operable by the device manufacturer or the medical provider with proper authorization.

In a significant aspect, the PBM control module can be configured to be interchangeable with any treatment form in which the LLLT delivery element can be provided. That is, a single PBM control module can be used for the brace, garment, blanket, accessories, bandage, or insertable devices etc. of the present invention for LLLT treatments. A PBM control module can be registered to or otherwise identifiable with a single patient. Stored and acquired patient personal and health record information can deployed as needed for that patient in accordance with a first LLLT treatment associated with a first PBM control module. Subsequent LLLT treatments using the first PBM control module, which can be used with the same or different LLLT delivery elements engageable with the first module, can utilize patient health information stored or otherwise configured therein, including information associated with the response of that patient to prior LLLT treatments, can be deployed for subsequent treatments associated with that PBM control module and patient.

A PBM control module can also be assigned to a group of patients. In this regard, a PBM control module can be maintained in location away from open wounds, to remain free of contamination. The PBM control module can also be treatable to reduce or eliminate contamination between uses or users, such as by wiping down with disinfectant, placing in a disinfection cabinet or the like. Alternatively, a sterilizable or disposable cover may be used to protect the PBM from contamination. The cover can optionally include antimicrobial materials such as triclosan or silver.

A specific LLLT delivery element identifiably assigned to each user that can be specifically associated with each person's condition, size, BMI, skin tone, among other information, and the PBM control module interchangeable therewith, by detecting the LLLT delivery element associated with a particular patient, for example, to enable automatic personalized light dosage delivery. Because the LLLT delivery element likely comes into contact with the patient's bodily fluids or the like, it can be desirable that each of LLLT delivery element is uniquely matched to each patient to reduce or eliminate the possibility of patient cross-contamination. In this regard, RFID or other signaling capability can be implemented in the LLLT delivery element to lock out or otherwise disable the PBM control module unless the appropriate matching with a LLLT delivery element is achieved. For example, the patient or provider can be required to enter a password that is generated to allow the PBM control module to activate, even when the appropriate matching between the light guide and PBM control module is provided via RFID, electrical connection or otherwise.

The LLLT treatment devices and methods of the present invention have broad application in treating a wide variety of patient medical or aesthetic indications in need of treatment. Table 1 below provides a non-limiting list of medical and aesthetic indications that can be effectively treated for improved post-surgical recovery. In this regard, the present invention comprises selecting a patient medical indication in need of treatment, such as one or more medical or aesthetic indications identified in Table 1, providing a LLLT treatment device comprising a PBM control module comprising at least one light source configurable to deliver a wavelength or wavelength range of LLLT to a patient area in need of treatment, wherein the LLLT is delivered to the patient via one or more light guides or light guide arrangements in engaged with a corresponding engagement ports on the PBM control module.

TABLE 1

| Category | Plasty | Ectomy | Stomy | Otomy | Other | Primary LLLT Treatment Objectives | Other LLLT Treatment Objectives |
|---|---|---|---|---|---|---|---|
| Central Nervous System | | Decompressive craniectomy Hemispherectomy Anterior temporal lobectomy Hypophysectomy Amygdalohippocampectomy | Ventriculostomy | Craniotomy Pallidotomy Thalamotomy Lobotomy Bilateral cingulotomy Cordotomy Rhizotomy | Neurosurgery Psychosurgery Brain biopsy | Pain | Speed of Recovery And Healing |
| Peripheral Nervous System | | Ganglionectomy Sympathectomy/ Endoscopic thoracic sympathectomy Neurectomy | | Axotomy Vagotomy | Nerve biopsy | Pain | Speed of Recovery And Healing |
| Endocrine | | Hypophysectomy Thyroidectomy Parathyroidectomy Adrenalectomy Pinealectomy | | | | | |
| Eye | Punctoplasty Trabeculoplasty | Photorefractive keratectomy Trabeculectom Iridectomy Vitrectomy | Dacryocystorhinostomy | Radial keratotomy Mini Asymmetric Radial Keratotomy (M.A.R.K.) | Corneal transplantation | Pain | Speed of Recovery And Healing |
| Ears | Otoplasty | Stapedectomy- Mastoidectomy Auriculectomy | | Myringotomy | | Pain | |
| Respiratory | Rhinoplasty Septoplasty | Rhinectomy Laryngectomy Pneumonectomy | Tracheostomy | Sinusotomy- Pneumotomy Cricothyroidotomy Cricothyrotomy Bronchotomy Thoracotomy Thyrotomy Tracheotomy | Pleurodesis Lung transplantation | Pain | Speed of Recovery And Healing |
| Cardiovascular Lymphatic | Angioplasty Valvuloplasty | Pericardiectomy Endarterectomy Tonsillectomy • Adenoidectomy Thymectomy • Splenectomy Lymphadenectomy | | Cardiotomy- Pericardiotomy | Heart transplantation Thymus transplantation • Spleen transplantation • Splenopexy Lymph node biopsy | Pain Pain | Swelling |
| GI/mouth | Uvulopalatoplasty Palatoplasty | Gingivectomy • Glossectomy Esophagectomy Gastrectomy Appendectomy Proctocolectomy Colectomy Hepatectomy Cholecystectomy Pancreatectomy Pancreaticoduodenectomy | Gastrostomy (Percutaneous endoscopic gastrostomy) Gastroduodenostomy Gastroenterostomy Ileostomy Jejunostomy Colostomy Cholecystostomy Hepatoportoenterostomy Sigmoidostomy | Uvulotomy Myotomy (Heller myotomy Pyloromyotomy) Anal sphincterotomy Lateral internal sphincterotomy | Vertical banded gastroplasty Gastropex Colon resection Nissen fundoplication Hernia repair Omentopexy Liver biopsy | Pain | Speed of Recovery, Healing and swelling |
| Oral Maxillofacial | Gingival flap Bone grafting Cleft and Craniofacial Surgery Reconstructive Surgery Cosmetic | Gum surgeries Dentoalveolar Surgery | Dental Implants | | Orthognathic Surgery •Maxillofacial Trauma •Temporomandibular Joint | | |

TABLE 1-continued

| Category | Plasty | Ectomy | Stomy | Otomy | Other | Primary LLLT Treatment Objectives | Other LLLT Treatment Objectives |
|---|---|---|---|---|---|---|---|
| | Surgery Surgical Correction of Maxillofacial Skeletal Deformities | | | | | | |
| Urinary | Urethroplasty Pyeloplasty | Nephrectomy Cystectomy | Nephrostomy Ureterostomy Cystostomy (Suprapubic cystostomy) Urostomy | Nephrotomy | Nephropexy Urethropexy Lithotripsy Kidney transplantation Renal biopsy | Pain | Infection |
| Male Reproductive | Phalloplasty Scrotoplasty | Vasectomy Penectomy Orchidectomy Prostatectomy Posthectomy Gonadectomy | | Vasovasostomy Vasoepididymostomy | Meatotomy | Circumcision Foreskin restoration Orchiopexy Prostate biopsy | Pain |
| Female Reproductive | Vaginoplast Clitoroplasty Labiaplasty Tuboplasty • Fimbrioplasty | Cervicectomy Clitoridectomy Oophorectomy Salpingoophorectomy Salpingectomy Hysterectomy Vaginectomy Vulvectomy | Salpingostomy | Amniotomy Clitoridotomy Hysterotomy Hymenotomy Episiotomy Symphysiotomy | Tubal ligation Tubal ligation reversal Colporrhaphy • Cesarean section Hymenorrhaphy Endometrial biopsy | Pain | Speed of Recovery and Healing |
| Bone, | bone: Acromioplasty • Khypho-plast Mentoplasty Acromioplasty | bone: Osteotomy (Femoral head osteotomy Vertebrectomy Coccygectomy stragalectomy) Corpectomy Facetectomy Laminectomy (Hemilaminectomy) | | bone: Osteotomy | bone: Epiphysiodesis | Pain | Speed of Healing, Recovery, Range of motion, |
| cartilage, and joint | joint: Arthroplasty Rotationplasty | joint: Synovectomy • Discectomy | | joint: Arthrotomy Laminotomy Foraminotomy | joint: Arthrodesis Arthroscopy Ulnar collateral ligament reconstruction | Pain | |
| Muscle/ soft tissue | | Bursectomy amputation (Hemicorporectomy, Hemipelvectomy) | | Myotomy Tenotomy Fasciotomy | Muscle biopsy Amputation Tendon transfer | Pain | Speed of Recovery and Healing |
| Breast | Mammoplasty | Lumpectomy Mastectomy | | | Breast implant • Mastopexy • Breast reconstruction • Breast reduction plasty | Pain | Speed of Recovery, Healing, scar minimization |
| Skin | V-plasty VY-plasty W-plasty Z-plasty | | | Escharotomy | Skin biopsy | Pain | Bruising, abnormal scar prevention |
| Other/ ungrouped | Abdominoplasty Hernioplasty Frenuloplasty • Z-plasty | Diverticulectomy Frenectomy Hemorrhoidectom Mastoidectomy Thrombectomy Embolectomy Ganglionectomy Lobectomy Myomectomy • Panniculectomy | Ureterosigmoid ostomy | Fistulotomy Laparotomy Myringotomy Sphincterotomy Commissurotomy | Abdominal surgery Inguinal hernia surgery Biopsy Brostrom prodedure Cauterization Grafting Hypnosurgery Laparoscopy Radiosurgery • | Pain and bruising reduction | Speed of Recovery, Swelling and Healing |

In one aspect, the at least one light guide or light guide arrangement can be attached or mounted to a knee garment, a hip garment, a wrist garment, an ankle garment etc., where such a garment (or brace) is generally configurable to surround an area on the body. Similar configurations for this LLLT delivery element would comprise a brace or a cast. As would be recognized, such garments (or braces) are useful for joint replacement or other surgeries, where structural support proximal to the patient area being treated can be desirable. In this regard, a properly configured LLLT treatment dosage, has been found to greatly enhance the healing, as measured by pain measurement, swelling, bruising, mobility recovery, etc. in a patient who has received a total or partial knee or hip replacement surgeries, also called "Total Knee Arthroplasty" and "Total Hip Arthroplasty." Yet further, such LLLT delivery element configurations can be beneficial for repetitive stress injuries, muscle strains, fractures, breaks or the like.

When the treatment LLLT treatment device is configured in the form of a brace or the like, the LLLT delivery element can also function, at least in part, to provide compression. Such compression can enhance healing, thus potentially resulting in further improvements in healing. One non-limiting application of a LLLT treatment device that, at least in part, can be compression device, such as an inflatable sleeve over a leg or an arm, include one or more light guides or light guide arrangements configured to provide light therapy in a post-surgery environment to prevent DVT (deep vein thrombosis) and improve circulation of lymphatic and blood flow. In another non-limiting application of a LLLT treatment device that, at least in part, incorporates compression along with LLLT treatment can be a sports bra-like garment that can include one or more light guides or light guide arrangements configured to provide light therapy in a post-surgery environment to enhance healing of the breast area after mastectomy, augmentation, or reduction surgeries. In yet another non-limiting application of a LLLT treatment device that, at least in part, incorporates compression along with LLLT treatment can be incorporated along with the garment, so that any incision areas can be treated with at least one light guide or light guide arrangement oriented proximally to the incision(s), and any associated healing areas, for example, armpit lymph nodes, can be treated with light guides or light guide arrangements that are suitably configured to apply therapeutic light proximal thereto. Still further, proper compression combined with LLLT treatment would be appropriate for a stress or strain injury associated with pain, for example.

In use, the at least one light guide or light guide arrangement can be attached to or mounted on or otherwise associated with the LLLT delivery element, where the element is configured in the form of a garment/brace/cast, bandage, or the like. In some aspects, the at least one light guide or light guide arrangement will substantially not be evenly distributed along a length and or width of a patient facing side of the delivery element. Rather, the light guide(s)/light guide arrangements and any associated LLLT delivery can be arranged to provide the desired light distribution proximal to the wound in need of treatment (and any associated healing vital areas).

When the at least one light guide or light guide arrangement is incorporated into a LLLT delivery element that is in the form of a brace or garment or cast, the at least one light guide or light guide arrangement can be glued, sewn, mounted, ultrasonically welded or otherwise durably attached to the delivery element. In some aspects, the at least one light guide or light guide arrangement can be attached to the LLLT delivery element by incorporating each of the light guides with a plurality of loops, where a first and second side of each loop is durably attached to a patient facing side of the delivery element, where such durable attachment can be by sewing, adhesive, ultrasonic welding, or the like. Such attachment can also be used for other LLLT device configurations herein.

As discussed elsewhere herein, an aspect of the present invention relates to the LLLT being delivered substantially proximally to the wound or patient area in need of treatment (and any areas associated with wound healing) whereby the light guide(s)/light guide arrangements are configured to fit to the general shape of the body area (and any associated areas) where a wound or treatment area is located. It follows that, in use, any association of the light guide(s)/light guide arrangements with the LLLT delivery element can substantially not reduce the flexibility and, therefore, conformability, to the patient area(s) being treated. However, to ensure that that the LLLT delivery will remain in the desired location in use, the light guide(s)/light guide arrangements can be durably attached to the delivery element so that movement from the desired light placement is minimized during patient movement when she is wearing the LLLT treatment device.

Alternatively, the at least one light guide or light guide arrangement can be attached to or mounted on or proximal to a LLLT delivery element that is in the form of a garment. For example, a patient who has undergone facial surgery (e.g., a face lift or reconstruction surgery) will have an incision wound that in need of healing. Since the wound has exudate during the early phase (typically the first about 48 hours post-operation) of healing, an absorbent gauze or sponge will generally be placed on the wound to absorb the fluids. When applied over a surface (as compared to around a joint, limb or the like), the LLLT treatment device of the present invention can comprise a garment or bandage that overlies the sterile and absorbent material, also called the primary dressing. Any material that covers a patient area, should be suitably transmissive to the LLLT being applied. For example, the absorbent material can be combined with a window or opening to allow both LLLT to be delivered to the patient area and wound exudate to be absorbed. In use, the absorbent material can be changed regularly, and the PBM control module re-used for that patient.

The present invention further provides devices and methods to enhance the healing and to reduce pain after facial surgery at both the incision area and in areas associated therewith that are prone to swelling. In one aspect, a garment or bandage can be configurable with one or more light guides to suitably deliver LLLT to a patient who has been subjected to surgery in the face or jaw. Such treatment can optionally comprise compression and heat and/or cold therapy to further enhance healing and reduce swelling.

The facial and neck area LLLT treatment device can comprise a patient facing side from which LLLT can be delivered from at least one light guide/light guide arrangement. The bandage is suitably stretchable and conformable to provide a suitable fit to the various areas of the face and neck. At least one light guide or light guide arrangement is configured to deliver light from a patient facing side of the device. The at least one light guide or light guide arrangement is in operational and optical engagement with a PBM control module that is mountable in a location that is comfortable for the patient. In this regard.

In further configurations, the LLLT delivery device for treatment of head and neck areas can be comprised of a flexible elastic material for securing the device around the head of patient. Suitable fasteners can be used to provide securing, such as Velcro®, clips, snaps, elastic or other straps or the like.

The head and neck areas LLLT treatment device is configured to provide suitable coverage of a patient's face, including at least the sides proximal to the cheeks and, optionally, over and behind one or both of patient's ears. The amount of coverage needed for a specific patient is largely dependent on at least the amount and number of incisions in the patent's head and neck areas, and the response of the patient to the procedure.

In some aspects, the head and neck area LLLT device can further be configured to provide cold therapy in conjunction with LLLT treatment. In this regard, a portion of the head and neck area device can be configured to be fillable with crushed ice or liquid gel that is freezable, to allow a combination of LLLT treatment, compression and cold therapy to areas on the face and neck where such combination treatment is indicated. In this regard, one or more removable ice packs can be secured to head and neck area device to suitably apply cold therapy to one or more areas on the patient.

When in use for a post-operative recovery, head and neck area LLLT treatment device is securable around the head of patients with an illuminatible patient side proximally situated at or near one or more areas indicated for at least LLLT treatment, including, but not limited to but not limited to the face, neck, tooth, gum, jaw, tonsillectomy or temporomandibular joint (TMJ). When the head and neck area device is suitably situated on patient, at least one PBM control module will activate at least one light source in operational and optical engagement with an engagement port on the PBM control module in communication with at least one light guide/light guide arrangement. The patient areas in need of LLLT treatment can be illuminated with light having in the spectrum of about 630 nm to about 1000 nm, for example.

In an exemplary treatment protocol, instructions can be configured to generate a first LLLT treatment protocol whereby light from the at least one light source at a wavelength of 650 nm at 60 mW, in a continuous wave for about 120 seconds and including a pulsing mode of about 15 or about 30 or about 60 or about 90 or about 120 seconds of pulsing at each of 4 Hz, 10 Hz, 60 Hz and 1000 Hz, or variations thereof. The PBM control module can direct the first treatment protocol to be repeated from time to time, for example, every 15, 30 60, 120 or 240 minutes, with an off cycle in between each cycle. Based on the postoperative days, the number of cycles can be repeated per the need of energy density and total energy level and optimized to each skin type to provide a LLLT treatment protocol for a patient in need of treatment thereof.

In some aspects, a first covering material can form a second side that is away from the patient facing side. The first covering material can be cushioned or the like to improve patient comfort. The patient facing side can comprise a material that allows LLLT to be emitted therefrom. The at least one light guide or light guide arrangement can be incorporated between a light transmitting material and the covering material, optionally with an absorbent material interspersed therein, as discussed in more detail in the Figures hereinafter. The LLLT treatment dosage applied to the relevant patient areas can then be delivered from the patient facing side.

When the LLLT delivery element is configured in the form of a garment or bandage, to allow LLLT to reach a wound in need of treatment, as well as any areas associated with healing of the wound, material that covers the wound or associated body area can be light diffusing, such as a non-woven material. Typically, a suitable non-woven fabric can be a polypropylene-based material. The light diffusing material can comprise a sheet or web structure bonded (e.g., via mechanical, thermal or chemical bonding) together by entangling fibers or filaments. Film perforation can also be used. In further aspects, the wound-contacting material that is light diffusing can also comprise woven fibers, foams/sponges, and the like.

Alternatively, the LLLT delivery can be integrated into the garment or bandage itself, whereby the integrated garment optionally incorporates a absorbent material (e.g., gauze, sponge, etc.) and any covering material. In this regard, the at least one light guide or light guide arrangement can be associated with the PBM control module via the light guide engagement port(s) to allow the garment to be regularly changed and disposed of, but also to allow reuse of the operational components of the PBM control module. The prescribed LLLT dosage may be continued without interruption when a new, that is, fresh, garment/bandage comprising a suitable light guide configuration is placed on the patient, and the light guide(s) associated with the garment/bandage are engaged with the PMB control module(s). In other configurations, the garment/light guide or light guide arrangement combination is itself absorbent.

When configured in the form of a bandage or garment for wound treatment, the LLLT treatment devices substantially do not form an air-tight seal to the wound. Still further, during LLLT treatment with the devices of the present invention, the wound undergoing treatment is exposed to air during treatment thereof.

Still further, the LLLT delivery element can comprise an insertable device that incorporates at least one light guide in operable engagement with the PBM control module. Again, the PBM control module can be configured to be interchangable with any of the brace, bandage, garment and the insertable form of the LLLT delivery element. The insertable devices can be comprised of medical grade plastic.

The inventor herein has determined that application of light therapy, such as LLLT, can enhance healing of wounds in the vaginal cavity and vulvar regions, such as is relevant during male to female sex reassignment, while also being effective in reducing post-operative pain and inflammation. Yet further, the present invention can be utilized to enhance blood flow in female genital tissue, both within the vaginal cavity and in and around the vulvar region. As such, the inventor herein has further determined that LLLT can be effective in "vaginal rejuvenation," as well as in addressing infections or post-birth injuries to the vulva or vaginal region that can occur, such as in some vaginal deliveries. Areas proximal to the female genitalia, such as the bladder and the anal area can also be therapeutically treated with light therapy according to the devices and methods herein.

In a significant aspect, the LLLT devices of the present invention are configurable to be wearable by a patient within the vaginal cavity and/or in the vulvar region, as well as areas proximal thereto, in a patient in need of treatment, and the LLLT can be applied with such devices over an extended period, as directed by a medical provider. Such wearability has been found by the inventor herein to improve treatment compliance and enhance the efficacy of light therapy in a patient in need of treatment over prior LLLT delivery methods to the female genital region, when such LLLT is applied in accordance with in conjunction with one or more treatment parameters described herein.

The inventive LLLT devices comprise at least one low level light source in operational engagement with at least one light guide configured to deliver a therapeutic amount of LLLT substantially proximal to one or more locations at or near to the female genital area (whether naturally occurring female genitalia or reconstructed as in a male to female sex reassignment surgery) in a patient in need of treatment and, optionally, any areas associated with healing of the surgical wounds or in tissue regeneration.

A variety of light wavelengths can be appropriate for LLLT female genital area treatments herein. Generally, light in the ultraviolet, various visible ranges, and infrared light are each, individually, indicated for treatment of a wound, injury or medical indication at certain stages and associated healing areas. Accordingly, at least one aspect of the invention herein comprises selection of at least one light wavelength range appropriate for treating of a female genital area wound or female genital area condition in need of treatment.

Various effective wavelengths of light associated with wound healing have been reported at generally being effective between wavelengths of about 600 to about 900 nm (see e.g., FIG. 17 of U.S. Pat. No. 8,784,462, the disclosure of which is incorporated herewith in its entirety by this reference). The specific wavelengths identified as most effective for healing were reported to be 620, 680, 760, and 820 nm. Blue light in the spectrum range of from about 450 to about 495 nm is known to be effective for disinfection. Since wound disinfection is also relevant to wound healing, light in this nm range is also contemplated with the LLLT genital area devices and methods of the present invention. Wavelengths in the UV spectrum can also be effective in disinfecting a wound when signs of infection is detected or confirmed by the healthcare provider. The various wavelengths can be generated by a light source as would be known to one of ordinary skill in the art or can be determined through use of the inventive devices herein without undue experimentation by one of ordinary skill in the art.

In significant aspects, the inventive female genital area LLLT delivery device can comprise an insertable device configured to fit in the vaginal cavity where the device is substantially comprised of optically clear polymeric material, such as silicone, acrylic, or polycarbonate. Such medical grade materials are "hypoallergenic." Optical clarity allows light of desired wavelength(s) and dosage(s) to travel from a light source in and through the device by way of one or more light guides or light guide arrangements for transmission to the vaginal cavity area for LLLT treatment thereof. "Optically clear" means that substantially all of the light emitted from the at least one light guide or light guide arrangement is then transmitted out of the surface of the therapeutic device. This means that there is substantially no loss or low loss of light as emitted from the at least one light guide or light guide arrangement into the interior of the vaginal insert so as to allow delivery of light having sufficient energy to provide a therapeutic effect to the patient's vaginal cavity and areas proximal thereto.

In some aspects of the invention, at least one light scattering layer can be created on the surface of the transparent core or an additional material can be embedded in the vaginal insert to enhance light diffusion. Such "discontinuities" are described in more detail hereinafter in relation to the Figures.

The size of the vaginal insert can be varied depending on the physical parameters of the patient being treated. The provider can measure, either subjectively or objectively, the approximate size of the patient's vaginal cavity. The provider will select the vaginal insert as sized for the patient being treated with LLLT.

As would be recognized, the outer surface of the vaginal cavity insert should be substantially approximate to the dimensions of the reconstructed vaginal cavity in a sex reassignment or the dimensions of the cisgender patient's vaginal cavity for use in a rejuvenation treatment or other suitable indications.

For a reconstructed vagina in a sex reassignment procedure, also called a "neovagina," the overall length of the vaginal insert may have a smaller variation than that of a cisgender female because the vaginal cavity is being constructed from surgical norms. This is due to the limitations of the male body parts that are used to create the reconstructed vagina. In this regard, the depth of a typical neovagina created from male to female sex reassignment surgery is generally be between about 11 and 12 cm, as provided by the parameters of Dennovilliers' fascia, from which the neovagina is partially constructed. This is within the range of the natural female vagina.

For a cisgender female, the range of vaginal cavities may be greater. A 1996 study of the vaginas of 39 Caucasian women, found the following ranges of dimensions: lengths: 6.9 to 15 cm; widths: 4.8 to 6.3 cm; and introital diameters: 2.4 to 6.5 cm. A 2003 study, measured vaginal surface areas ranging from 66 to 107 $cm^2$ with a mean of 87 $cm^2$ and a standard deviation of 7.8 $cm^2$. Research published in 2006 gave the following mean dimensions, based on MRI scans of 28 women: mean length from cervix to introitus: 6.3 cm, and mean width: at the proximal vagina: 3.3 cm; at the pelvic diaphragm: 2.7 cm; and at the introitus: 2.6 cm. Thus, it can be observed that there is a potential for wide variation in the vaginal cavities of the cis gender females being treated.

Accordingly, the vaginal insert may be provided in a variety of lengths of from about 4 cm to about 15 cm and the diameter at the widest point can be from about 2 cm to about 10 cm. The shape of the vaginal insert can generally be cylindrical. For comfort, the interior end can be rounded. The insert can generally have a tapered configuration, as indicated by the general shape of a natural vaginal cavity, that is, wider at the anterior end (i.e., the part of the vaginal insert proximal to the vaginal opening), with a gradual reduction in the vaginal insert diameter moving toward the interior end (i.e., the part of the vaginal insert that is proximal to the internal end of the vagina, which would be the cervix in a cisgender woman, but would be absent in a male to female sex reassignment patient).

An advantage of the present invention is the wearability, comfort, safety and conformability to the treated vaginal cavity area. Moreover, treatment times, including dilation without applied light therapy, can be extended and/or made more convenient. The patient experiences enhanced wearability during treatment because the self-contained, that is, on board power, controller, light source(s), and, optionally, sensors allow concealment of the device during use and thus, enhanced privacy and comfort.

Application of LLLT treatment to the vaginal cavity via an insertable device that is wearable by the patient for an extended period, can improve the healing process during the phases of wound healing. Treatment compliance can also be enhanced. To facilitate removal and insertion, the vaginal insert can incorporate a rim or tab integrally formed with the vaginal insert proximate to the anterior end thereof. The rim is sized and shaped to be comfortable for the patient, but to still enable the use thereof. To this end, the inventor herein has found that the rim or tab can be generally shaped as a teardrop, which has been found to comprise a balance between function and comfort for the patient. However, the size and shape of the rim and tab can be varied, or even not included on the vaginal insert, without departing from the scope and content of the invention. In some aspects, at least some of an anterior end of the vaginal insert can be situated outside the vaginal cavity. In some aspects, the controller and associated light guide(s) or light guide arrangement(s) can be located within the structure of the vaginal insert, that is integrated within the vaginal insert itself, such as at or near the anterior end thereof. In other aspects, the controller and associated light guides or light guide arrangements can be present as a separate set of componentry for engagement with the vaginal insert.

In the case of rejuvenation or enhancing the internal structure of the vaginal cavity, the inventive LLLT devices and methods can enhance the effectiveness of such therapies by the applied LLLT stimulating the tissue, and thus growth of new, more elastic tissue, thereby tightening and enhancing feeling in the vaginal cavity area of a woman in need of treatment. Such treatment can also enhance the function of the female bladder by increasing muscle tone of areas proximal thereto.

Moreover, LLLT/dilation combination therapy used in conjunction with a light therapy delivery liner can substantially improve the long-term outcomes of internal and external structures of a reconstructed external female genital area (i.e., the vulvar area), by enhancing wound healing over prior art methodologies. Use of the light therapy delivery liner can improve wound healing of the vulvar region when used alone, such as would be indicated with an episiotomy, for example. Extended lengths for the light therapy delivery liner can allow treatment of hemorrhoids along with the vulvar areas, or hemorrhoids can be treated without attendant treatment of the vulvar areas. Moreover, LLLT light therapy applied both internally and externally to the vulvar regions can also be useful to treat vaginal fungal infections, and the methods and devices of the present invention also incorporate this treatment modality.

The light therapy delivery liner can be sized and shaped for the comfort of the patient. In this regard, the liner can generally be narrower at the front end (i.e., the area proximal to the clitoral area of the female genitalia) and wider at the back end. The corners are optimally rounded, again to enhance comfort. The shape can also approximate that of a panty liner or sanitary pad, as appropriate. To accommodate the various sizes of patients who will be treated with LLLT provided from the liner, the delivery liner can be provided in a variety of sizes. Generally, the length can be from about 20 to about 35 cm and the width can be from about 8 to about 16 cm at the widest end (i.e., in the area proximal to the rectum) and about 1 to about 10 cm at the narrowest part (i.e., in the area proximal to the clitoral area). If additional areas of the external female genitalia are being treated, the size and shape of the liner can be modified to enhance comfort. Soft and flexible materials should be used, such as silicone that has a Shore hardness of from about 0 to about 30, or from 15 to about 25.

The light therapy delivery liner can incorporate an indentation sized and shaped to allow the anterior end of the vaginal insert to engage therein. When a patient is wearing both the vaginal insert and the liner simultaneously, such engageable fit can improve comfort and wearability, especially when the liner is kept in place by well-fitting undergarments.

The at least one (or one or more) light guides or light guide arrangements can be configured to enhance patient comfort, and thus wearability and patient compliance. In this regard, the at least one light guide or light guide arrangement is configured proximal to the anterior end of the vaginal insert, whereby the at least one light guide or light guide arrangement entry into the vaginal insert is at a position on the vaginal insert that is external to the vaginal cavity when the vaginal insert is in the patient's vaginal cavity. To further enhance patient comfort, the surface of the vaginal insert is substantially smooth.

One or more optical guides are utilized with the light therapy delivery liner. The optical guides are engaged with the liner to enhance wearability and patient comfort. In this regard, the optical guides can be engaged with the liner at a front or a back end.

It has been found by the inventor herein that LLLT treatment effectiveness for both male to female sex reassignment, vaginal rejuvenation, as well as other therapeutic effects can be improved when the therapeutic light is emitted from the vaginal insert and/or as generated from a light source that can provide a known and/or regulated dosage, as opposed to being provided from one or more light sources that do not provide a known and/or regulated dosage of light. Therefore, the present invention comprises an insert and/or liner from which LLLT is provided in a known or regulated dosage amount, such as by a dosed light source.

The wavelength(s) of light applied to the female genital regions in need of treatment (that is vaginal cavity and/or vulvar areas and, optionally, areas proximal to these areas) can be the same or different from the wavelength(s) of light applied to areas proximal to areas that are associated with enhancement of wound healing of the genitalia. If the wavelengths applied to the different areas are the same, a single light guide or light guide arrangement can be configured to emit light proximal to the wound and the additional area(s). If the applied wavelengths are different, it can be beneficial to deliver the respective wavelengths with two different light guides. One or more light sources can be used to deliver the singular or multiple wavelengths through one or more light guides or light guide arrangements.

In further aspects, light reflected or emitted from vaginal cavity tissues while the vaginal insert device is inserted therein can be collected in one or more light guides or light guide arrangements operationally engaged with the vaginal insert for evaluation of such reflected or emitted light in a suitable sensor associated with the controller, such as photodetector with optical filters for desired wavelengths or the like. For example, it is known that during healing wounds may reflect or emit light in different wavelengths that can indicate the phases of healing. Further, wounds that are not healing correctly can reflect or emit light in wavelengths that can provide information about such inadequate healing progress or presence of infection. The inventions herein can be configured to allow such reflected or emitted light to be collected in one or more light guides or light guide arrangements in operational engagement with an evaluation device suitable for measuring the wavelength of light so reflected or emitted. Such detected light energy from the wound during healing can provide timely and accurate information and can be utilized to determine the healing progress of any wound healing, including in the female genital area undergoing treatment with the LLLT treatment devices herein. If the reflected or emitted light and associated evaluation thereof indicates that healing is occurring faster or slower than expected, the LLLT dosages can be timely modified, or the treatment stopped if appropriate. Such sensor data and measurement of healing progress can be desirable in near-real time monitoring the healing progress within a vaginal cavity because the patient may be highly sensitive during healing, and timely adjustment of treatment may reduce pain while the patient is being treated at home before a thorough in-office patient evaluation by a medical provider. Light reflected or emitted from the vulvar regions can also be evaluated, although it will be easier for a provider to visually evaluate the healing progress of such external genital areas.

In a further aspect, LLLT treatment devices for nasal and/or sinus indications are provided, such as a rhinoplasty or sinus-area surgeries, such as septoplasty, rhinoplasty, and tonsillectomy etc. When therapeutic levels of LLLT are delivered to affected tissues, post-operative recovery of many surgical procedures in and around the nose can be enhanced.

In this regard, a nasal insert that suitably delivers LLLT treatment to the interior of the nose (e.g., nasal and, optionally, areas proximal thereto). The nasal insert has an outer diameter that comprises a light delivery area and, as such, comprises a "light guide arrangement" as discussed elsewhere herein. The nasal insert can also comprise an inner diameter that is configured to allow air to travel therein to enhance patient comfort post-procedure. The nasal insert is removably engageable with a PBM control module. When engaged with the PBM control module, LLLT is delivered to the interior of the nose. It can be beneficial to mount the PBM control module in a location away from the patient's face. Accordingly, the PBM control module can be engaged with a first light transmission portion that is flexible and allows LLLT to be transmitted with minimal loss. This can be accomplished with a fiber optic as a first light transmission portion. The fiber optic can be operationally and optically engageable with a light guide arrangement, or second light transmission portion, that is suitably configured to be delivered to the interior of a patient's nose. To reduce patient discomfort associated with engagement and disengagement of the fiber optic from the nasal insert, a magnetized connection can be used, as described further herein in the Figures.

The nasal insert can be used in conjunction with a support that is configured to cover the patient's nose. This support can be shaped to provide support to the bridge of the nose. LLLT treatment can be delivered to a patient facing side of the support from a suitably configured light guide arrangement. A fiber optic can be used to deliver LLLT effectively and efficiently from the PBM control module to the light guide arrangement.

Due to the anti-inflammatory properties of red and NIR light, when LLLT treatment is supplied to the affected patient areas immediately post-surgery, post-operative swelling will be minimized and breathing through the nose will be made possible. This LLLT treatment will also be helpful to alleviate the nasal congestion caused by swelling tissue inside the nasal cavity but constrained by the bone structure around it, potentially reducing tissue necrosis and improve success rate and comfort for the patients. Light energy has also been documented to accelerate the healing of surgical wound and shortening recovery time. LLLT treatment can also provide analgesic effect, relieving pain after a surgery.

In a still further aspect, the insertable LLLT element can comprise a device to aid healing after oral surgery, such as the upper or lower areas of the mouth. The invention further comprises devices and methods for treatment of mouth areas after procedures such as tonsillectomy, in conjunction with orthodontic procedures, bone grafts, dental implants, gingivitis correction, and other mouth area procedures. In this regard, one or two mouthpieces can be configured to deliver LLLT from at least one PBM control module, via suitable light transmission portions, such as fiber optics and/or suitable light guides/light guide arrangements. Such light transmission portion is operationally and optically engaged with each of the upper or lower mouthpieces, which are optically transmissive, and having Shore A Hardness of about 20 to about 95.

In some aspects, the mouthpieces can be configured to fit over the teeth or palate, with or without coverage of the all or part of the upper teeth. In a further aspect, the mouthpiece can be configured to fit over the lower teeth. In either case, LLLT treatment can be delivered to proximally to the mouth area from the light transmissive portion of the mouthpiece. Reflective material can be incorporated in an interior portion of the mouthpiece to enhance light delivery. Discontinuities can also be incorporated to enhance light scattering and diffusion as discussed elsewhere herein.

A softer material, between Shore A hardness of about 20 to about 80 can be used to fabricate mouthpieces having grooves, to facilitate fitting onto the teeth. On the other hand, harder materials, such as those in the Shore D hardness range of about 70 to about 95 can be more suitable for clear and less visible braces, which are designed to have a grove(s) that fit tightly to the teeth for orthodontal alignments.

LLLT mouth device configurations can be optimized to treat various conditions. For example, when an entire mouthpiece surface is configured to transmit light delivered from a PBM control module, the mouthpiece can function as clear braces to enhance correction of the teeth position. Upper and lower mouthpieces can be configured to allow light to be delivered from a single PBM control module. When red light is applied to the mouth interior at from about 640 nm to about 670 nm dosed at about 0.2 to about 1 $J/cm^2/day$, LLLT can speed up teeth movement as well as reduce the pain and discomfort from wearing the brace. Still further, LLLT treatment can reduce the pain and swelling after surgeries to the uvula, tonsil and palate. LLLT treatment can reduce the pain and swelling after surgeries to the gum, or as ongoing treatment to gingivitis.

In a further method of LLLT treatment according to the invention herein, the light guides can be arranged to deliver light substantially proximally to the areas associated with healing of an incision, but where the incision is not readily reachable by the light guides or light guide arrangements, notwithstanding their flexibility. One example of such a treatment modality is for removal of third molars (wisdom teeth) where the incisions should remain substantially untouched and where it would often be difficult to comfortably fit a treatment device to the interior of a patient's mouth. LLLT treatment can be applied extra-orally, proximally to the patient's face proximally to the sites where the third molars have been removed, and further to the lymph and carotid areas in the patient's neck area to provide stimulation of those areas to enhance healing, reduce pain and swelling.

In addition to providing LLLT treatment of wounds, the wearable/portable LLLT treatment devices and methods of the present invention can be used to treat skin conditions, such as psoriasis, fungal infections etc. As disclosed in US Patent Application No. 20070208395, the disclosure of which is herein incorporated by reference in its entirety, the appropriate wavelength to treat psoriasis is from about 300 nm to about 320 nm. Fungal infections are typically treated using wavelengths of about 255 to about 320 nm. The devices and methods of the present invention can also incorporate light sources that generate LLLT in these ultraviolet ranges, especially UV-C from a PBM control module equipped with an appropriate light source.

Yet further, LLLT has been shown to be effective in anti-aging treatments. In this regard, the LLLT has been shown to increase cell regeneration, such as to slow or even reverse the effects of photoaging. Such anti-aging LLLT is disclosed in U.S. Pat. No. 9,144,690, the disclosure of which is incorporated herein in its entirety by this reference. In some aspects, the LLLT delivery element for anti-aging processes, as well as acne treatment, can be in the form of a plastic mask with a Shore A hardness of about 0 to about 10 and reflectively coated on the side facing away from the face, wherein the at least one light guide or light guide arrangement is arranged proximal to the patient's facial areas. The present invention can employ light at from about 800 to about 900 nm range for treatment "around the eye".

Yet further, the devices and methods of the present invention can be used to treat medical indications in the head and neck area with lymph node clusters and typical lymph drain in the face and mouth. For oral maxillofacial surgeries, the lymph drains from the teeth, gum, pallet of a patient's mouth area and travels to a lymph cluster in the neck region. By illuminating the areas of lymph nodes, the flow of lymph fluid can be enhanced to reduce swelling and improve healing.

In addition to application of a therapeutic amounts of LLLT in an area substantially proximally to a wound or other medical indication in need of treatment—which can be termed "a first treatment modality"—in some aspects, the devices of the present invention further incorporate light treatment of areas on the patient that are in locations on the patient that are not the actual wound area, or a "second treatment modality." In this regard, the delivery element can further include LLLT in areas associated with healing of the wound area, such as blood vessels, lymph nodes, nerves or acupuncture pressure points. Such areas can be those areas of the patient that are therapeutically associated with healing functions of the incision.

The wavelengths of light applied proximally in the first treatment modality can be the same or different from the wavelengths of light applied to areas associated with the second treatment modality. Areas suitable for treatment in a second treatment modality can comprise one or more lymph areas and/or one or more blood vessel areas on the patient. If the wavelengths applied for the first and second treatment modalities are the same, a single light guide/light guide arrangement can be configured to emit light proximally to both the areas of treatment for the first and second treatment modalities, where the light guide or light guide arrangement is operationally engaged with the PBM control module as disclosed elsewhere herein. If the wavelengths applied in the first and second treatment modalities are different, the light can be provided from separate light guides/light guide arrangement, where each light guide/light guide arrangement is operationally engaged with the PBM control module as discussed elsewhere herein.

In addition to application of a therapeutic amounts of LLLT in an area substantially proximal to the internal and/or external wounds or conditions in need of treatment, in some aspects, the devices of the present invention further incorporate light treatment of patient areas that are in locations on the patient that are not the actual wound area. In this regard, the LLLT delivery element can further include application of LLLT in "healing vital areas," that is, areas associated with healing of the wound area, such as blood vessels, lymph nodes, nerves or acupuncture pressure points. Such areas can be those on the patient that are therapeutically associated with wound healing functions or tissue regeneration in the female genital regions.

Yet further, the LLLT delivery device can incorporate additional LLLT in a location away from the wound area where the additional LLLT is provided at an area proximal to those one or more areas of the patient that are associated with increasing blood flow to the area proximal to the wound or desired tissue regeneration. It is known that infrared and red light beams will penetrate to various depths, depending on wavelength (for example, the 830 nm wavelength will penetrate to a depth of nearly 5 cm). The laser beam at a low power (under 200 mW or so) will not noticeably heat the soft tissue that it reaches, even with continuous use. When the beam hits the cells that line small arterioles, nitric oxide (a vasodilator) is released, thereby increasing local blood flow. Additionally, the laser will "desensitize" local nociceptors, thereby decreasing or even eliminating pain at the site. There is also evidence that light therapy can decrease inflammation, especially chronic inflammation. Similar results have been found with use of LEDs in various studies, as discussed previously.

For example, when treating a patient after a total knee arthroplasty, the groin area with blood vessels to and lymphatic nodes/ducts that drains from the knee area after surgery can be treated with LLLT substantially simultaneously with an application of a LLLT treatment of the area substantially proximal to the wound area. As such, in a non-limiting example, the light delivery element, for example, a knee brace or bandage configured with one or more flexible light guides/light guide arrangements substantially conformable to the knee incision area can also incorporate LLLT treatment delivered from light guide(s) or light guide arrangement(s) operationally and optically engaged with a PBM control module configurable to provide LLLT treatment of the same or a different wavelength in an area substantially proximal to the lymphatic system located in a lymph drainage location from the wound site, as well as blood vessel areas associated with the knee and incision area.

For facial surgery, the LLLT treatment device can include an aspect that is configured in an area proximal to the neck area with blood vessels to the facial tissues and superficial lymph nodes that receive lymph drain from most of the facial tissues.

For surgeries to the pectoral region and the breasts, including surgeries to the shoulders and the arms, it has been found that in addition to apply LLLT treatment to the incision and tissues proximal thereto as a first treatment modality, irradiation of the entire pectoral area and the arm pit can significantly reduce pain, swelling while improve healing time as a second treatment modality.

Different patients may react differently to light therapy, such that a particular light therapy dose may be more effective for one patient than for another. This between-patient variability can be substantial. For this reason, in some aspects, basing a light therapy dosage on the patient's observed initial condition may not result in optimum dosing for any one particular patient. In some aspects, the variability of a particular patient's response to light therapy may be small in comparison to the between-patient variability. Aspects of the present invention therefore further comprise one or more monitoring events during a scheduled treatment regime, wherein after application of a selected LLLT treatment for a patient, a provider can observe the healing (or lack thereof) of the patient's wound or other medical indication, and, optionally, make an adjustment of the applied LLLT treatment dosage in response to an observation in real time. Such in-treatment observation can be made remotely with the aid of the data from sensors and/or imaging devices associated with a PBM control module and that may be incorporated in associated devices, thus allowing a dosage modification to be provided substantially timely without need for the patient to visit a provider's office. In this regard, a dosage can be calculated based not only on the patient's initial indicated dosage, but also on the patient's prior responses to light therapy doses.

When a patient is prescribed a LLLT treatment by a medical provider, an initial dosage and treatment time is defined by the medical provider. The appropriate LLLT treatment device configuration (e.g., brace, garment, bandage, insertable element) is provided to the patient, such as by the provider or a pharmacist. In some implementations, all or part of the LLLT treatment device can be purchased by the patient in an "over the counter" environment, which can be either physically or electronically virtual. In additional implementations, the LLLT treatment devices are provided to the patients at no or substantially reduced cost, with the definition and administration of a treatment dosage provided to a patient when the patient fills a digital "prescription" from a provider, the "light medicine" in the form of data or software instructions are deliverable to the device. In this regard, once a person receives a LLLT treatment device for use with the "prescription" over the counter, the person can be required to register the device via an app or online prior to the device being activatable for use. For example, the person can be provided with a code to generated by the device in response to a Bluetooth® signal, where that code is input into the online registration program. In accordance with this registration and authorization, the person can be required to answer a plurality of questions associated with the data for "prescribing" of an appropriate therapy and dosage for that patient. When a light therapy prescription is filled, the provision module can transmit the "photonic medicine" to the PBM control module associated with that patient via software instructions that include operational parameters for patient LLLT treatment and dosage appropriate for the patient as defined by the patient's input. Existing treatment programs already stored in the memory on the PBM control module can be operated via a set of parameters assigned to the specific patient by the medical provider, including one or more of the wavelength or wavelengths, wavelength ranges, pulsing frequency, light output power, intra-day sessions, length of treatment session time, session irradiation time, intra-session intermission time, treatment days, total session numbers, total treatment days, total irradiation time, time-course and variation between sessions, as well as sensor activation instructions, among other information. Alternatively, the software instructions can include both a new program and operational data to the PBM control module. The dosage can also be modified from time to time if the patient provides further input as the treatment progresses.

At the expected end of a treatment period, the components of the device can be deactivated from use so as to prevent reuse of the LLLT treatment device without proper device and patient management of a patient by a provider. Reactivation of the device can only occur if the person reengages with the app or the online registration program, so as to provide updated medical conditions. At the end of any treatment, the PBM control module can store and/or transmit to a remote device all information, including data and images from sensors, treatment progress input, patient profile data, as well as the prescribed treatment details in a data warehouse for further analysis with machine learning and artificial intelligence to improve human light therapy knowledge and understanding.

In some aspects, the data communication system associated with the LLLT treatment device for transmitting data to and from the light therapy device comprises a wireless data communication system that includes LTE, WiFi, or Bluetooth®-enabled transceiver. In significant aspects, the LLLT treatment device of the present invention substantially does not require the patient to be stationary during treatment, as is necessary with conventional light therapy devices, such as handheld light treatments, light boxes or the like. To the contrary, the LLLT treatment devices of the present invention are fully wearable and portable in accordance with being battery powered.

To ensure that communications transferred to and from the componentry, the provider, etc. are secure and substantially free from a risk of "hacking," data related to the patient and her treatment etc. can be encrypted using use secure communications (encryption, etc.), such as VPN, IPSec, SSH (Secure Shell), SSL (Secure Sockets Layer), etc. Such features are enhancements over standard Internet security for the LLLT treatment devices, methods and systems of the present invention.

The wearable LLLT treatment device is configurable to dispense one or more therapeutic dosages of LLLT treatment to a patient in need of such treatment, whereby the generated dosage of LLLT is defined or approved by a provider prior to and, optionally, during a treatment. In this regard, the amount of LLLT treatment appropriate to provide a therapeutic dosage as indicated by selection of one or more wounds or physiological condition present in the patient. The LLLT treatment device of the present invention is configurable to allow a provider to monitor and, optionally, to modify the delivery of one or more individual LLLT treatments in a total LLLT treatment regimen and, in some aspects, the treatment results via communications capability as discussed in detail herein.

Even among surgeries to the same body area part, specific types of surgical interventions may be markedly different in terms of recovery time. This differentiation between expected recovery times, and thus the applicable time for the LLLT treatment of the present invention can vary because of, at least in part, of the amount of trauma experienced by the patient in the surgery. For example, recovery time from breast surgery may be affected by whether the surgery is reconstruction after mastectomy, augmentation, breast reduction. Reconstruction after mastectomy may require additional recovery time due to extensiveness from prior surgery(ies), and muscle flaps donor sites, which can be either the transverse rectus abdominis myocutaneous flap from the abdomen or the latissimus dorsi muscle flap from the back based on each patient's condition. The postoperative LLLT treatment appropriate for recovery can be significantly different, both in terms of treatment delivery element, wavelength, and dosage. Even though breast augmentation ostensibly appears to be similar to breast reconstruction because an implant is placed in the patient's chest area, her recovery time may be considerably different than breast reconstruction surgeries. Breast reduction may have an even different recovery time due to the variation in the incision type, size, removal of native tissue, etc. Thus, a further aspect of the devices and methods of the present invention can be the selection and/or identification of a sub-category of a surgery-type. So, provider prescribing or approval of LLLT treatments after surgery can be an aspect of the invention.

The course of healing of a wound or other physical malady in a patient may also vary within a patient regimen. For example, as a wound heals, such as with a surgical incision, four stages of healing are present and follow four processes: hemostasis, inflammation, proliferation and maturation. Also, the four phases are recognized to be different molecular-biologically, some phases can occur with overlapping in time. For example, on post-op day after a Cesarean delivery, while some tissue on the abdominal skin the might be substantially through the hemostasis phase and to start the inflammation phase, whereas other tissue such as the wound on the uterus may still be in the hemostasis phase.

As would be recognized, hemostasis is the process of the wound being closed by clotting. Even though the action of hemostasis happens very quickly, a patient may experience this phase as long as three days after an extensive surgery and for which PBM provision module or a provider may consider when prescribing LLLT treatment. In this regard, light wavelengths in the visible red spectrum of from about 650 nm to about 1,000 nm can be beneficial when delivered at dosages of from about 2 to about 5 Joule/cm$^2$ per day for the first about 48 hours depending on the areas of the body to reduce the occurrence of bruising and swelling. For example, if a patient with skin color type II on a Fitzpatrick scale with an incision wound of about 35 centimeters long around the upper portion of the face, such as after a rhytidectomy, or facelift, which also has a large amount of mobilized tissue dressing on post-op day and post-op day 1, and on post-op day 2 and 3, exudates and absorbent dressing. A prescription with a combination of about 650 nm and about 810 nm at about 3 J/cm$^2$ on post-op day 1, 2 J/cm$^2$ on post-op day 2 can be used during the hemostasis phase while transitioning into inflammatory phase. In the event the sensors associated with a PBM control module detect a higher level of bruising presence, treatment provisional system may recommend a modified prescription to increase the amount dose to 2.5 J/cm$^2$ on post-op day 2 to be approved by provider.

With the latter three stages—inflammation, proliferation and maturation—LLLT treatment can enhance wound healing. Notably, however, the physiological process for each of these stages are different. Thus, in some aspects, LLLT treatment of the present invention can be varied in treatment parameters as healing progresses in an individual patient. In this regard, the LLLT of the present invention can be defined in accordance with the expected length of each of the stages of wound healing. Put another way, the LLLT treatment protocol can be selected, observed, modified, managed and/or tuned to account for at least one, or two, or three stages of wound healing, or for any other relevant parameters. In one respect, therefore, the present invention comprises identification of a wound treatment phase, based on sensor data, image or patient input and application of an appropriate wavelength(s) of light, and dose to optimize, enhance or augment healing of the wound during that phase.

Inflammation begins right after the injury when the injured blood vessels leak transudate (made of water, salt, and protein) causing localized swelling. Inflammation both controls bleeding and prevents infection. The fluid engorgement allows healing and repair cells to move to the site of the wound. During the inflammatory phase, damaged cells, pathogens, and bacteria are removed from the wound area. These white blood cells, growth factors, nutrients and enzymes create the swelling, heat, pain and redness commonly seen during this stage of wound healing. In some aspects, the LLLT treatment can be provided to be effective to enhance healing during the inflammation process. In this regard, light wavelengths in the visible red spectrum at from about 650 nm to about 900 nm can be beneficial when delivered at dosage of from about 1 to about 5 Joule/cm$^2$ per day for the first about 48 to about 72 hours depending on the areas of the body. For example, if a patient with skin color type II on a Fitzpatrick scale with a wound of about 30 centimeters long on the abdomen, such as after a Cesarean delivery, which has a large occlusive dressing on post-op day and post-op day 1, and on post-op day 2 and 3, exudates and absorbent dressing a LLLT treatment regimen having a combination of about 650 nm and about 810 nm at 5 J/cm$^2$ on post-op day 1, 4 J/cm$^2$ on post-op day 2 and 3 J/cm$^2$ on post-op day 3 can be used during the inflammatory phase. Higher dose may be recommended for the same wound for a patient with skin color type V on a Fitzpatrick scale.

Further, sensor data obtained from treatment can provide information about the level of exudate presence, which can be correlated to the progression of inflammatory phase. As a non-limiting example if sensors associated with the PBM control module provide information signaling the presence of a higher than normal amount exudate on post-op day 2, increase the amount of LLLT treatment to about 2.5 J/cm$^2$ on post-op day 3. the invention also is adjustable to incorporate parameters such as the size of the wound as well as the location of the wounds on the body during each phase of healing due to matters related to relevant tissue structure (e.g., thickness of dermis, subdermal fat, depth of incision, mobilized tissues, closure technique, affected organs, as well as other factors). As a non-limiting example, a patient with skin color type II on a Fitzpatrick scale could have four wounds of about 5 centimeters each near the eyes, such as after a blepharoplasty, on both the upper and lower eyelid. A prescription with 810 nm at 2 J/cm$^2$ on post-op day 1, 1.5 J/cm$^2$ on post-op day 2 and 1 J/cm$^2$ on post-op day 3 can be used during the inflammatory phase, or modifications of such dosage may be specifically indicated by the patient's individual condition.

The proliferative phase of wound healing occurs when the wound is rebuilt with new tissue made up of collagen and extracellular matrix. In the proliferative phase, the wound contracts as new tissues are built. In addition, a new network of blood vessels is constructed so that the granulation tissue can be healthy and receive sufficient oxygen and nutrients. Myofibroblasts cause the wound to contract by gripping the wound edges and pulling them together using a mechanism similar to that of smooth muscle cells. In some aspects, the LLLT treatment can be provided to be effective to enhance healing during the proliferation process, In this regard, light wavelengths in the visible red spectrum of from about 650 nm to about 900 nm can be beneficial when delivered at dosage of from about 0.1 to about 4 Joule/cm$^2$ per day for the proliferation phase depending on the nature of the wound and locations of the body. For example, the above mentioned patient with skin color type II on a Fitzpatrick scale with a wound of about 30 centimeters long on the abdomen after a Cesarean delivery, typically starting on post-op day 4 after discharge from the hospital, with possible exudates and absorbent dressing. A prescription with a combination of 25% energy from 650 nm and 75% energy from 810 nm at a combined 2 J/cm$^2$ on post-op day 4 to day 10. If the patient reports higher than normal pain will be kept at 3 J/cm$^2$ on post-op day 4 to day 10. Higher dose on 810 nm to increase the tissue penetration considering the depth of tissue to be affected. Further, sensor data from treatment device will report on the level of exudate presence and change in skin color from light reflection, which may be correlated to the healing progression and infection. As an non-limiting example, the PBM control module, can use generated sensor data indicating a higher than normal amount "pink" tissue on post-op day 4, after sending question to patient to confirm the sensor data validity, to recommend an additional or modified treatment amount, such as to generate LLLT application in the UV-C spectrum at from about 250 to about 270 nm with a dose to 1 mW/cm$^2$, for about 60 seconds twice daily starting on post-op day 5 for six days to the provider for approval. Once validation occurs as discussed elsewhere herein, the PBM control module receives and completes the new prescription via software instructions by incorporating regular monitoring by sensors and/or patient feedback.

The maturation phase (also called the "remodeling stage") occurs when collagen is remodeled from Type III to Type I and the wound fully closes. The cells that had been used to repair the wound but which are no longer needed are removed by apoptosis, or programmed cell death. When collagen is laid down during the proliferative phase, it is disorganized and the wound is thick. During the maturation phase, collagen is aligned along tension lines and water is reabsorbed so the collagen fibers can lie closer together and cross-linking. Depending on the wound type and area on the body, remodeling begins at about 21 days after an injury and can continue for a year or more. In some aspects, the LLLT of the present invention can be provided to be effective to enhance healing during the maturation phase of a wound healing process. In this regard, the invention also take consideration for size of the wound, patient scar history, patient skin type, age and other profile data as well as the location of the wounds on the body during the maturation phase of healing because of the tissue location and patient profile matters significantly during this phase, especially to minimize the development of abnormal scars, such as keloids and hypertrophic scars.

Studies have shown keloid scars occur in about 15 to about 20% of individuals with African, Asian or Latino ancestry. For LLLT treatment, as a non-limiting example, a patient with skin color type VI on a Fitzpatrick scale has a wound of about 5 centimeters on the chest. To provide the beneficial effect of wound healing while minimizing possible keloid, a prescription with visible 660 nm at 2 J/cm$^2$ on post-op day 10 to day 45. Adjustments may be made with sensor monitoring and patient reported information and images.

Still further, even amongst the same categories of wound or physical malady in need of treatment in a patient, patient variability can significantly affect recovery time. Failure to progress in the stages of wound healing can lead to chronic wounds. Physiological features that can progress to chronic wounds can include venous disease, infection, diabetes and metabolic deficiencies of the elderly. Moreover, the general physical condition of the patient prior to surgery can affect the rate that a patient will heal. For example, a patient who is more willing to engage in physical therapy may recover more quickly from joint replacement surgery (e.g., knee, hip, ankle etc.) than a person who is not. Such patients may be identified by weight, age, lifestyle (e.g., active, sedentary, etc.), other medical conditions (e.g., obesity, arthritis, depression, diabetes, etc.). A further aspect of the present invention can incorporate selection and/or identification of at least one patient specific (or personalized) patient condition prior to providing of a LLLT dosage to a patient in need of treatment, where information about such condition is incorporated into the LLLT treatment regimen provided to that patient.

In a further aspect, devices and methods of present invention can be used to treat hair loss and/or enhance hair growth in a patient in need thereof. In this regard, a LLLT treatment scalp area treatment device can comprise a cap or hat configured to incorporate LLLT treatment. The cap or hat is associated with a LLLT guide arrangement a PBM control module. The light guide arrangement can be permanently attached to the hat or cap or removably mounted therein. The PBM control module is mountable to the hat or cap, and can be removable for servicing. A concave side, patient facing side, of the light guide arrangement configurable to approximate the shape of a user's scalp area and a convex side, or cap/facing side, of the light guide arrangement is on a side opposite the scalp. The LLLT operational aspects can be configured to be substantially concealed in a baseball cap or a hat for discrete treatment and/or to contain the LLLT treatment within an area and/or to provide additional structure for the light guide arrangement and PBM control module. Alternatively, a light guide arrangement can be worn alone to provide therapeutic benefit. The light guide arrangement can also be placed inside a separate head covering as desired by the user.

For treatment, at least one light guide arrangement is in operational and optical engagement with at least one PBM control module configured with at least one light source that can emit light at from about 630 nanometers to about 1,000 nanometers, for example.

Blood supply to the scalp is believed to be one of the key factors for healthy hair growth. Traditional hats or caps, when worn with a tight band, reduce or cut off the blood supply by applying pressure to the six arteries to the top of scalp, which in term may worsen hair loss or reduce the effectiveness of hair loss treatments. The present invention, in some aspects, provides a design of hat or cap band that reduces pressure to areas with blood vessel and lessens the negative effect of tightly worn hat to the health of hair. The regions between the blood vessels in the scalp area have been found to be optimal areas of support to the hat or cap band. Cushioning can also be placed in one or more areas on the hat or cap band to reduce pressure on scalp area blood vessels. Additionally, the cap areas on the front of the head and on the back of head are also optimal areas of support to reduce overall pressure from wearing of the cap or hat.

Patient compliance to treatment for hair loss can be both critical and challenging because the hair growth takes a long time to be seen. Due to the small size of hair, hair growth is not easily noticeable until significant amount has been grown. A feedback system can be beneficial to allow users to monitor the progress of hair growth to encourage compliance at home. The present invention provides for a sensor or sensors associated with the LLLT scalp area device within the hat for easy and frequent monitoring of hair growth by consumers at home. An optional monitoring system can also include a componentry for: (1) capturing images included opening and scalp photograph, time stamp, (2) saving images; (3) analyzing the captured images for hair density; and (4) providing meaningful visual presentations from the analysis of captured images.

To enhance privacy for the patient, that is to make it less apparent that a person is wearing a hair growing device, the PBM control module can be fully or substantially concealed in the rim or along the interior of the hat. In this regard, the various components that together comprise the PBM control module is optically coupled to the light guide arrangement that can be configured to spread out over a larger surface of scalp area by comprising a flexible structure that is adjustable to the unique size and shape of a person's head.

Still further, light therapy has been shown to be effective for pain management. Many different pain modalities are treatable with the LLLT treatment devices of the present invention including, but not limited to, acute orthopedic conditions such as sprains, strains, post-surgical pain, a whiplash injury, muscular back pain, cervical or lumbar radiculopathy, tendinitis, and chronic conditions such as osteoarthritis, rheumatoid arthritis, frozen shoulder, neck and back pain, epicondylitis, carpal tunnel syndrome, tendinopathy, fibromyalgia, plantar fasciitis, post tibial fracture surgery and chronic regional pain syndrome are amenable to treatment with LLLT. Dental conditions producing pain such as orthodontic procedures, dentine hypersensitivity, and third molar surgery respond well to treatment with LLLT. Neuropathic pain conditions can also be treated such as post herpetic neuralgia, trigeminal neuralgia, and diabetic neuropathy. Generally, effectiveness of LLLT treatment for pain is provided by LLLT that is applied with light in the range of from about 650 to about 1,000 nm.

In a further aspect, the devices and methods of the present invention can incorporate selection of at least one patient-specific physical or medical parameter to be incorporated into the software instructions prior to or during administration of one or more LLLT. In this regard, the provider can input into a user interface (as discussed in more detail hereinafter) at least one of aspect of a patient's medical or physical condition, prior to the administration of a first LLLT dosage. For example, the provider (or the patient in some aspects) can input one or more of the patient's weight, age, physical condition (e.g., excellent, good, fair, poor etc.), medical history associated with wound healing (e.g., diabetes, anemia, keloid formation, skin tone and color, prior surgeries in relevant area that might indicate scarring etc.).

Sensors can be incorporated in or associated with the LLLT treatment devices to allow patient vital signs to be collected. In this regard, one or more sensors can provide real time or substantially real time measurement of one or more of a patient's heart rate, pulse, temperature, blood glucose reading, and the like. These one or more sensors can be incorporated on the LLLT delivery element or associable with the PBM control module(s), as discussed hereinafter. Alternatively, separately configured sensors can be in communications engagement with the LLLT treatment devices. In this regard, individual medical monitoring and treatment equipment associated with the patient can be associated with the communications capability of the LLLT treatment devices to enhance the data available for analysis of the progress and effectiveness of LLLT treatment. The data collection and transmission capability can enhance monitoring and management of such patient's medical condition in a medical telemetry environment.

In this regard, glucose monitoring capability can be associated with the LLLT treatment device, such as by placing a glucose monitor for the patient in communications engagement with the LLLT treatment device. If patient glucose level data transmitted to the provider can be relevant to indicate that the patient's healing is slower or faster than expected, the provider can adjust the LLLT dosage to obtain the desired rate of wound healing. Additionally, for patients with chronic wounds caused by diabetes, enhanced knowledge of how glucose levels over time may (or may not) affect wound healing and associated LLLT can enhance management of long term patient care.

Accelerometer data, such as that generated by a fitness device (e.g., FitBit® or the like) can be transmitted to the communications componentry of the LLLT. Accelerometer-containing sensor capability can also be incorporated into the LLLT treatment devices. As would be recognized, accelerometer data can be useful to monitor patient activity, which can provide useful information about the mobility of the patient which, in turn, can provide guidance to the provider about the response of the patient to the provided LLLT treatment. For example, and in a non-limiting example, patient mobility data transmitted to a provider remotely, such as by way of the communications capability of the LLLT treatment device, can provide objective information about the speed of healing of a patient receiving LLLT after surgery. If mobility data transmitted indicates that the patient's healing is slower or faster than expected, the provider can adjust the LLLT dosage to obtain the desired rate of wound healing.

In some respects, the PBM control module is engageable to wearable devices in addition to LLLT treatment, and such devices can be in communications engagement with patient treatment information. The communications engagement can be with a patient personal health record and/or a database of treatment information aggregated from a plurality of patients. In a non-limiting list, auxiliary devices can include ultrasound bone growth stimulators, radio frequency treatment device, TENS units, cold-therapy device, compression treatment device, and the like. Data obtained from such auxiliary devices can be utilized to generate a knowledge base that can be used to optimize treatment for a patient or group of patients for use in subsequent LLLT treatment applications.

The communications capability of the LLLT treatment devices of the present invention can also be configured to receive other collectable information that might be relevant to the effectiveness of patient wound healing. For example, information generated by a Wi-Fi enabled scale can be transmitted to the LLLT treatment device for transfer to a provider. Yet further, the patient's home or care facility conditions (cold, hot, humidity) as measurable by Wi-Fi enabled environmental sensors can be collected by the LLLT treatment device for transmission to the provider. In the case of a Wi-Fi enabled refrigerator, information can be collected for transmission to the provider to indicate whether the patient is obtaining the necessary nutrition needed to effect healing. Such capability can be especially relevant for homebound patients with chronic diseases, such as diabetes. As would be recognized, such chronic patients often experience associated chronic wounds that are slow to heal, or even that wholly fail to heal.

Still further, sensors can be incorporated with the LLLT treatment device to receive information generated from a wound during the LLLT treatment process. In this regard, sensors capable of reading a wavelength of light (both visible and non-visible light) can be configured with the devices. During treatment with LLLT, the wound may emit one or more wavelengths of light having characteristics with known association with the healing of the wound. For example, when a photo-sensor is equipped to detect the reflection of the same treatment red-light detectable near the connecting end of a light guide on post-operative day zero from a C-section wound dress over the incision will generate a reflection value A, which the Value A can be co-related to post-operative day. In addition, can be correlated to the standard known post-surgical care protocol (requiring a about 24 to about 48-hour occlusive dressing with a binder). When the dressing is removed on post-op day 2, a reflection value B, which has the combined reflection of the wound (with greater reflection) and the surrounding skin (with lesser reflection), can be detected with similar data correlation. On post-op 3, a reflection value C can be detected with similar components. As the wound heals, the average total reflection value trend can exhibit a decline over time, at a typical rate over the post-op recovery period. A slower decline may signal a delayed or sub-optimal wound healing.

A sudden increase in generated reflection value many therefore indicate infection. In another example, an embodiment of the invention is equipped with a photo-sensor capable of detecting the infrared light emitted from the incision and surrounding area. A data correction with post-op day, patient profile, and post-op care protocol can result in observable data trends. A change in trend might indicate events, including healing speed, infection, wound contraction, compliance, etc. In other embodiment, because the can skin reflects various wavelengths differently, other healing progress data can be collected with other light and sensor arrangements. In further embodiment, excitation light, such as blue or UV can be employed to detect bio-fluorescence from the tissue for healing analysis.

The duration of a total LLLT treatment using the devices and methods of the present invention can vary over a broad range. A total treatment regimen can comprise a plurality of individual treatments defined over a treatment period. The specific treatment regimen provided to a patient will be defined by a provider prior to and, in some respects, during a treatment that is underway. The time appropriate for a LLLT treatment regimen will be dependent, at least in part, on the type of wound or physiological malady being treated with LLLT. For example, post-surgical LLLT treatment to enhance wound healing in oral surgery will take about 6 days from surgical event to substantial healing. Recovery for knee replacement surgery may take up to about 90 days. Recovery from breast augmentation surgery may take up to about 50 days. In one aspect, the LLLT treatment of the present invention therefore incorporates selection and/or identification of a specific wound of physical malady in need of treatment. For example, knee replacement, hip replacement, oral surgery, breast surgery, abdominal surgery, facial surgery, vaginal surgery, nasal surgery, burns, cuts, or bruising (or any other applicable treatment types), can first be selected and/or identified as the applicable medical or cosmetic indication for which LLLT treatment is being prescribed. For chronic pain, treatment duration may be indefinite. Aesthetic/cosmetic treatment (e.g., vaginal rejuvenation, hair growth, anti-aging) can be as needed, or for as long as the patient and her provider deems appropriate.

Information can be collected and stored or transmitted of one or a plurality of dose applications, for example, each dose, a plurality of doses provided to a patient over a period such as daily, every other day, weekly, biweekly or monthly. The effectiveness of an applied treatment can be monitored and, if appropriate, be adjusted by changing the parameters of the patient's dosage. In this regard, the medical provider can observe the patient in person or through medical telemetry using an imaging device present at the patient's location, where the camera is in communication with the provider via the Internet for example. The provider can rate the patient's healing, pain rating, etc. after application of one or more LLLT treatments. Information associated with a change in wound rating or condition using the Bates-Jenson Wound Assessment Tool, for example, or wound assessment pain rating etc. can be monitored and plotted or otherwise correlated against the dosage to characterize the patient's response to LLLT over the course of a treatment regimen.

Wound rating or condition, and the progress (or lack thereof) in wound healing can be obtained via imaging. Review of those images can be by a medical technician or similar who is trained to grade or rate the healing level as shown in the images, or the technician can use a standardized image rating for grading. Alternatively, the wound condition and progress of healing can be graded or rated automatically using computer image analysis. Information about the wound healing obtained from images, can be included in patient medical records, as well as used for diagnosis by the medical provider. Still further, the wound healing information from images of the patient can also be used for management and modification of the LLLT dosage from a prior LLLT prescribed to the patient.

The provider can generate an initial LLLT treatment prescription including dosage to be applied to the patient using the inventive LLLT treatment devices. Instructions associated with such dosage is transmitted to or loaded on (such as via a computer, wirelessly or USB connection) into the PBM control module. The PBM control module can activate the treatment and other componentry to provide the LLLT treatment to the patient as defined by the treatment plan generated by the provider.

At some time after the treatment has been started, the provider can review information collected by the LLLT treatment device and transmitted to a control or operations center (such as on a remote device accessible by the provider). The provider can review such data to determine whether dosage modifications are indicated. The provider can also collect information about the progress of the treatment in person, where such in person observation can also be incorporated into data associated with the patient's LLLT treatment.

In this regard, prescription and/or dosage adjustments can be indicated in relation to one or more of the following for generation of initial LLLT treatment dosage, management thereof and possible modification during a patient treatment protocol: cause of a wound (e.g., surgical, cut/tear, burn etc.); size of incision or wound; wound type (e.g., laparoscopic vs. open surgeries or chronic), depth of affected areas and tissue type (e.g., organ, bone, muscle, skin), location on the body; other area on the body being treated associated with healing of wound (e.g., blood supply, lymph ducts, nerves, etc.); type of wound dressing used (if a garment delivery element is being used for LLLT); phase of healing; primary physiological indication of each phase of each phase (e.g., pain, swelling, bruising, contraction, infection, scarring etc.); the type of LLLT delivery element (e.g., type of light guide configuration, indication); size of LLLT delivery element; patient profile and characteristics (e.g., BMI, body part/cavity sizes, skin tone, skin texture, age etc.); patient compliance history (e.g., length of previously completed treatments, time of day for typical device use, patient input during treatment with VAS pain scale, GRC and other feedback mechanisms; biphasic dosage response of light therapy; sensor information (e.g., environmental conditions, incision condition and patient health and activity data acquired between start of LLLT treatment regimen and current observation).

When subsequent LLLT treatments are indicated for that patient, the collected data from a prior treatment protocol can be consulted to determine the dose that has historically resulted in effective healing, pain improvement etc. A new LLLT treatment dosage designed for the patient can then be generated and delivered to the patient during one or more subsequent treatments. The pertinent information about the new LLLT treatment dosage is also recorded, as well as any response thereto, and becomes historical data to be used in the calculation of future doses for that patient. Thus, the characterization of the patient's response to LLLT can be incorporated into further dosage determination for that patient or for a relevant patient population.

In some respects, the LLLT treatment device can incorporate preset operations/instructions within the firmware associated therewith, that is, the operations can be stored in the PBM control module, to allow the LLLT treatment information for a patient to be provided substantially without the need for external communications. Such self-sustained operation can be useful when the LLLT treatment device is operated in a location where wireless communications access is not available. The operations of the LLLT treatment device and related patient information when no wireless communication is available can be stored within the LLLT treatment device machine. Moreover, the LLLT treatment device can also suitably incorporate communication ports, for example USB ports, or the like to allow the device to use downloaded operational instructions, and to upload stored operational parameters.

In some respects, the PBM control module housing and/or the LLLT delivery element can provide information to the patient or provider, such as by a touchscreen. Alternatively, the PBM control module can be associated with a computerized program that is available in "app" form on a smartphone, tablet or the like. Such communication can be from the LLT device to the smartphone, tablet, etc. using Bluetooth® as discussed elsewhere herein. The LLT device can be connected to a remote smartphone, tablet, etc. device, such as that of a medical provider who is monitoring a course of LLLT treatment for a patient via the cloud, as would be recognized.

The patient and medical provider can be provided with a user interface to facilitate operation of the PBM control module from a remote device or server. The respective user interfaces for the patient and the medical provider may differ due to the need for a different level of information for each of them. In this regard, the patient may be provided with minimal information, such as duration of a dose of LLLT treatment, how many doses will occur that day, how much more time for treatment etc. The provider user interface can include additional information that can facilitate the provider's continued treatment of the patient.

Notably, such remote monitoring of patient information, can further improve the efficacy of treatment. For example, the patient user interface can be configured to push questions to the patient during the treatment period. If the patient responds that they are in more or less pain than expected, the medical provider can use such information to further design dosage regimes for that patient, as well as for other patients in need of treatment. The patient can also be provided an opportunity to review the calculated dosage before it is administered. Thus, administration of LLLT to the patient may be feedback controlled, and tailored to the patient's particular physiology and real-time condition. In this regard, the data stored in or uploaded from the PBM control module, the inventive LLLT treatment devices and associated methods of the present invention provide the additional benefit of enhancing the body of provider knowledge regarding the appropriate dosing regimens and efficacy of LLLT treatments that have heretofore not been attainable.

As noted previously, at the end of a treatment period, the components of the PBM control module can be deactivated to substantially prevent reuse of the device without the definition of an appropriate dosage for a patient. As such, the PBM control modules of the present invention can be made operable only during the course of a defined patient treatment period. The device can be activated, for example, but generation of a code from the device for input into an app or online, whereby instructions can be sent to the device with appropriate activation instructions. The patient LLLT treatment can be provided as described elsewhere herein.

During a defined treatment, the provider can monitor, manage, and, if appropriate, modify the dosage of a patient's LLLT treatment via such a remote device. The provider can also use messaging (e.g., text or email) or telephone capability to communicate with the patient during treatment. The provider can review the wound being treated in real time using video capabilities and imaging.

Any communication between the provider and the patient will suitably comply with necessary rules and regulations relating to medical record confidentiality and security. In this regard, any patient medical information will be securely stored, for example, in the in the cloud. As would be recognized, cloud computing has emerged as one optimization of traditional data processing methodologies. A computing cloud is defined as a set of resources (e.g., processing, storage, or other resources) available through a network that can serve at least some traditional datacenter functions for an enterprise. A computing cloud often involves a layer of abstraction such that the applications and users of the computing cloud may not know the specific hardware that the applications are running on, where the hardware is located, and so forth. This allows the computing cloud operator some additional freedom in terms of implementing resources into and out of service, maintenance, and so on. Computing clouds may include public computing clouds, such as Microsoft® Azure, Amazon® Web Services, and others, as well as private computing clouds.

It should be noted that in some of the Figures accompanying this application, single light beams are shown for simplicity. However, the beams will be understood to comprise a range of angles associated with light emanating from the light source, light guide and/or the tissues being treated with LLLT to provide therapeutic effects to a patient in need of treatment. Thus, light emanating from the light guide(s), traveling through the interior of the devices, exiting the devices for treatment of tissues, and, if present, emanating from tissues for capture by sensors should be understood to comprise scattered, diffuse, or direct light from light sources that will result in treatment of a range of tissue areas, as opposed being a single beam applied to a single tissue area as might be inferred from the accompanying drawings.

Referring to FIG. 1, patient 100 in need of LLLT treatment can be associated with a PBM control module 105, where such control module is in operational engagement with remote device or server 110. Such operational engagement can be via Wifi, Bluetooth, RFID etc. or can be by periodic wired engagement with a device (e.g., computer, tablet, etc.) [not shown] via USB etc. in a local network or through an intranet or the internet though wired or wireless communications networks existing today or that may be developed in the future. PBM control module 105 is in operational engagement with at least one light source 115, communications module 120, battery 125, microcontroller 130, and optional sensor(s) 135 module. Controller 130 generally incorporates at least a microprocessor 140 and memory 145. When in operational engagement with at least one optical waveguide [not shown]—referred to herein as a "light guide" or "light guide arrangement" herein—and at least one LLLT delivery element [not shown], a wearable LLLT device [not shown] can be provided in a number of configurations, as discussed hereinafter. Patient 100 can also be engaged with one or more patient monitoring device(s) 150, such as devices capable of obtaining and transmitting information relevant to user input, surveys, treatment adherence questions, medical condition, treatment compliance, physical activity, emotional state, food intake or the like. Such monitoring device(s) 150 are meant to comprise an expansive definition of devices that exist today or that can be devised in the future, but for illustration, can include a sensor cluster embedded in the treatment device or light guide, or a separate a mobile device configured with user input and tracking functionality (e.g., smartphone), fitness tracker (e.g., Fitbit®), wireless vital sign tracker (e.g., blood pressure monitor, heart rate monitor, glucose monitor) etc. Monitoring device(s) 150 can be continuously or periodically in communication with remote device or server 110 and/or with PBM control module 105. Medical and or other relevant information from data from patient 100 can be transmitted to 110 from PBM control module 105 directly, from monitoring device(s) 150 directly, or PBM control module 105 and monitoring device(s) 150 can transmit data to and from each other, and, from time to time, pertinent data can be transmitted to remote device or server 110. Collected patient 100 data can be stored on PBM control module 105 via memory 145, and/or on any memory capability present on monitoring device(s) 150, for transmission to remote device or server 110 or a local device [not shown], as appropriate.

Figure 2:
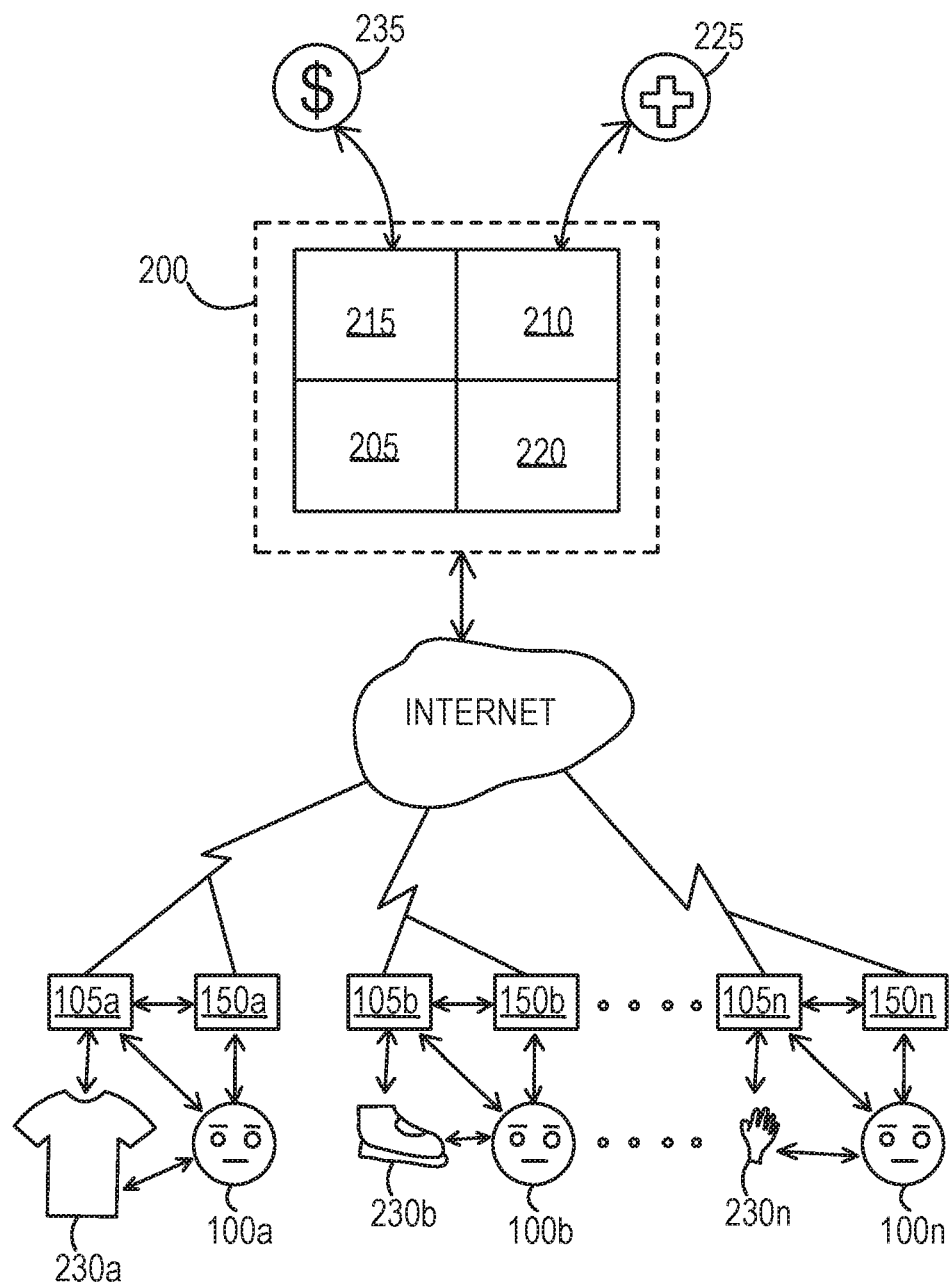
FIG. 2 illustrates a further implementation of the present invention whereby LLLT treatment is delivered and managed in a plurality of patients.

FIG. 2 illustrates functional elements of a LLLT telemedicine platform 200, engaged over the Internet or wide area network with a plurality of PBM control modules 105a, 105b . . . 105n associated with a plurality of patients 100a, 100b . . . 100n, who can each, independently, be associated with monitoring devices 150a, 150b . . . 150n. Platform 200 comprises a number of interconnected modules, such as a dosage information module 205, dosage provision module 220, payer module 215, and healthcare provider module 210, all of which can comprise machine learning-related instructions related to LLLT treatment delivery to patient 100a etc. Platform 200 may be on a computer cloud, shown as "Internet," or an operational or functional component of a device (e.g., computer, tablet, smart phone) [not shown] the various aspects of FIG. 2. Dosage information module 205 can further be in communication with payer module 215, via remote device or server 110 [not shown] for example, which can be associated with an insurance company computer system or database 235 or the like, but such payer module 215 need be utilized only when third party payer is required for a prescribing and provision a LLLT treatment. Dosage provision module 220, in communication with dosage information module 205, is configurable to provide instructions for the operation of one or a plurality of PBM control modules 105a etc. before, during or after when patients 100a etc. are being treated with a LLLT device 230a etc. Dosage provision module 220 and dosage delivery information module 205 comprises a significant aspect of artificial intelligence enabled LLLT treatment development and machine learning algorithms and associated knowledge basess to deliver highly effective personalized dosage for each of patients 100a etc. being treated with LLLT. LLLT treatment dosage can be defined and delivered to PBM control module 105a etc. via instructions or the like generated by dosage provision module 220 that where such instructions can include information associated with, among other things, information about one or more patients 100a etc., including parameters associated with their medical condition, physical condition, age, weight, ethnicity, skin color, physical activity level, preexisting condition, etc. Such patient information can be generated by a medical provider or other professional 225 via healthcare provider module 210, and/or delivered from patient 100a etc. via direct user input and/or from patient, caregiver, etc, or collection and transmission of patient 100a etc. data collected from monitoring device(s) 150a etc.

Figure 3:
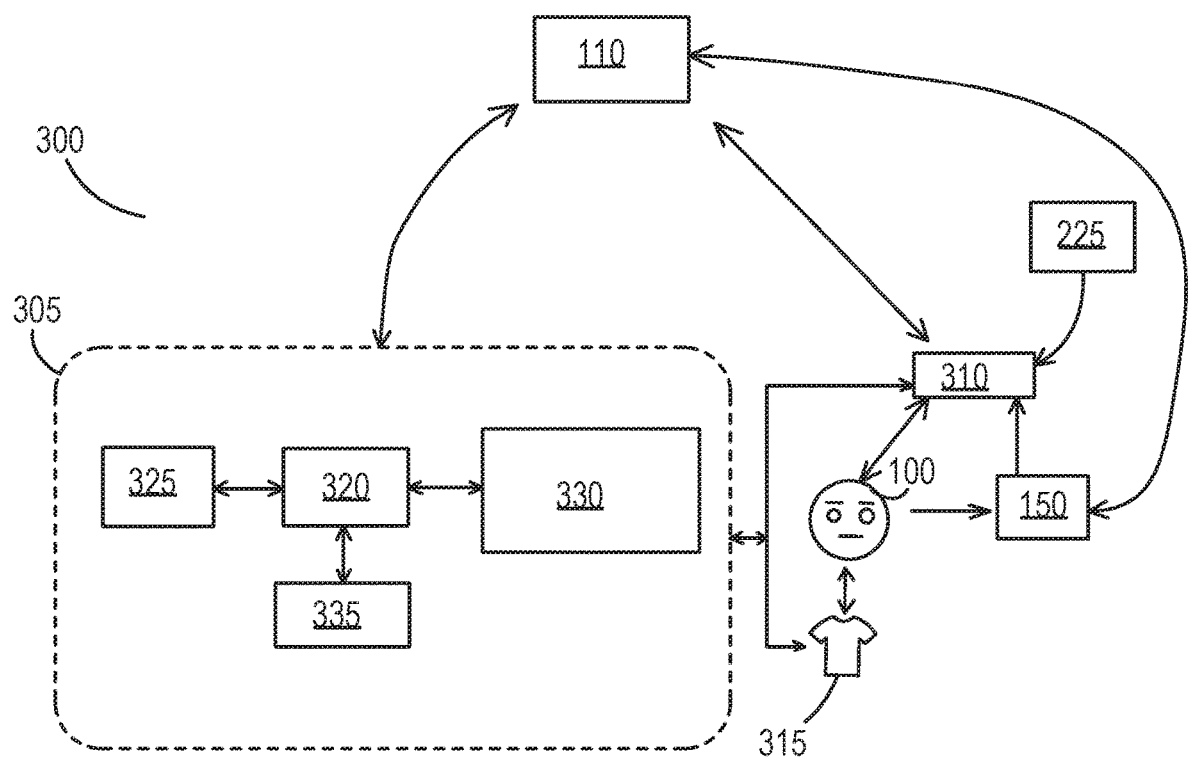
FIG. 3 illustrates a further implementation of functional elements of a methodology of the present invention whereby LLLT treatment is delivered to a patient.

FIG. 3 illustrates an exemplary personalized clinical LLLT treatment delivery implementation of the present invention comprising a plurality of clinical function elements 305 in LLLT clinical delivery framework 300, some of which can be optional. Data can be input from 310, which can be one or more device(s) configured to obtain information relevant to the treatment of patient 100. Such information can be generated from provider 225 input, or from patient 100 input, and/or data generated from monitoring device(s) 150. LLLT treatment device 315 includes PBM control module [not shown], and at least one light guide or light guide arrangement [not shown] and at least one LLLT delivery element [not shown] in operational engagement therewith. LLLT treatment device 315 can be operationally engaged with the plurality of clinical functions 305 that can comprise one or more of LLLT treatment program module 320, LLLT dosage meter 325, patient data sensor module 330, and LLLT patient treatment data collection module 335. LLLT treatment program 320 can incorporate a defined amount of LLLT treatment deliverable to patient 100 as prescribed by provider 225, for example. Such treatment program module 320 can include dosage instructions suitable to generate LLLT treatment to wearable LLLT device 315 placed on patient 100, where such dosage provides instructions relevant to, for example, duration for each total LLLT treatment regimen, number of individual LLLT treatments in each total treatment regimen, duration of each treatment in each treatment regimen, time between LLLT treatments in each treatment in a total treatment regimen, wavelength(s) of light provided in each treatment in a total treatment regimen, etc. In some aspects, provider 225 selects a LLLT treatment regimen for patient 100 from available patient information, and such treatment is deliverable from a skin-touchable or wearable LLLT treatment device 315 when such device 315 is placed on patient 100 in the form of a garment or an infrared blanket.

Figure 4:
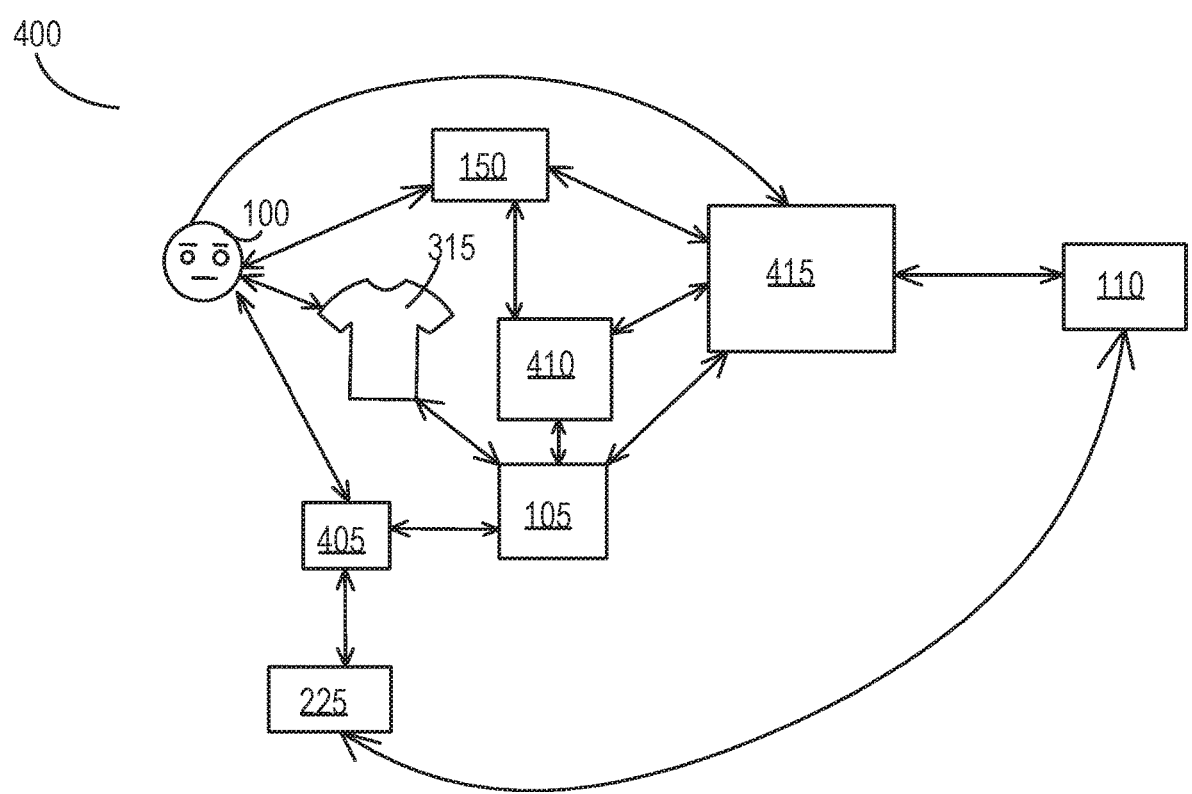
FIG. 4 illustrates a further implementation of functional elements of a methodology of the present invention whereby LLLT treatment is delivered to a patient.

FIG. 4 illustrates a dosage operational framework 400 for an implementation of the present invention. In a first aspect, PBM control module 105 can be in a LLLT dosage delivery mode, where dosage delivery instructions 405 can comprise a LLLT dosage prescription for patient 100 as defined by a provider 225 at the start of a treatment regimen. LLLT treatment dosage instructions 405 provided to PBM control module 105 can, from time to time, be modified/updated by provider 225 from reviewing or processing of ongoing treatment information 410. Such ongoing treatment information can comprise operational information 415 generated from one or more of sensor data, patient compliance data, images, patient activity level, patient weight, provider generated information relevant to the patient or treatment, or the like, where such information is derived from one or more of patient(s) 100, PBM control module 105, remote device or server 110, monitoring device(s) 150, provider 225, skin-touchable or wearable LLLT device 315. As to the latter, wearable device 315 can be configured with sensors [not shown] to monitor patient 100 for compliance, for example, where such sensor information can be incorporated in operational information 415, such as by communication of wearable device 315 with one or more other components present in operational framework 400. Such ongoing LLLT treatment information can also be derived from patient 100 input, such as how she is feeling, for example on a recognized pain scale, emotional state etc.

Figure 5:
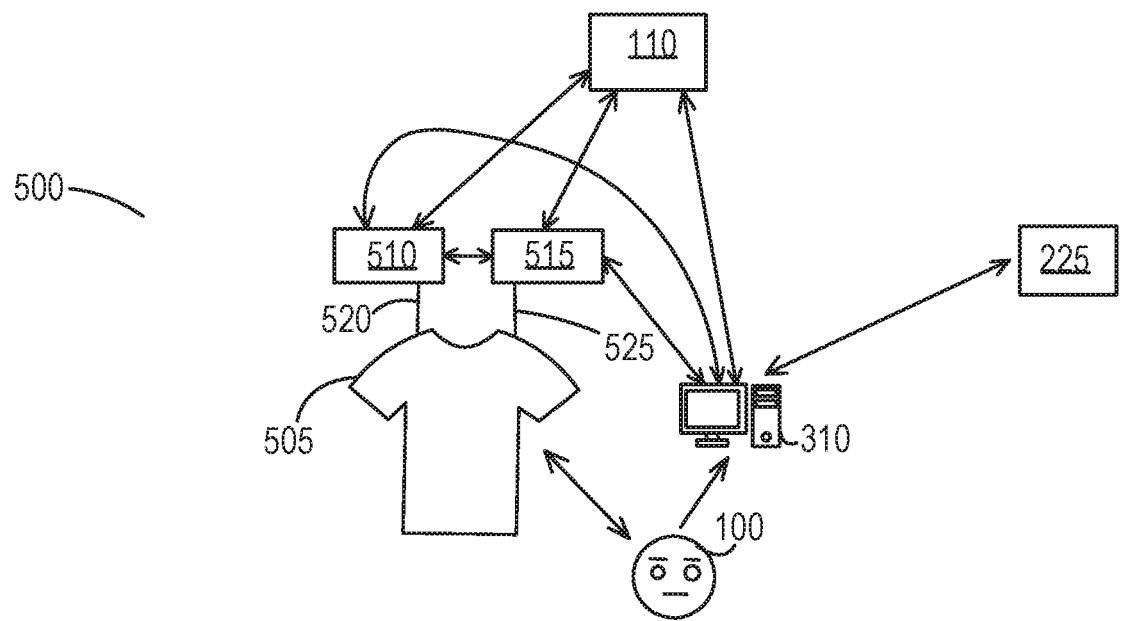
FIG. 5 illustrates functionality of an implementation wherein two control modules are utilized to deliver LLLT to a patient.

FIG. 5 provides a further implementation 500 of the present invention. Wearable LLLT device 505, here illustrated as a shirt garment but that can comprise any suitable format (e.g., shirt, pants, brace, sock, bandage, insert, or a combination thereof), can comprise more than one PBM control module, here shown as 510 and 515. PBMs 510 and 515 are each, independently, shown as in operational control with light guide arrangements 520 and 525, respectively. Each of or both of PBM control modules 510 and 515 can each, independently, be configured with more than one light guide arrangement, where such more than one light guide arrangement can be in operational and optical engagement with at least one light source [not shown] that is configured in each of 510 and 515. Either or both of PBM control modules 510 and 515 can each, independently or in communication with each other be configured with more than light source [not shown], a configuration that can be desirable when more than one light guide arrangement [not shown] is used, and multiple wavelengths of light are provided for treatment of patient 100. As discussed previously, dosage instructions can be generated by provider 225, and/or patient 100 by way of device(s) 310 that can be configured to communicate directly with PBM control modules 510 and 515 and/or by way of remote device or server 110, for example. While PBM control modules 510 and 515 are shown in a position away from wearable LLLT device 505, as would be recognized, in significant implementations, 510 and 515 can be permanently integrated into or otherwise associated (such as by mounting or other securable connection) with wearable LLLT device 505 such that light guides 510 and 515 are arranged so that treatment of the area(s) [not shown] on patient 100 in need of treatment can be affected.

Figure 6:
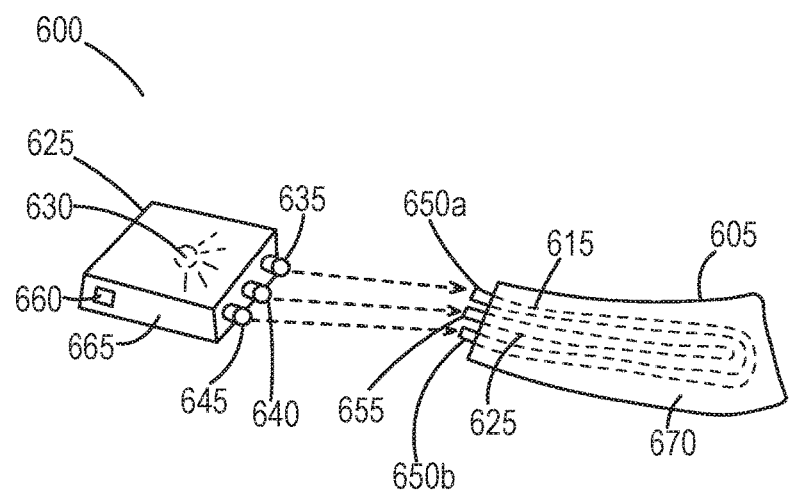
FIG. 6 illustrates a wearable LLLT treatment device in the form of a bandage or garment.

In FIG. 6, wearable LLLT device 600 is shown. LLLT delivery element 605 comprises, for example, a garment or bandage configuration having patient facing side 610 wherein LLLT light guides 615 and 620 are shown arranged proximally to patient facing side 610 [not shown] so as to allow LLLT treatment delivered from 615 and 620 to reach a patient [not shown] in use. PBM control module 625 comprises, among other things, at least one light source 630. In this implementation, three light guide engagement ports 635, 640, and 645 are present in PBM control module 625. Engagement port 635 is engageably attachable to light guide 615 at first end 650*a* and engagement port 645 is engageably attachable to light guide 615 at second end 650*b*. Engagement port 640 is engageably attachable to light guide 620 at first end 655. To better ensure that loss does not occur at the light guide connection points, optical couplers [not shown] can be used, for example, as discussed elsewhere herein. PBM control module 625 is shown here with a single light source 630 to provide light to and through the various light guides 615 and 620, however, more than one light source, each capable of delivering different wavelengths, can be used, where such one or more light sources are configurable to allow transmission of a therapeutic amount of LLLT to a patient in need of treatment. Power switch 660 is shown on housing 665, however, other forms of power activation, such as remote activation, can be used. LLLT treatment delivery element 605 can incorporate fasteners etc. [not shown] on outer surface 670 opposite to patient facing side 610 [not shown] for retaining device 600 in a relatively fixed position on a patient's body.

Figure 7:
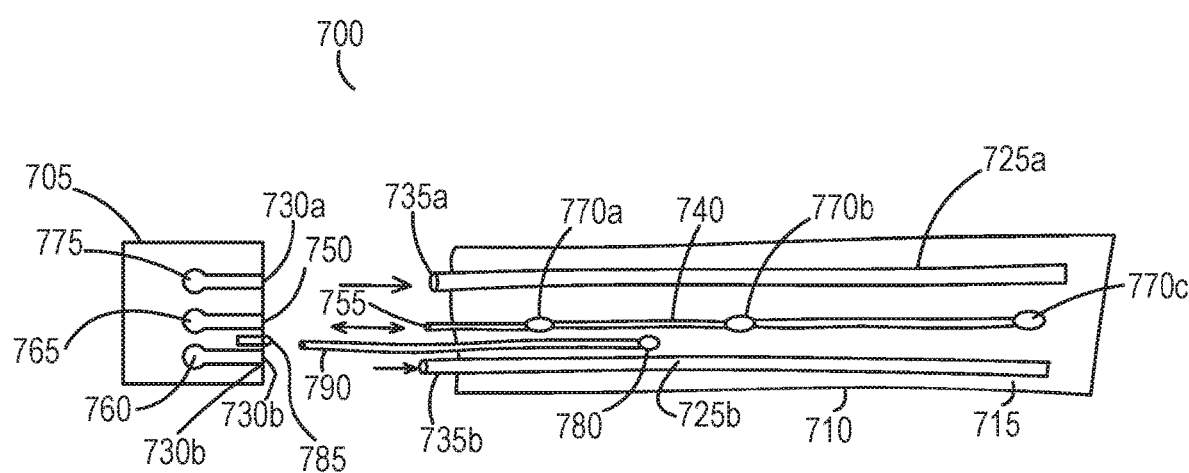
FIG. 7 illustrates a further wearable LLLT treatment device in the form of a bandage or garment.

FIG. 7 illustrates a further implementation of the present invention. Wearable or skin-touchable LLLT device 700 comprises PBM control module 705 removably or permanently engageable with LLLT delivery element 710 in the form of a garment, blanket, or bandage. Such engagement can be removable or substantially permanent, with the former allowing PBM control module 705 to be switched out for use with alternate LLLT treatment protocols, for servicing, or the like. LLLT delivery element 710 comprises patient facing side 715 and outer side 720 [not shown]. Patient facing side 715 incorporates light guide 725*a* and light guide 725*b*, where 725*a* and 725*b* are operationally and optically engagable with light guide engagement ports 730*a* and 730*b* at ends 735*a* and 735*b*, and light guide 740 is operationally and optically engageable with light guide engagement port 750 at end 755. Such operational and optical engagement can be via optical connectors [not shown]. Light sources 760 and 775 are configurable to emit light in the red, infrared, green or amber wavelengths so as to deliver light in such wavelengths to light guide 725*a* and 725*b*, respectively, at patient facing side 715. Light source 765 is configurable to emit light in the green or amber wavelengths for certain treatments or in the UVC or blue wavelengths from light guide 740 so as to help prevent or treat infection during the healing of a wound. LLLT delivery can be localized from light guide 740 at patient facing side 715 at a plurality of light delivery nodes 770*a*, 770*b*, and 770*c*, which can be generated by cladding with opaque coating at least part of an interior or exterior surface of light guide 740 except for such locations where light delivery is desired. Such coating, which can be via a reflective or mirrored coating applied to light guide 740, can be configurable to prevent substantially light from exiting except at specific locations on a light guide. In further implementations, red light or other wavelengths can be localized. Side emitted fiber optics can suitably be used for such localized LLLT delivery.

In a further implementation, sensor cluster 780 can comprise one or more of a skin conductivity sensor, a temperature sensor, an oxygen saturation sensor, or a photo sensor. When in operational engagement with light guide 790, sensor cluster 780 allows collection of skin conductivity, temperature, oxygen saturation, or light reflection or emission from the patient's wound and, when in operational engagement, can transmit such patient emitted light to sensor 785, which can be any and all aforementioned sensor data to optimize the operation of PBM control module 705 for LLLT treatment application.

In a further implementation, light source 775 can be configured to deliver light at a different wavelength from that delivered by 760. For example, a wavelength of 970 nm for treating deeper tissue can be delivered by 760 to the wound of a patient, alternating or simultaneously delivered, with a wavelength of 650 nm for treating tissue closer to a patient's skin surface [not shown]. The LLLT dosage amount delivered can be the same or different from each of the light sources 760 and 775.

Figure 8A:
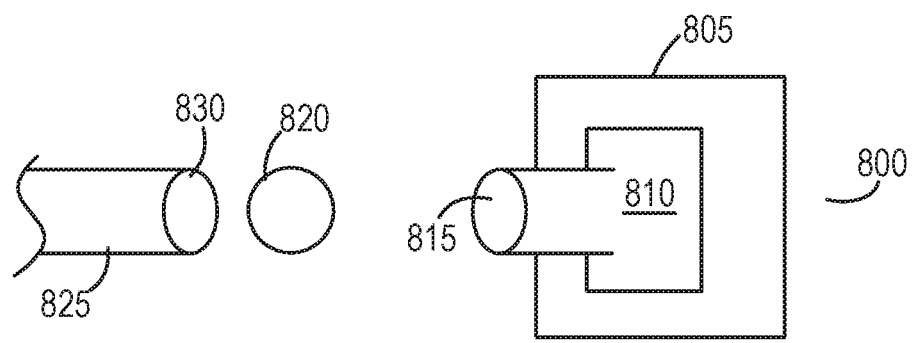
FIGS. 8A-8B illustrate one form of light guide engagement.
Figure 8B:
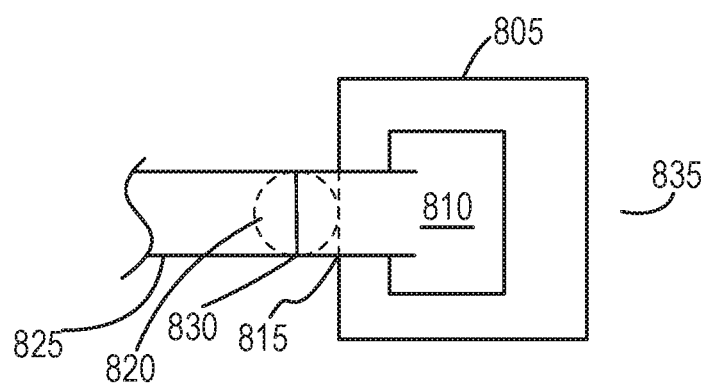

FIGS. 8*a* and 8*b* illustrate an exemplary low loss optical connector configuration suitable for use in the present invention. As shown in unengaged configuration 800, PBM control module 805 is configured with light source 810, wherein 810 is operationally and optically engaged with engagement port 815. Low loss optical connector 820 is sized to be engageable with engagement port 815 and light guide 825 at terminal end 830. When in engaged junction 835, low loss optical coupler 820 operates to connect engagement port 815 to light guide 825 at connection point 830 with substantially low level of air gap and resulting in reduced loss to about 3 dB loss of light energy from light source 810 into 825.

Figure 9A:
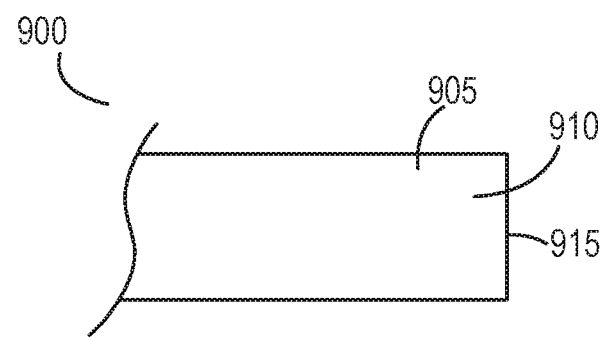
FIGS. 9A-9B illustrate a light guide end configuration.

FIG. 9*a* illustrates an exemplary partial view of a light guide configuration suitable for use in the present invention. In FIG. 9*a*, light guide 900 has outer surface 905 and interior surface 910. Light guide 900 has terminal end 915 where light would not travel farther when provided by a light source [not shown] is operationally and optically engaged with light guide 900.

Figure 9B:
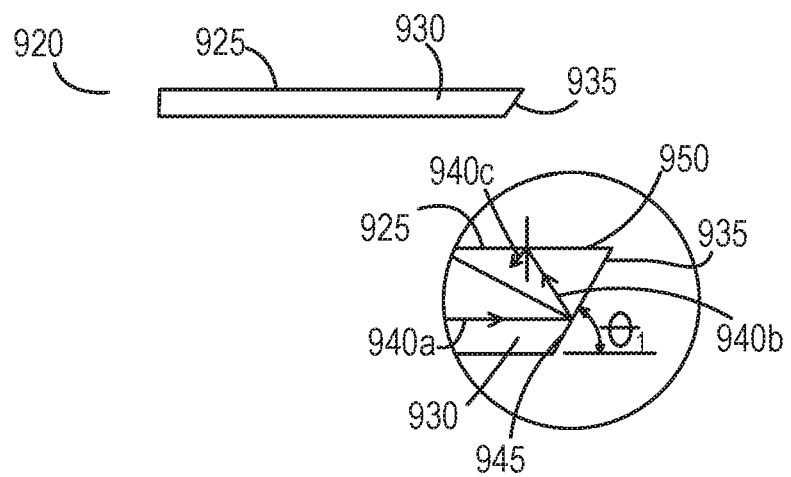

FIG. 9b illustrates a further partial view of a light guide configuration suitable for use in the present invention. Light guide 920 has outer surface 925 and interior surface 930. Terminal end 935 comprises exterior angle $\ominus_1$, which is less than 90 degrees. When light beam 940a is generated from a light source [not shown], 940a will be reflected/deflected off interior end surface 945 as 940b, which will then be reflected/deflected off of interior surface 950 as 940c. As would be recognized by this illustration, the angular configuration of terminal end 935 can enhance light energy distribution from light guide 920 when incorporated into a LLLT delivery element [not shown]. The interior surface 945 of terminal end 935 can be treated with a reflective material to enhance this behavior.

The LLLT treatment devices of the present invention can be utilized in LLLT delivery elements that are configurable to provide LLLT treatment as well as, in some implementations support, to enhance healing and reduce pain. For example, such LLLT treatment devices can be useful in to treat one or more of a patient's knee, ankle, hip, back, wrist, elbow etc., and suitably configured delivery elements are associable with light guides and PBM control modules. A notable feature of each of the implementations of the present invention is that there is substantially no electrical energy proximal to the site of the patient injury or area undergoing treatment. In this regard, power, and associated electrical connections and componentry, can centralized and located in the PBM control module. Still further, the PBM control module(s) can be removably engageable with the delivery element, such as being securably mountable on or proximal to the delivery element. PBM control modules can be permanently engaged with a LLLT delivery element, also.

Figure 10A:
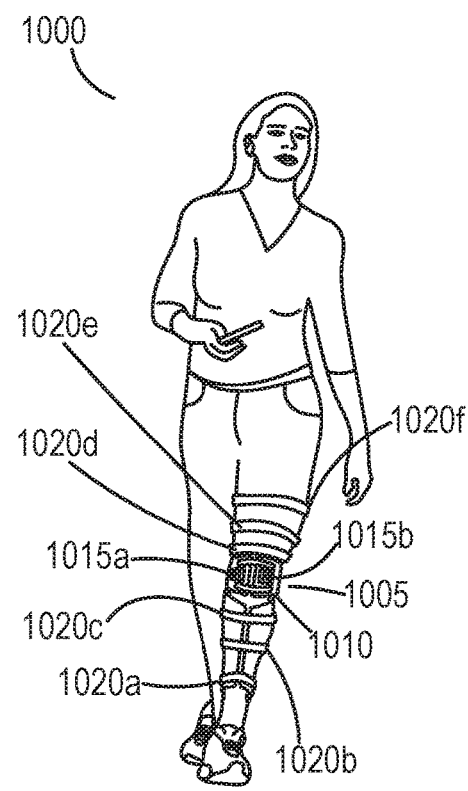
FIGS. 10A-10C illustrate a LLLT device for treatment of a leg or knee area.

FIG. 10a illustrates a LLLT device configured to treat a patient at or around the area of the knee, for example, in post-operative care after a total knee arthroplasty (TKA), as discussed previously. In this regard, patient 1000 is shown wearing LLLT knee device 1005 on her leg 1010. Device 1005 is shown with 2 PBM control modules 1015a and 1015b that are in operational engagement to provide LLLT treatment to patient 1000, but one or two or more PBM control modules can be used, as appropriate for a treatment protocol. Device 1005 is removably securable to leg 1010 by fasteners 1020a, 1020b, 1020c, 1020d, 1020e, and 1020f which can be Velcro® type fasteners, straps, clips, etc. More or fewer fasteners can be used.

Figure 10B:
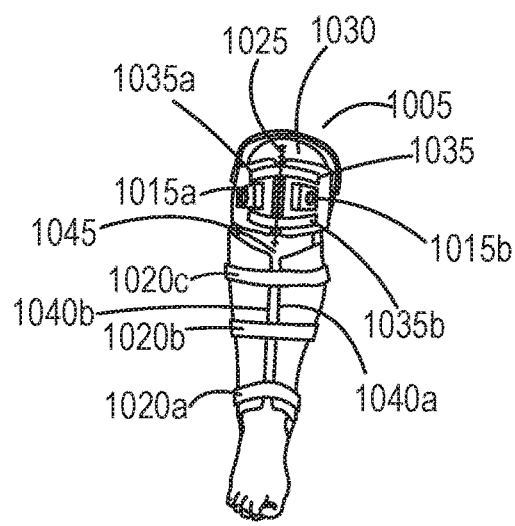

FIG. 10b illustrates device 1005 from the knee area of leg 1010 and below. Knee incision 1025 is shown below device 1005. While knee incision 1025 is visible in FIG. 10b, as would be recognized, typically such an incision could be covered with an absorbent bandage [not shown], as long as such bandage allowed delivery of LLLT treatment to knee incision 1025 as needed. Knee support area 1030 is can also be configured to cover knee incision 1025 during healing. An absorbent bandage or other suitable material can be placed below knee support area 1030, as long as the material [not shown] will allow LLLT treatment to suitably reach knee incision 1025. Knee area support 1030 is securable in use by fasteners 1035a and 1035b, which can be Velcro® type fasteners, straps, clips, etc. Device sides 1040a and 1040b are secured to lower leg 1045 by fasteners 1020a, 1020b and 1020c. More or fewer fasteners and different fastener types can be used as long as such arrangement allows device 1005 to remain secured on lower leg 1045 during treatment.

Figure 10C:
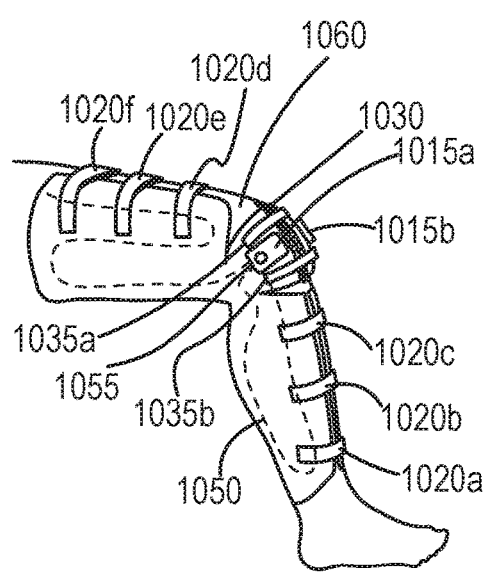

FIG. 10c illustrates another view of device 1005 on leg 1010 wherein light guide arrangement 1050 is shown in operational and optical engagement with PBM control module 1015a at engagement port 1055. Note that light guide arrangement 1050 is configured to dispense light from a patient facing side [not shown] of device 1005 not just in the area proximal to knee incision 1025, but also along a substantial portion of leg 1010 at lower leg 1045 and thigh area 1060 so as to allow LLLT treatment to be delivered to areas of leg 1010 known to be associated with enhancing healing, such as the lymph areas [not shown] below the knee area and blood vessels [not shown] above, behind, and below the knee area, which are associated "healing vital areas." As discussed further herein, such "healing vital areas" can be treated with different light wavelengths than that used to treat the area proximal to knee incision 1025. In this regard, it can be helpful to use at least two PBM control modules as illustrated here with 1015a and 1015b, however, a single PBM control module capable of dispensing LLLT in suitable wavelengths to treat knee incision 1025 as well as such "healing vital areas" [not shown] can also be used when suitably configured with appropriate configuration of light guide arrangement 1050 to deliver LLLT to areas proximal to those needing treatment in patient 1000.

Figure 11A:
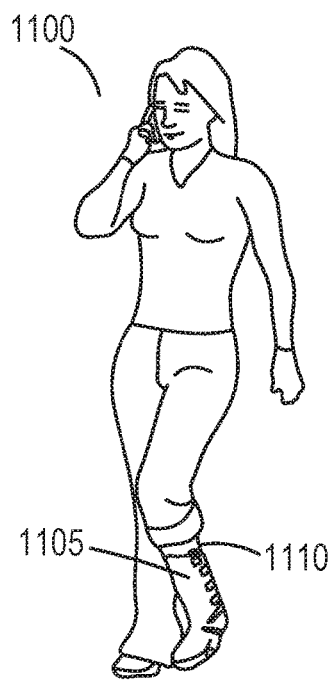
FIGS. 11A-11C illustrate a LLLT device for treatment of an ankle or foot area.

FIG. 11 illustrates a LLLT device configured to treat a patient at or around the area of the ankle or foot, for example, in post-operative care after ankle or foot surgery. In this regard, in FIG. 11a patient 1100 is shown wearing LLLT lower extremity device 1105 on her lower leg 1110. Lower extremity device 1105 can be configured as a soft garment, sock, a shoe, or a brace of hard material with load supporting features.

Figure 11B:
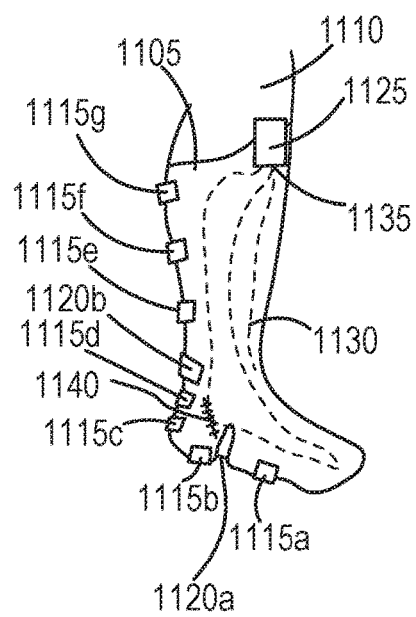

FIG. 11b illustrates lower extremity device 1105 in closeup whereby device 1105 is secured to lower leg 1110 by fasteners 1115a, 1115b, 1115c, 1115d, 1115e, 1115f and 1115g, which can be Velcro® type fasteners, clips, straps, etc. More or fewer fasteners and different fastener types can be used as long as such arrangement allows device 1105 to remain secured on lower leg 1110 during treatment. Areas 1120a and 1120b are open can, in some aspects, improve the ability of patient 1100 to walk while wearing device 1105 by enhancing lower limb flexibility during wearing of device 1105. PBM control module 1125 is shown in engagement with light guide arrangement 1130 at engagement port area 1135, where 1130 is configured to deliver LLLT treatment to ankle area incision 1140 from patient facing side [not shown] of device 1105. More than one PBM control module 1125 can be used in device 1105 as appropriate for a treatment, especially when "healing vital areas" may be relevant as discussed previously.

Figure 11C:
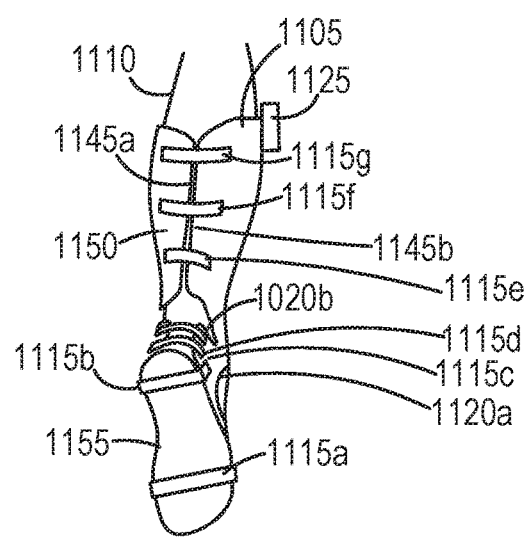

FIG. 11c illustrates a rear view of lower extremity LLLT device 1105. Device sides 1145a and 1145b are securable with fasteners 1115e, 1115f and 1115g on device outer surface 1150. Lower extremity LLLT device 1105 can have bottom portion 1155 for treatment to the sole of the foot with, for example, with plantar fasciitis or heal spur surgeries, to further enhance the ability of patient 1000 to walk while wearing device 1105.

Figure 12A:
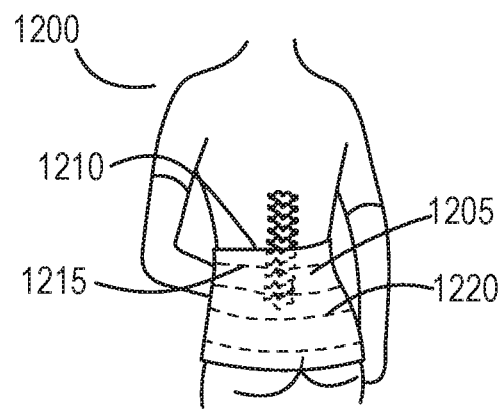
FIGS. 12A-12C illustrate a LLLT device for treatment of a hip and lower back area.
Figure 12B:
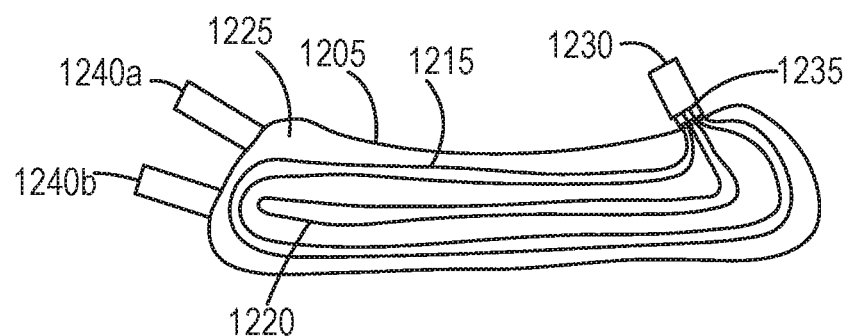
Figure 12C:
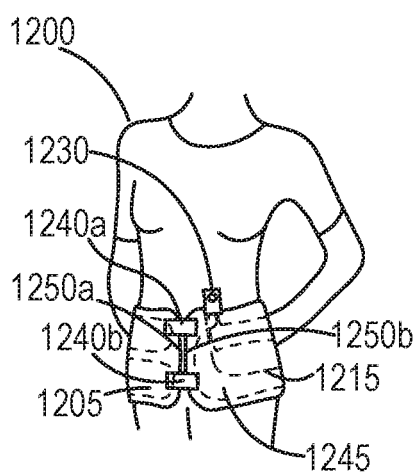

FIG. 12 illustrates a LLLT device configured to treat a patient at or around the area of the hip joint and lower back, for example, in post-operative care after hip replacement or lower lumbar surgery. In this regard, in FIG. 12a patient 1200 is shown wearing LLLT hip and lower back device 1205 on an area proximal to an incision [not shown] around the hip [not shown] or lower back 1210. Light guides 1215 and 1220 are shown whereby LLLT treatment can be delivered, as further shown in FIGS. 12b and 12c, from patient facing side 1225 proximal to hip [not shown] and lower back 1210 when device 1205 is worn by patient 1200. PBM control module 1230 is engageable with light guides 1215 and 1220 at engagement port area 1235. Fasteners 1240*a* and 1240*b* can be Velcro® type fasteners, straps, clips, etc. configured on outer surface 1245, for example.

FIG. 12*c* illustrates device 1205 from front of patient 1200 whereby hip and lower back device 1205 is secured by fasteners 1240*a* and 1240*b* to bring device ends 1250*a* and 1250*b* together for wearing. More or fewer fasteners and different fastener types can be used as long as such configuration allows hip and lower back device 1205 to remain secured on patient 1200 during a LLLT treatment. PBM control module 1230 is shown configured to dispense LLLT to light guides 1215 and 1220 patient facing side 1225 of device 1205. While only one PBM control module 1230 is shown in FIG. 12*c*, more than one PBM control module can be used as appropriate for a treatment, especially when "healing vital areas" may be relevant as discussed previously. An absorbent bandage or other suitable material [not shown] can be placed proximal between patient facing side 1225 and the area of hip [not shown] or lower back 1210 that may have an incision [not shown], as long as at least some of the bandage material will allow LLLT to suitably reach thereto for treatment.

Hip and lower back device 1205 can also be useful to treat hip arthritis and lower back pain. In this regard, LLLT suitable to treat such indications can be generated from PBM 1230 to be delivered from patient facing side 1225 using light guides 1215 and 1220 configured to dispense LLLT treatment in one or more areas proximal to hip [not shown] and lower back 1210.

Figure 13:
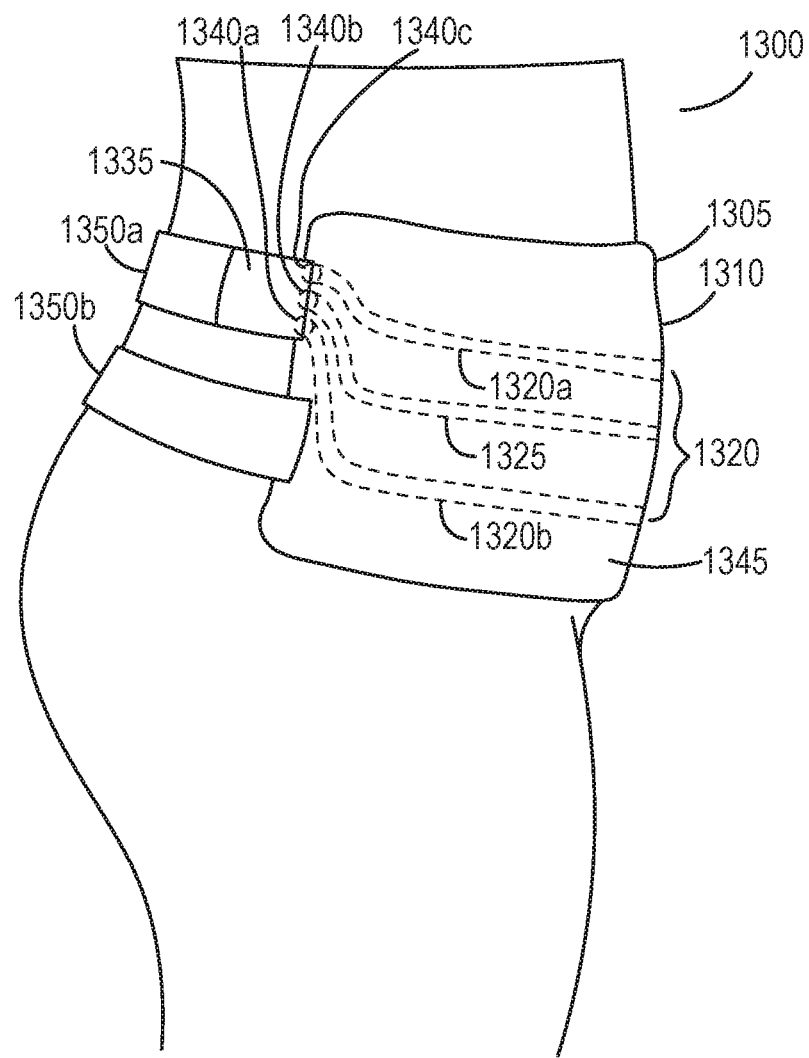
FIG. 13 illustrates a LLLT device for treatment of an abdominal area.

The inventions of the present invention can also be used to treat the pelvic and lower abdominal regions of a patient in need of treatment thereof. In this regard, FIG. 13 illustrates patient 1300 having abdominal LLLT device 1305 proximal to abdominal region 1310. Light guide arrangement 1320 is configured to deliver LLLT treatment as portions 1320*a* and 1320*b* and second light guide 1325, along with 1325, is configured to deliver a therapeutic amount of LLLT from patient facing side 1330 [not shown]. PBM control module 1335 is in operational and optical engagement with light guide arrangements 1320 and 1325 at light guide engagement ports 1340*a*, 1340*b*, 1340*c*. Outer device surface 1345 comprises fasteners 1350*a* and 1350*b*, which can be Velcro® type fasteners, straps, etc. Device 1305 can be used to, for example, treat incisions proximal to the abdominal/pelvic region, or can be used to treat pain or other conditions proximal thereto that can be benefited from LLLT treatment provided at one or more wavelengths.

Figure 14:
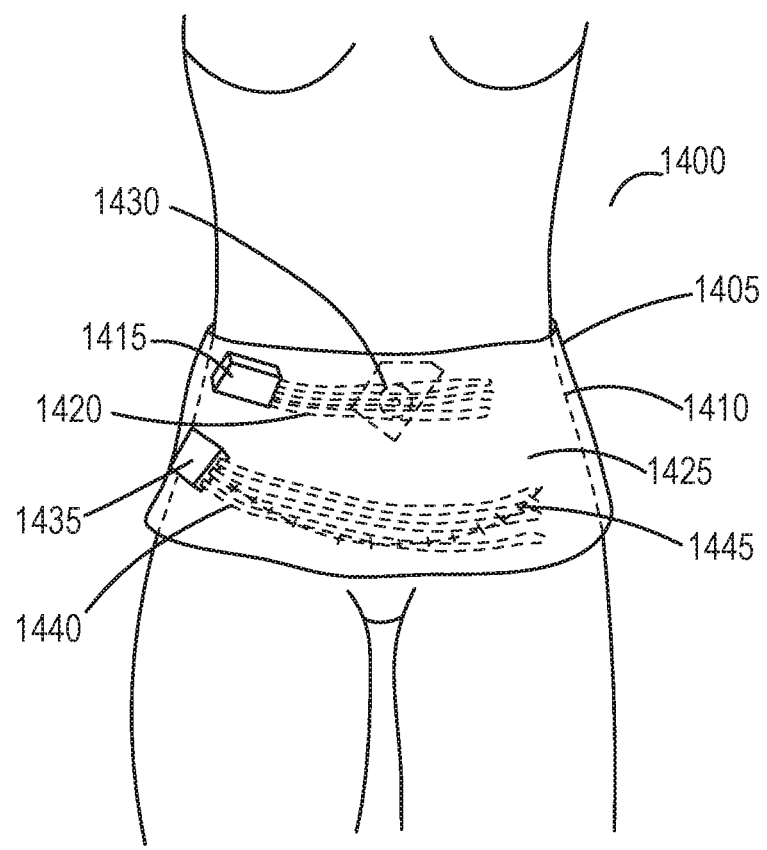
FIG. 14 illustrates a LLLT device for treatment of abdominal and pelvic areas.

FIG. 14 illustrates a further implementation of a compression binder for an abdominal/pelvic area LLLT treatment device, such as would be useful for cosmetic surgery, such as to enhance healing rate and to reduce pain for abdominal area liposuction and or "tummy tucks." Patient 1400 is shown with device 1405 worn proximal to abdominal/pelvic area 1410. First PBM control module 1415 is shown in operational and optical engagement with light guide arrangement 1420 on outer surface 1425, which is configured to deliver LLLT treatment proximal to abdominal incision 1430. PBM control module 1415 can be removably or permanently mountable on outer surface 1425. Second PBM control module 1435 is shown in operational and optical engagement with light guide arrangement 1440 to provide a therapeutic amount of LLLT treatment to areas proximal to pelvic incision 1445. While FIG. 14 is shown with two PBM control modules 1415 and 1435, suitable arrangements using one or three or more PBM control modules are also contemplated. Also, one or more light guide arrangements [not shown] can be configured to deliver a therapeutic amount of LLLT treatment to one or more additional areas covered by device 1405, where such LLLT treatment can comprise the same or different light wavelengths than the LLLT treatment delivered to areas proximal to incisions 1430 and 1445.

Figure 15B:
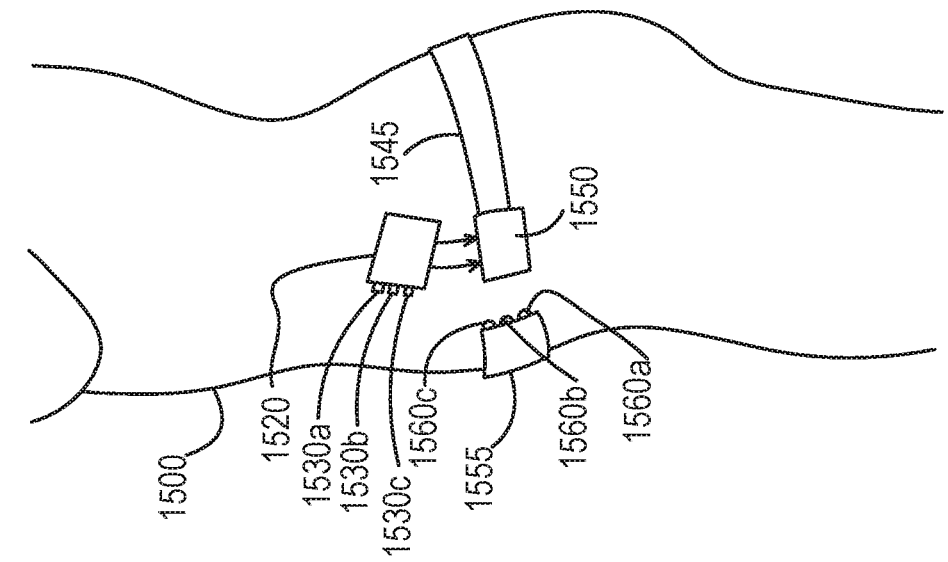
FIGS. 15A-15B illustrate a LLLT device for treatment of a pelvic area.
Figure 15A:
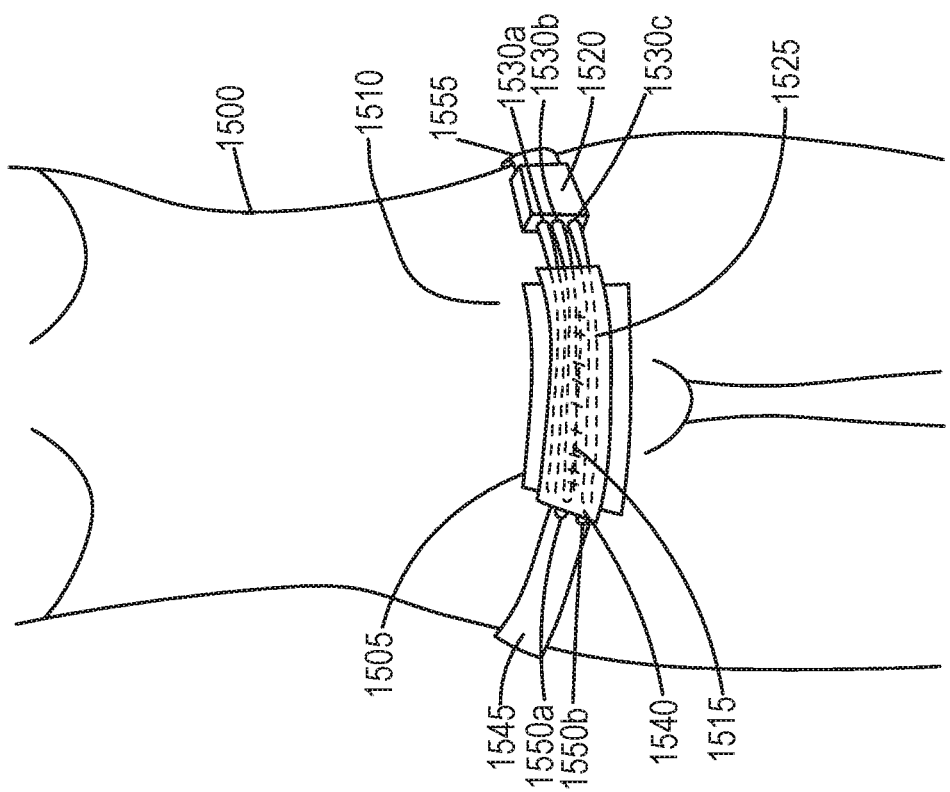

FIGS. 15*a* and 5*b* illustrate an implementation of a pelvic area LLLT treatment that can, for example, have utility for post-operative care after a C-section or other pelvic area surgery. In this regard, FIG. 15*a* shows patient 1500 wearing pelvic LLLT device 1505 proximal to pelvic area 1510 so as to deliver a therapeutic amount of LLLT treatment to pelvic incision 1515. PBM control module 1520 is in operational and optical engagement with light guide arrangement 1525, whereby light guide arrangement 1525 is engaged with PBM control module 1520 at light guide engagement ports 1530*a*, 1530*b*, and 1530*c* (shown in extended length to enhance visibility) to deliver LLLT treatment from patient facing side 1535 [not shown], thereby providing a therapeutic amount of LLLT treatment to one or more areas proximal to incision 1515. Device outer surface 1540 is engagable with belt outer side 1545 via fasteners 1550*a* and 1550*b*, which can be Velcro®, straps, clips, snaps etc. More or fewer fasteners can be used. For illustration, device 1505 is shown without a holder in FIG. 15*a*, but a holder can be useful to secure PBM control module 1520, especially when 1520 is configured to be removable from device 1505, as discussed in relation to 15*b*.

FIG. 15*b* illustrates a side view of pelvic LLLT device 1505 on patient 1500. PBM control module 1520 is shown as removably insertable into PBM control module holder 1550. PBM control module holder 1550 is shown in a holster format, but other formats can also be suitable to allow PBM 1520 to be removed for servicing or for use in other LLLT devices. Device belt second end 1555 is shown with engageable light guide connectors 1560*a*, 1560*b*, and 1560*c* that are engageable with engagement ports 1530*a*, 1530*b*, and 1530*c*. Other suitable device belt 1545 configurations are also contemplated.

Figure 16:
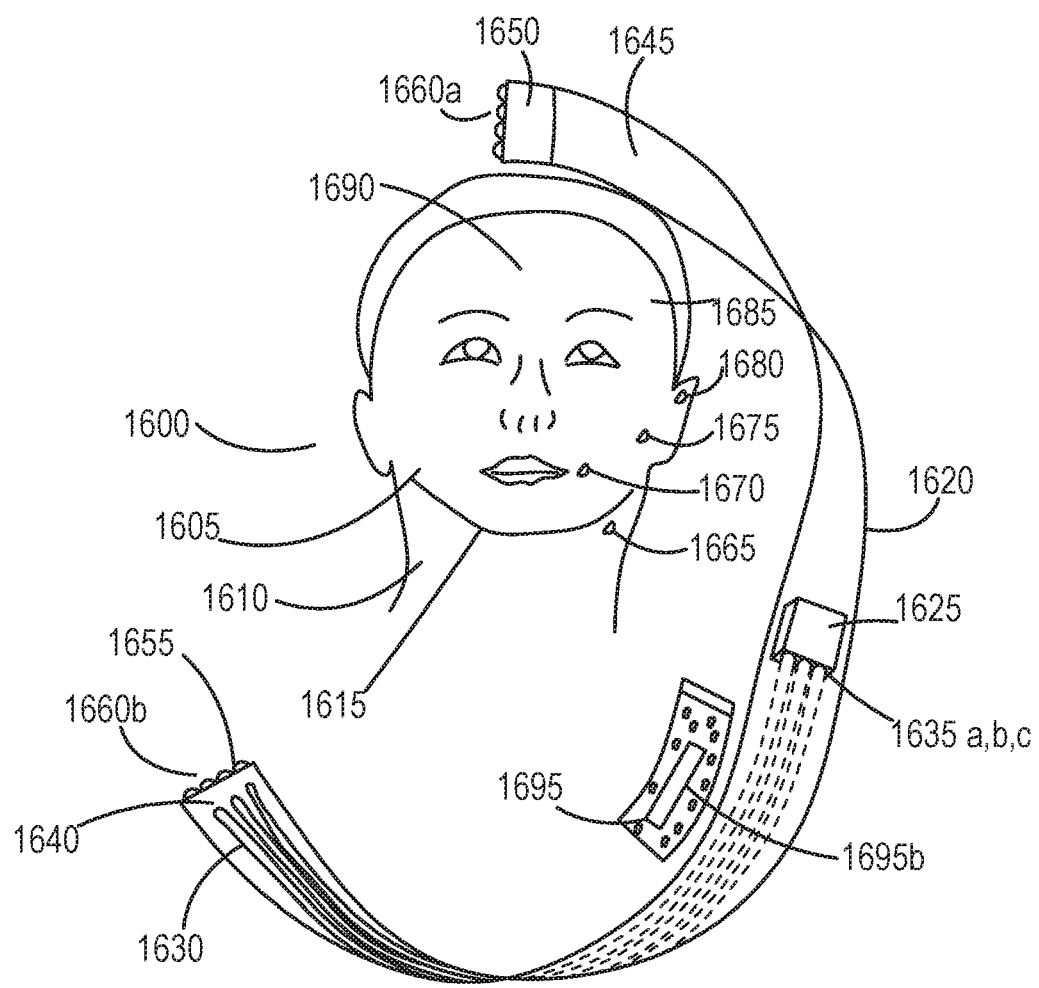
FIG. 16 illustrates a LLLT device for treatment of a facial area.

FIG. 16 illustrates a further implementation of the LLLT treatment devices of the present invention whereby post-surgical indications associated with the facial and neck regions can be therapeutically treated. In this regard, patient 1600 having facial region 1605, neck region 1610, and chin region 1615 can be treated with LLLT head and neck device 1620 in conjunction with a rhytidectomy, otherwise known as a "facelift." PBM control module 1625 is in operational and optical engagement with light guide arrangement 1630 by removable engagement with engagement ports 1635*a*, 1635*b* and 1635*c*, whereby light guide arrangement 1630 is configurable to provide a therapeutic amount of LLLT to patient 1600 from patient facing side 1640 to treat at least patient regions 1605, 1610, and 1615. Outer device surface 1645 comprises first and second ends 1650 and 1655, each comprising fastener pairs 1660*a* and 1660*b* that can comprise Velcro®, straps, buttons, clips, snaps, etc.

Device 1620 is shown with functionality to provide LLLT treatment to at least some of the patient areas typically associated with a facelift, for example, exemplary neck area incision 1665, mouth area incision 1670, cheek area incision 1675 and ear area incision 1680, however, the various aspects of device 1620 can be configured to treat more or fewer areas, on one or both sides of the facial, chin and neck regions 1605, 1610, and 1615 of patient 1600. For example, an additional PBM control module [not shown] can be configured to apply a therapeutic amount of LLLT to the temple 1685 and/or forehead 1690 regions as indicated, and the size and shape of device 1605 can be adjusted or extended to provide appropriate coverage of the areas in need of LLLT treatment. One or more ice packs 1695 having suitable light transmissive region 1695b can be incorporated to cover one or more of patient 1600 incisions 1665, 1670, 1675, 1680 etc. as needed.

FIG. 17 illustrates a use of a neck and face area LLLT treatment device, in the form of a compression garment, or used without compression, worn by patient 1700. Device 1705 is positioned on patient 1700 so that light guide arrangement 1710 can deliver LLLT as indicated, for example areas proximal to chin area 1715 and ear area 1720. Light guide arrangement 1725 is suitably configured, for example, to treat areas proximal to neck area 1730. PBM control module 1735 is operationally and optically engaged to light guide arrangement 1710, for example, with multiple hardness areas, using the highly flexible light guide design disclosed herein, at engagement ports 1740a, 1740b, and 1740c. PBM control module 1745 [not shown] can be suitably configured to deliver LLLT to light guide arrangement 1725, or PBM control module 1735 can be suitably configured to deliver LLLT to both light guide arrangements 1710 and 1725.

FIG. 18 illustrates a further implementation of a LLLT treatment device of the present invention, whereby a therapeutic amount of LLLT can be applied to the breast and proximal regions of a patient in need of treatment thereof, such as in a mastectomy, breast augmentation, or breast reduction procedure. In this regard, patient 1800 is shown with chest area LLLT device 1805 configured to fit proximal to at least one breast 1810a and, optionally, a second breast 1810b. PBM control module 1815 is in operational and optical engagement with light guide arrangement 1820 via engagement port 1825. Light guide arrangement 1820 is configurable to deliver a therapeutic amount of LLLT treatment on a patient facing side [not shown] to areas proximal to at least breast 1810a, including lymph node area 1830 proximal to underarm area 1835, which comprises a "healing vital area," as discussed elsewhere herein. Referring to FIGS. 18b and 18c, which illustrate side and back views, respectively, chest area LLLT device 1805 can be secured with chest strap 1840, for example, which can also incorporate one or more optional additional securing straps, such as shoulder straps 1845a and 1845b. Chest area LLLT treatment device 1805 can suitably incorporate back closure pairs 1850 and 1855 (e.g., fasteners such as Velcro®, straps, clips, hooks etc.), however, closure pairs can also be incorporated in a front portion 1860. FIG. 18 illustrates chest area device 1805 as having LLLT treatment provided only to one breast 1810a, however, it would be recognized that device 1805 can suitably be configured to provide LLLT treatment to breast 1810b, also.

Figure 19:
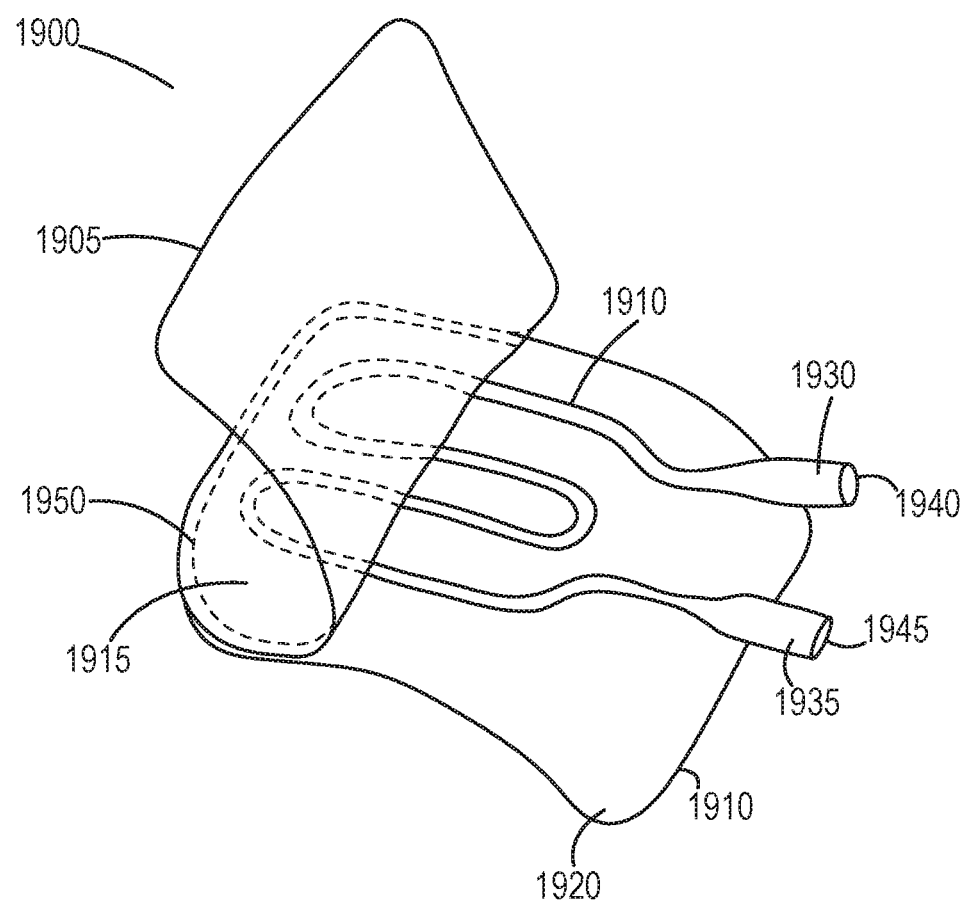
FIG. 19 illustrates a LLLT device in the form of a bandage.

FIG. 19 illustrates a further implementation of a LLLT device herein in the form of a bandage or blanket or garment that can be placed proximal to an area on a patient in need of LLLT treatment. Device 1900 comprises first covering 1905 comprising a translucent or transparent material suitable for delivery of LLLT from light guide arrangement 1910 at patient facing side 1915. A close proximity or contact of first covering 1905 with light guide arrangement 1910 is implemented, for example, with a sprayed adhesive or pressure from tension within the material for covering 1905 so that frustrated total internal reflection or light transmission is achieved for at least some—for example, a percentage—of the surface of light guide arrangement 1910 in the desired are for treating the patient. Depending on the length of the light guide, about 5 to about 90% of a given are for light scattering through frustrated total internal reflection or transmission may be desirable.

Second covering 1920 comprises a material that is substantially opaque to light being delivered from light guide arrangement 1910 so that light is delivered substantially only in the direction of patient facing side 1915. Second covering 1920 can comprise a thick material, such as fabric and/or cushioned material (e.g., foam) to enhance patient comfort in use on an outer side 1925 [not shown]. Light guide terminal ends 1930 and 1935 are operationally and optically engageable with a PBM control module [not shown] via light guide engagement ports [not shown] connectable with optical connectors [not shown] in light guide ends 1940 and 1945. First covering 1905 and second covering 1920 are connectably attached via seal 1950 to enclose substantially all of light guide arrangement 1910 therein. Seal 1950, which will be around substantially all of an exterior of device 1900 for use, can be sewn, glued, ultrasonically welded etc.

Figure 20:
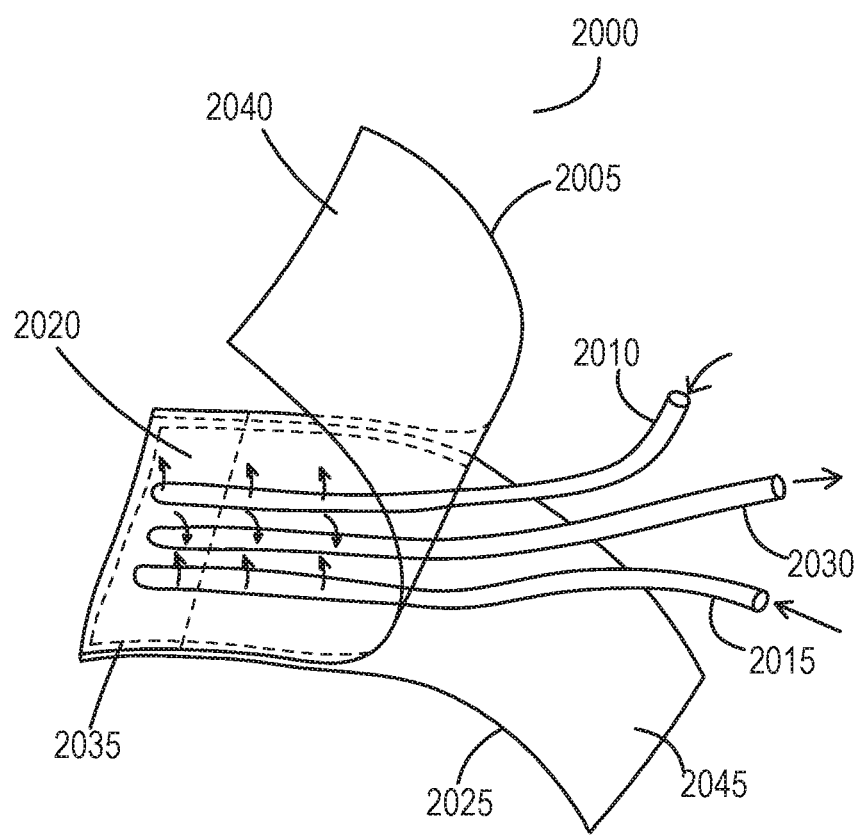
FIG. 20 illustrates a LLLT device in the form of a bandage configurable to detect light emitted from a patient wound area.

FIG. 20 shows another implementation of a bandage or blanket or garment LLLT treatment device of the present invention. Device 2000 has first covering 2005 that is translucent or transparent to allow substantially all light delivered by light guides 2010 and 2015 (shown by directional arrows out of light guides 2010 and 2015) to be delivered from patient facing side 2020 when device 2000 is suitably configured for use. Second covering 2025 can comprise a thick material, such as fabric and/or cushioned material (e.g., foam) to enhance patient comfort in use. Light guides 2010 and 2015 are operationally and optically engageable with a PBM control module [not shown] at engagement ports [not shown]. Light guide 2030 is configurable to transmit light generated from a patient wound [not shown] to a sensor [not shown] associated with the PBM control module [not shown] to collect light reflected or generated from a patient's wound (shown by directional arrows into light guide 2030) when device 2000 is in use. As discussed elsewhere herein, such light generated from patient wounds can be helpful in assessing the effectiveness and stage of healing, such as by providing information about infections, etc. When configured for use, seal 2035 securely attaches first covering interior side 2040 to second covering interior side 2045. Seal 2035 and proximal arrangement of light guides 2010, 2015, and 2030 with first cover 2005 can be by sewing, gluing, ultrasonic welding, etc.

Figure 21:
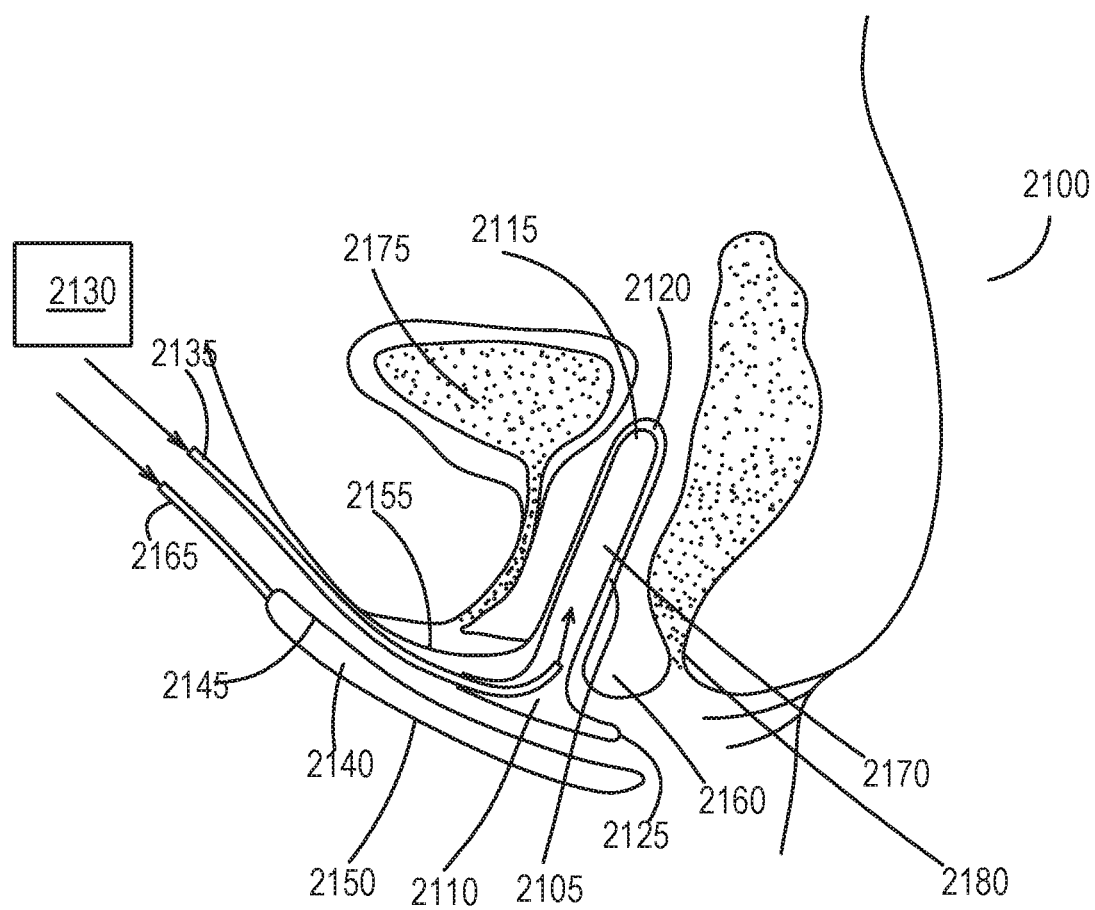
FIG. 21 illustrates a LLLT device for treatment in the form of an insertable vaginal light therapy device used with a light therapy delivery liner.

Referring to FIG. 21, female body 2100, in the case of an illustrated male-to-female sex reassignment surgical patient, will normally require regular dilation to prevent collapse of the newly constructed vaginal cavity 2105, among other medical requirements. In this regard, the inventive vaginal light therapy insert 2110 can provide enhanced post-surgical healing. The present invention includes a vaginal light therapy insert 2110, which can be fabricated of medical grade, optically transmitting clear material such as acrylic, polycarbonate, or silicone.

Vaginal light therapy insert 2110 has interior end 2115 that is configured to reach proximally to interior end 2120 of vaginal cavity 2105. Vaginal light therapy insert 2110 has anterior end 2125 that is configured to facilitate removal of vaginal light therapy insert 2110 from vaginal cavity 2105, as necessary.

Vaginal light therapy insert 2110 is operationally and optically engaged with PBM control module 2130 via at least one light guide 2135 for transferring LLLT into vaginal light therapy insert 2110 for subsequent transmission to vaginal cavity 2105 etc. PBM control module 2130 can include at least one light source [not shown] that emits light in the blue, green, red to near-infrared wavelengths for various stages and indications during an overall treatment protocol. PBM control module 2130 is operationally engaged with at least one light source [not shown] that, as discussed elsewhere herein, is regulated as to power level, wavelength, duty cycle, pulsing frequencies to deliver desired dosages in a dosage period and in an overall treatment protocol.

For example, light at about 650 nm to about 700 nm for red and about 830 nm to about 980 nm in the infrared range can be introduced to the vaginal cavity 2105 from vaginal light therapy insert 2110 at a dosage of from about 0.5 to about 21 Joule/cm$^2$/day immediately post-surgery to promote healing during the early stages of recovery and to reduce pain and swelling in a male to female sex reassignment patient. The wavelengths associated with green, from about 5210 nm to about 530 nm, can be administered at from about 0.5 to about 2.5 Joule/cm$^2$/day intermittently or simultaneously with other wavelengths, or can be used for treatment of vaginal or vulva rejuvenation, overactive bladder (OAB) syndrome, vaginal dilation, vaginismus or vulvodynia, conditions that can be associated with patients other than sex reassignment patients needing post-surgical healing assistance. The wavelengths associated with blue, from about 410 nm to about 495 nm, can be used at about 210 to about 900 mW/cm$^2$ to an actually or potentially infected area during wound healing.

Vaginal light therapy insert 2110 can be incorporated in vaginal cavity 2105 for extended periods to enhance healing thereof and to reduce the possibility that vaginal cavity 2105 will collapse, such as is an adverse post-surgical complication in male to female sex reassignment, for example. Operationally, when vaginal light therapy insert 2110 is inserted into vaginal cavity 2105 during dilation—that is, post-operatively—the dimensions of vaginal light therapy insert 2110 are configured to provide the effect of dilation. For vaginal rejuvenation, vaginal light therapy insert is also appropriately sized for therapeutic effectiveness and patient comfort.

Vaginal light therapy insert 2110 can also be used in conjunction with vulvar area light therapy delivery liner 2140 having first and second sides 2145 and 2150, respectively. First side 2145 is configured to, for example, to deliver light to vulvar regions 2155 and 2160 of patient 2100. Light therapy delivery liner 2140 can be removed as needed for patient 2100 to urinate etc.

Light therapy delivery liner 2140 is operationally and optically engaged with PBM control module 2130 via at least one light guide 2165. The light source(s) [not shown] that are each, independently, engaged with vaginal light therapy insert 2110 and light therapy delivery liner 2140 from within PBM control module 2130 can be the same or different. Light therapy delivery liner 2140 can also be used alone as indicated by a medical provider in some cases, such as with perineum tears that can occur in vaginal births.

When PBM control module 2130 is activated, LLLT is delivered through at least one light guide 2135 to interior device portion 2170 and/or through first side 2145 so to allow light energy reach vaginal cavity 2105 and vulvar regions 2155 and 2160.

Light therapy delivery liner 2140 is optimally sized to maintain the comfort and privacy of patient 2100 during healing. Wearability of light therapy delivery liner 2140, as well as vaginal light therapy insert 2110, can be enhanced by patient's 2100 wearing of undergarments [not shown] that can keep light therapy delivery liner 2140 in place which, in turn, can further secure light therapy delivery liner 2140 in vaginal cavity 2105.

LLLT treatment dosages can be applied to either or both vaginal cavity 2105 and vulvar regions 2155 and 2160 as prescribed by a medical provider. In this regard, and as non-limiting examples thereof, for sex reassignment surgery, the LLLT dose provided to a patient in need of treatment can have a duty cycle that is provided to from about 8 minutes on and about 30 minutes off for about three cycles per treatment on day 21, day 2 and day 3 postoperative, then drop to 2 cycles per treatment on about day 4 to about 8 post-op, thereafter one cycle per treatment until about day 24 for a sex-reassignment patient, for example. Moreover, the light source(s) [not shown] can provide light to either or both of vaginal cavity 2105 or vulvar regions 2155 and 2160 at substantially the same times and wavelengths, or light LLLT treatment wavelengths or dosages can vary.

For vaginal rejuvenation, overactive bladder conditions, hemorrhoids or the like shorter periods of use, such as once or twice a day to achieve a dosage of from about 0.3 to about 3.5 Joule/cm$^2$/day inside the vagina to provide therapeutic benefits to a bladder 2175 or hemorrhoids proximal to the anal area 2180 for a defined period, such as about 30 minutes, about 60 minutes or about 2120 minutes per day may be indicated by the medical provider depending on the individual patient, however, variation of treatment times will not modify the inventive effects of the invention.

FIGS. 22a, 22b, 22c illustrate first, second, and third views of vaginal light therapy insert 2200, wherein Vaginal light therapy insert 2200 is rotated 90 degrees between 22a and 22b, and 22c is a bottom view thereof. Vaginal light therapy insert 2200 is capable of both dilation and light energy delivery as shown. Light guide 2205 is optically engaged with vaginal light therapy insert 2200 by incorporation of light guide end 2210 into interior 2215 of vaginal light therapy insert 2200 proximal to vaginal light therapy insert anterior end 2220 at vaginal light therapy insert engagement port 2225. FIG. 22b omits light guide 2205 to better illustrate engagement port 2225.

According to one aspect of the present invention, vaginal light therapy insert 2200 can be configured having a rim 2230, here shown, as one example, in the approximate shape of water drop, whereby rim 2230 will substantially prevent the totality of vaginal light therapy insert 2200 from wholly entering vaginal cavity 2105 when inserted therein, while also making vaginal light therapy insert 2200 easier to handle and extract. Vaginal light therapy insert 2200 can be configured as an elongated portion 2235 with outer surface 2240 that together substantially conform to a diameter of a patient's vaginal cavity 2105 with a small amount of taper from anterior end 2220 to interior end 2245. Various lengths and diameters of vaginal light therapy insert 2200 can be configured as needed for each patient, as discussed in more detail herein.

In one aspect of the present invention, vaginal light therapy insert 2200 can be fabricated from optically clear, medical grade polymers. To selectively allow a therapeutic dosage of LLLT to be emitted from vaginal light therapy insert 2200, interior region 2215 of vaginal light therapy insert 2200 that is proximal to outer surface 2240 (where the outer surface 2240 is that aspect of vaginal light therapy insert 2200 that comes into contact with the outer portion of patient vaginal cavity 2105) can incorporate particles or added imperfections to generate discontinuity areas in one or more locations in vaginal light therapy insert 2200. Such discontinuity areas, here shown as 2250 and 2255 have been found, in some aspects, to enhance light scattering light from interior 2215 so as to improve the distribution of light to patient tissues [not shown] in use.

For example, surface discontinuity can be in the form of 2255, which is configured to enhance light delivery at the entrance of vaginal opening area [not shown]. Clinically, with a sex reassignment surgery that incorporates a penile flap to provide a portion of a vulvar region in a patient, discontinuity area 2255 has been found to facilitate the light concentrated radiation at the end of the vaginal opening area to reduce the occurrence of a post-surgical complication called "contracture." Moreover, when a patient's colon flap is used in a male to female sex reassignment, discontinuity area 2255 can also increase the light intensity at the area of opening of a patient's vagina, reducing the complication called "ring scar contraction" around the vaginal opening area. Incorporated air bubbles or particles inside vaginal light therapy insert 2200 can also be used to create discontinuity area 2250 while surface imperfections can be used to create discontinuity area 2255, and vice versa.

Figure 23:
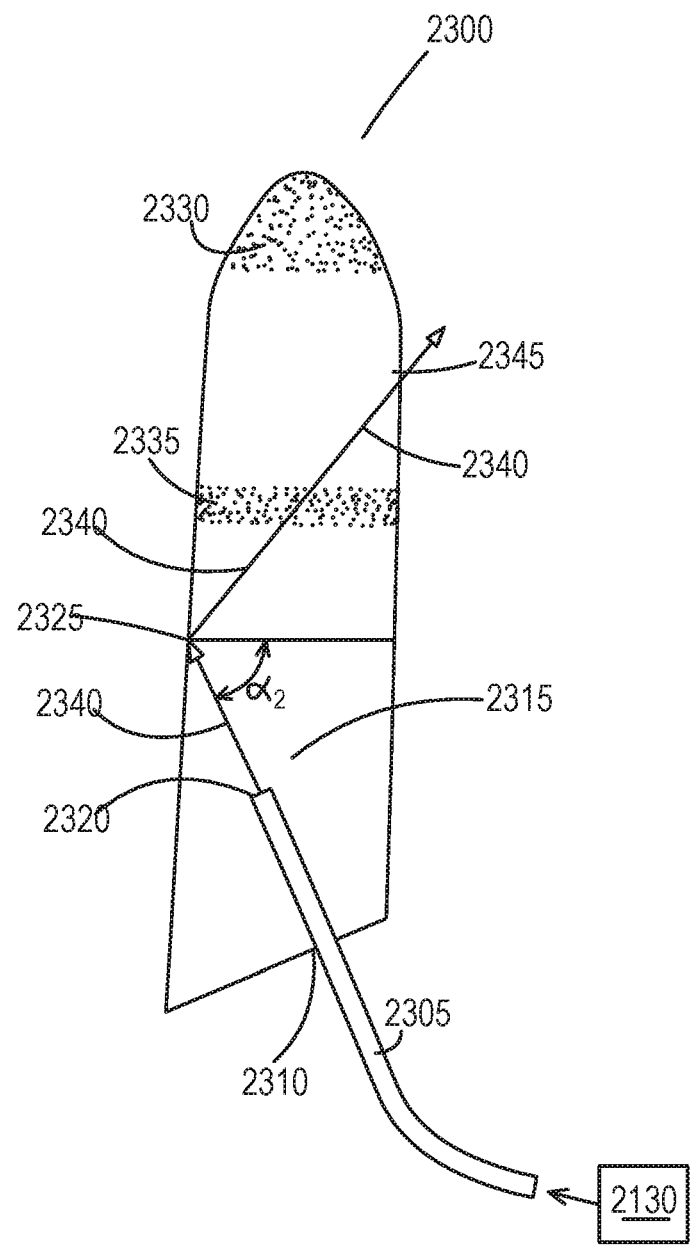
FIG. 23 illustrates an implementation of light delivery in and through an implementation of an insertable vaginal light delivery device.

FIG. 23 illustrates vaginal light therapy insert 2300 configured to minimize light loss so as to maximize light energy delivery to patient tissue needing treatment thereof when vaginal light therapy insert 2300 is inserted in a vaginal cavity 2105. Light guide 2305 is incorporated within and is operationally and optically engaged with vaginal light therapy insert 2300 through anterior end 2310. Light guide 2305 terminates at interior device portion 2315 of vaginal light therapy insert 2300 such that light exiting light guide 2305 at terminal end 2320 enters interior device portion 2315 to generate a light dominant-path, where more than 50% of light energy travels, at an optimum angle α2, which is configured to be greater than a critical angle for material from which vaginal light therapy insert 2300 is constructed. Variations of light guide 2305 placement and the resulting light transmission can be determined for a specific indication and/or patient need can be discerned by one of ordinary skill in the art without undue experimentation. As discussed previously, discontinuities can be incorporated into vaginal light therapy insert 2300, shown here as 2330 and 2335.

If vaginal light therapy insert 2300 is fabricated from a polycarbonate material with a refractive index of 1.6, for sections of vaginal light therapy insert 2300 outside of vaginal cavity 2105 when a majority of vaginal light therapy insert 2300 is inserted in vaginal cavity 2105, the refractive index of air, the critical angle of acrylic to air is about 38 degrees.

As would be understood by one of ordinary skill in the art, a critical angle is the angle of incidence above which total internal reflection occurs. By configuring light guide 2305 to comprise a dominant light path angle α2 to be greater than about −38 degrees, the light entering interior device portion 2315 will substantially be reflected at interior surface 2335 so as to allow light beam 2340 to travel within and through interior device portion 2315 of vaginal light therapy insert 2300 to exit vaginal light therapy insert 2300 at 2345, for example. Such an arrangement has been found by the inventor herein to substantially minimize light energy loss from the portion of vaginal light therapy insert 2300 that is not located inside of the vaginal cavity 2105 during use.

Yet further, using the same example of vaginal light therapy insert device 2300 being fabricated from acrylic, a dominant light path angle α2 can be provided to be less than the critical angle of acrylic to water. In some aspects, the placement of light guide 2305 in interior device portion 2315 can be arranged to provide a light path configuration having the following formula to enhance the therapeutic benefits of light energy.

Light dominant path formula:

$$\alpha \text{ critical } A < \alpha 2 < \alpha \text{ critical } B$$

where α critical A is the critical angle the vaginal light therapy insert 2300 material to air and α critical B is the critical angle the vaginal light therapy insert 2300 material to vaginal mucosa. Such critical angle calculations are also applicable to one or more other LLLT treatment applications according to the inventions described herein.

Referring to FIG. 23, in a further aspect of the present invention with optical arrangement conforming to the above formula, light beam 2340 can travel along a dominant path upon exiting light guide 2305 at 230. When used inside a vagina mucosa with a refractive index of about 1.23 with more than about 15% less than the refractive index of vaginal light therapy insert 2300, total internal reflection of light becomes possible with a critical angle of about 54 degrees. Upon light beam 2340 reaching interior surface 2345, light beam 2340 will be reflected back into interior device portion 2315. When light beam 2340 reaches insert surface 2345, a portion of light beam 2340 can enter the vaginal cavity tissue [not shown] for therapeutic effect. Configuration of the light guide 2305 and associated light beam 2340, in conjunction with the LLLT dosage provided from PBM control module 2130 can substantially reduce loss of light energy in light beam 2340 when traveling through interior device portion 2315 for subsequent delivery to a patient. Alternatively, a cladding/scattering layer [not shown] can be incorporated proximal to interior surface 2345 to further distribute the light substantially evenly over the mucosa tissue.

Alternatively, when light scattering cluster particles or air bubbles are introduced to vaginal light therapy insert device 2300, α2 can deviate from the light dominant path formula:

$$\alpha \text{ critical } A < \alpha 2 < \alpha \text{ critical } B$$

For example, light beam 2340 can be directed at a cluster of light scattering particles 2335 to generate a more randomized beam pattern for light delivery to patient tissues [not shown]. Further, when the surface of vaginal light therapy insert 2300 is covered by a cladding material [not shown] with refractive index different than α critical A or α critical B, α2 can be optimized for delivery to desired target tissue areas.

Figure 24:
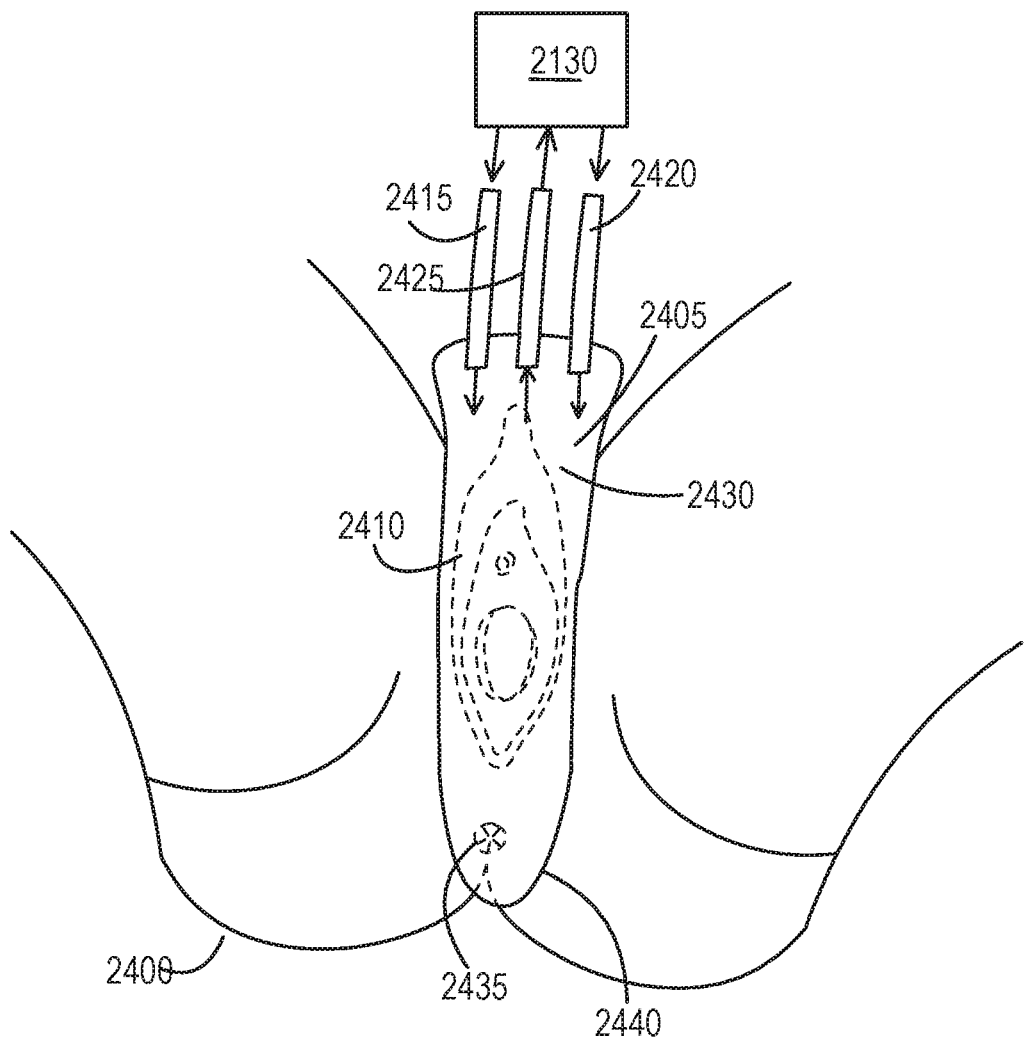
FIG. 24 illustrates an implementation of a light therapy delivery liner in a patient in need of treatment.

FIG. 24 illustrates the relative position of patient 2400 to light therapy delivery liner 2405 and the anatomic structure of at least vulvar region 2410, shown here with dotted lines. Patient 2400 is wearing light therapy delivery liner 2405 that incorporates first light guide 2415, optionally, second light guide 2420 and third light guide 2425, which can be used to deliver additional energy or light at a different wavelength than light delivered via 2415, or to transmit light from the light therapy delivery liner 2405 to associated sensors [not shown] for analysis. Light therapy delivery liner 2405 has a first side 2425 [not shown] proximal to vulvar region 2410, from which light therapy is delivered thereto. First side 2425 [not shown] can be in direct contact with vulvar region 2410, or a bandage [not shown] or absorbent material [not shown] can be located between first side 2425 [not shown] and vulvar region 2410. As would be recognized, any such bandage or absorbent material should be light transmissive to allow light therapy to be suitably applied to vulvar region 2410. Second side 2430 will be proximal to the patient's undergarments etc. in use. Second side 2430 is optimally configured to substantially prevent light from exiting therefrom, so as to minimize light loss. Accordingly, second side 2430 can be coated with an optically opaque and reflective material. Still further, second side 2430 can be coated or otherwise treated with a semi-reflective material.

Light guide 2415 and (if present) light guides 2420 and 2425 are operationally and optically engaged with light therapy delivery liner 2405 and PBM control module 2130. When light therapy delivery liner 2405 is placed proximal to vulvar and anal area, light energy can be delivered from PBM control module 2130 to help accelerate wound healing resulting from sex reassignment surgery, laceration or episiotomy from baby delivery or other forms of injury, such as infection, which can occur in vulvar region 2410, or hemorrhoids that can occur in anal region 2435. Note that light therapy delivery liner 2405 is shown with extended length to cover both vulvar region and anal region 2435, however, if treatment is for the vulvar regions only, the length will be shorter. Shape and size can be selected to provide optimum fit for a patient, and the condition being treated.

Figure 25A:
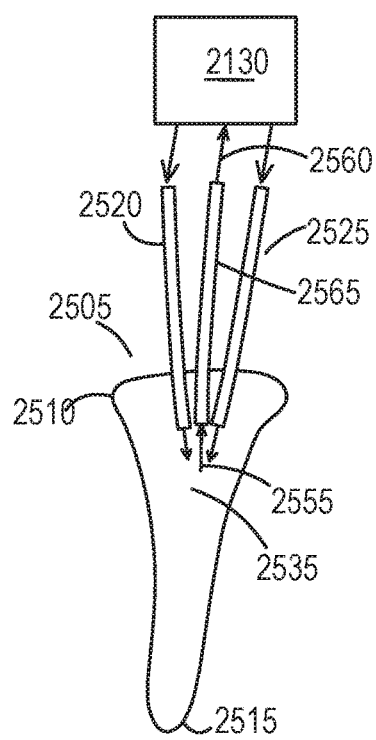
FIGS. 25A-25C illustrate different views and configurations of a light therapy delivery liner.
Figure 25B:
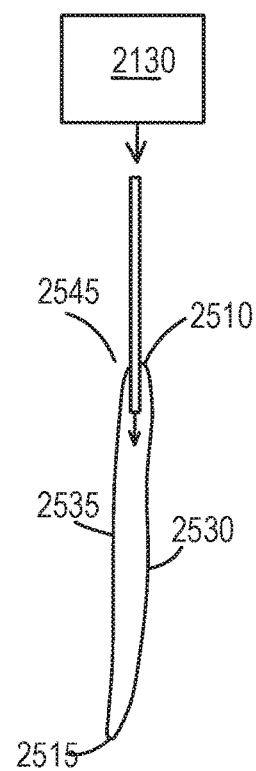
Figure 25C:
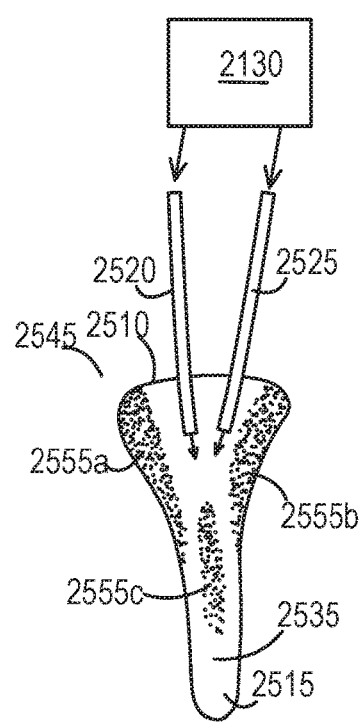

FIGS. 25a, 25b, and 25c illustrate light therapy delivery liner configurations that can be placed proximate to female vulva area to accelerate healing, reduce pain, and swelling. Referring to FIG. 25a, the size and shape of light therapy delivery liner 2505 can be selected to conform to an identified patient vulvar region shape and size, such as having a wider rear portion 510 (which may be worn proximate to the patient's vulva region 2410 or anal region 2435 or shorter as needed for a specific therapeutic configuration) and a narrower front portion 2515 (which may be worn proximate to the patient's clitoral region). Generally, light therapy delivery liner 2505 can be configured to approximate an elongated triangle shape with a contoured edge so as to improve comfort and wearability. First side 2530 [not shown], which is, in use, placed proximal to the patient's vulvar region 2410 and, optionally, anal region 2435, is configured to allow light to be delivered from PBM control module 2130, where that light source is in operational and optical communication with light guide 2520 and (optionally) light guides 2525 and 2565, which can be used to deliver additional energy or light at a different wavelength than light delivered by light guide 2520, or to transmit light beam 2555 from light therapy delivery liner 505 as beam 560 back to sensors [not shown] associated with PBM control module 2130 for analysis to determine, for example, tissue condition, treatment progress, compliance and dose-response.

Wearability and patient comfort can be enhanced by using a softer (with Shore A Hardness of about 30 or less) material to fabricate light therapy delivery liner 2505 for example. In one aspect of the present invention, Light therapy delivery liner 2505 can be configured from optically clear silicone rubber with a Shore A hardness of greater than about 0 to about 30.

Referring to FIG. 25b, 2545 is a side view of light therapy delivery liner 2505, where first side 2530 is shown as contoured along the length thereof, and first end 2515 is shown terminating in a somewhat curved configuration so as to enhance comfort in wearability.

Referring now to FIG. 25c, light therapy delivery liner 2550 incorporates surface or imbedded discontinuities 2555a, 2555b and 2555c to enhance light scattering, which can be beneficial in some implementations. In one aspect of the invention, discontinuities can be provided by impregnating particles in the surface of light therapy delivery liner 2550. In another aspect, discontinuities 2555a, 2555b and 2555c can be generated by etching the mold with sand or other particle-type etching to achieve discontinuity configurations desirable for light scattering. Discontinuity areas 2555a, 2555b and 2555c, as well as any other discontinuity configurations that might be appropriate for a patient treatment or device functionality, can be configured to increase or enhance the light exiting light therapy delivery liner 2545 for treatment of vulvar tissues and, optionally, anal tissues. As an example of the selective scattering applications, discontinuity areas 2555a and 2555b are configured to provide light energy to the groin regions of the patient in use, especially to the area with lymph nodes and blood vessels near the pelvic area, which can function as "healing vital areas," as discussed previously. Discontinuity area 2555c can enhance healing of the area proximal to the vaginal opening.

As examples for treatment method to vulva region 2410 with light therapy delivery liner 2550, light can be introduced to region 2410 at a dosage of from about 0.3 to about 5 Joule/cm$^2$/day with red wavelengths of from about 650 nm to about 700 nm and about 830 nm to about 980 nm in the infrared range immediately post-surgery or shortly after childbirth to promote healing during the early stages of recovery and to reduce pain and swelling. The wavelengths associated with green, from about 510 nm to about 530 nm, can be administered at about 0.3 to about 3 Joule/cm$^2$/day, intermittently or simultaneously with other wavelengths, or can be used for treatment of vaginal or vulva area rejuvenation, overactive bladder (OAB) syndrome, vaginismus or vulvodynia, conditions that can be associated with patients needing therapeutic assistance. For an actually or potentially infected area during wound healing, the wavelengths associated with blue, from about 410 nm to about 495 nm, can be used with at about 10 to about 70 mW/cm$^2$.

In another aspect of the present invention shown in FIG. 26a, vaginal light therapy insert 2600 can be operationally configured with a light source 2605, controller 2610, associated housing 2615 and removable battery 2620 proximal to an anterior end 2625 of vaginal light therapy insert 2600. Vaginal light therapy insert 2600 is configured from optically clear material. Light source 2605 can be a LED or other suitable light source that is configurable emit a therapeutic wavelength of light. In use, light source 2605 emits light with desired wavelength into and through the optically clear interior potion 2630 to be emitted from outer surface 2635. Discontinuities 2640 can optionally be incorporated in one or more locations on vaginal light therapy insert 2600 to enhance light scattering.

In FIG. 26b, vaginal light therapy insert 2645 incorporates LED 2605 or other suitable light source, LED 2650 is operationally connected via wire 2660 to controller 2665, which is powered by or connected to battery power [not shown] and can have wireless communication capabilities [not shown] such as Bluetooth® or WiFi. As illustrated, connection 2670 is removably engagable with controller 2665, but such connection can be permanent, as appropriate. Discontinuities 2640 and 2675 can be incorporated as discussed herein in any portion of the devices illustrated in FIGS. 26a and 26b. Vaginal light therapy inserts 2600 and 2645 each, independently, can further be configured with sensors 2680 and 2685 that are in operational engagement with the respective controllers 2610 and 2665.

Figure 27:
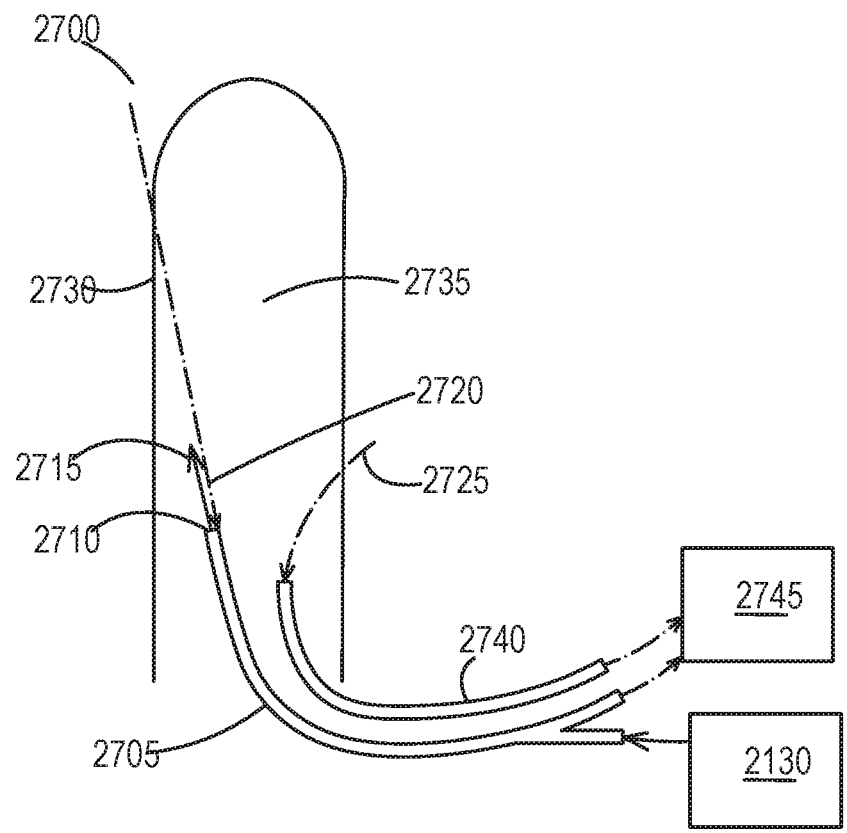
FIG. 27 illustrates a further implementation of an insertable vaginal light delivery device.

Referring to FIG. 27, Vaginal light therapy insert 2700 is configured with light guide 2705 from which therapeutic light is emitted at 2710 as light beam 2715, which provides therapeutic light when it reaches the patient's vaginal tissue [not shown]. Light guide 2705 is in operational and optical communication with PBM control module 2130. When inserted in a vaginal cavity [not shown] and the treatment process is underway, the patient's vaginal tissue [not shown] condition, such as temperature, infection, oxygen level, dryness, wetness, coloration, smoothness, and others can be analyzed in various methods, such as with reflected light, or emitted light of one or more wavelengths from bioluminescence or fluorescence associated with the healing process. Light detection from vaginal cavity 2105 during healing, here shown for simplicity as tissue reflected or emitted beam 2720 and tissue reflected or emitted beam 2725 can travel through outer device surface 2730 into interior 2735 for collection by light guides 2710 and 2740. Such collected light beams 2720 and/or 2725 are transmitted to analysis device 2745, which can be a photodetector or other suitable sensor-containing equipment, to evaluate the healing level and effectiveness of the relevant area. FIG. 27 is shown with two light guides, 2705 and 2740, where 2705 can be used to both emit LLLT and to collect light from the vaginal cavity tissue, however, other configurations are contemplated.

Figure 28A:
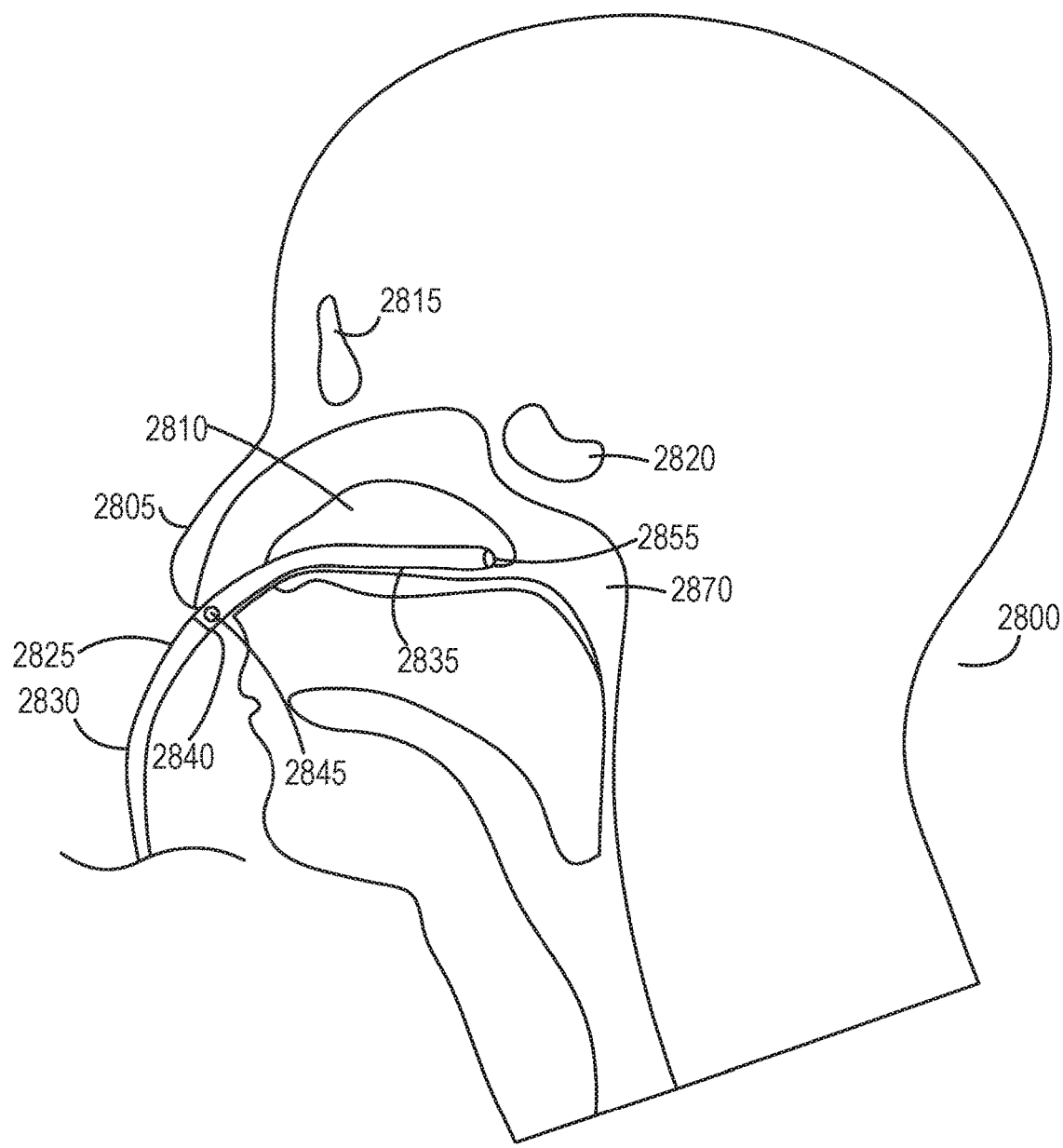
FIGS. 28A-28C illustrate a LLLT device for treatment of a nasal cavity and proximal regions.
Figure 28B:
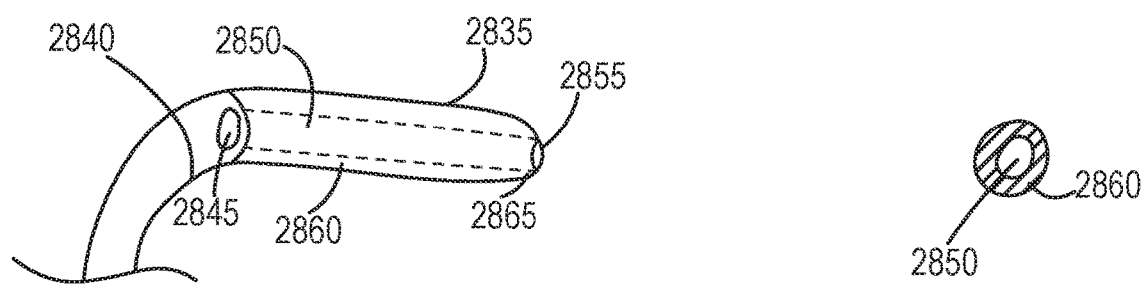

FIG. 28 illustrates a further implementation of a LLLT treatment device for use in nasal area surgery. Patient 2800 having nose 2805, nasal cavity 2810 and sinus area cavities 2815 and 2820 is shown with wearable nasal LLLT treatment device 2825 inserted in nasal cavity 2810. Nasal LLLT treatment device 2025 has first light transmission portion 2830, which can be, for example, a fiber optic suitable to transmit light from PBM control module [not shown] when 2830 is suitably engaged therewith. Use of a fiber optic can combine flexibility for patient 2800 comfort with efficient light transmission through portion 2830. First light transmission portion 2830 can also comprise a polymeric material capable of total internal reflection or is suitably coated so as to substantially prevent light transmission from portion 2830 prior to entry thereof into nasal cavity 2810. Nasal LLLT treatment device 2825 has second light transmission portion 2835 that, in use, extends inside nasal cavity 2810. Light transmission portions 2830 and 2835 are removably engaged with each other at connection 2840, as discussed further in relation to FIG. 29, for example. Light transmission portions 2830 and 2835 can, when assembled to allow light to travel within the assembled structure, and suitably comprise "light guides" or "light guide arrangements" in accordance with the present invention.

To enhance patient comfort in use, second light transmission portion 2835 should be configured from a flexible material, such as a silicone polymer or other polymeric material having a Shore A hardness of from about 20 to about 65. The air passage within 2835 should be structured to remain open when materials of different hardness are used.

Second light transmission portion 2835 is configured to be inserted into nasal cavity 2810 substantially immediately after a surgical procedure, such as a rhinoplasty or sinuplasty, and to stay in place for at least some of the healing process post-surgery. Patient 2800 can be assisted in breathing by addition of an opening 2845 located in the wall of second light transmission portion 2835, such as at a location exterior to nose 2805. At all times, including when 2830 is not engaged with second portion 2835, opening 2845 is in communication with internal diameter 2850 configured within second light transmission portion 2835 to terminate in end 2855, where end 2855 is positioned in nasal cavity 2810 in use to enable sufficient air flow to and from the nasal cavity 2810 to facilitate the normal breathing of patient 2800.

Figure 28C:
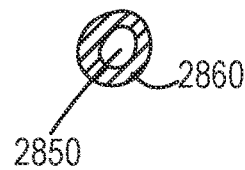

Engagement of 2830 with 2835 completes a light guide arrangement path 2860 that allows light to travel from a PBM control module [not shown] through portion 2830 and into second light transmission portion 2835 so as to provide LLLT treatment to nasal cavity 2810 and, in some implementations, sinus area cavities 2815 and 2820. A cross-section of second portion 2835 is shown in FIG. 28c, which shows interior diameter 2850 that allows air to travel through to facilitate patient 2800 breathing, while still allowing light to reach 2810 etc. from light guide arrangement path 2860. In some aspects, light guide arrangement path 2860 can comprise a reflective interior coating and/or an angle of at less than about 85 degrees can be configured into end 2865, to assist in light being reflected into light guide arrangement path 2860 to provide light emission to nasal cavity 2810. In other aspects, light guide arrangement path 2860 can comprise a reflective exterior coating and/or end 2865 with no or partial coating, to provide light emission from end 2865 to the nasophanyx region 2870 of the nasal cavity 2810 for treatment.

Figure 29A:
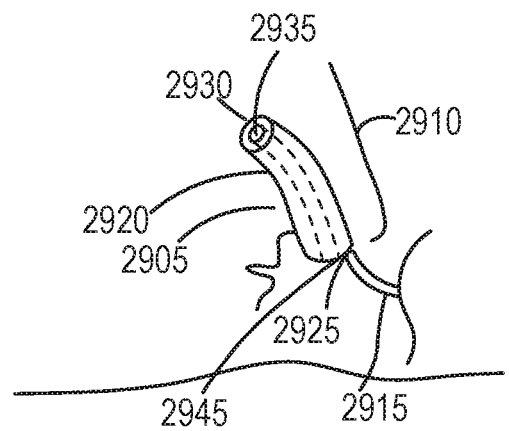
FIGS. 29A-29B illustrate componentry for use in a LLLT device for treatment of a nasal cavity and proximal regions.
Figure 29B:
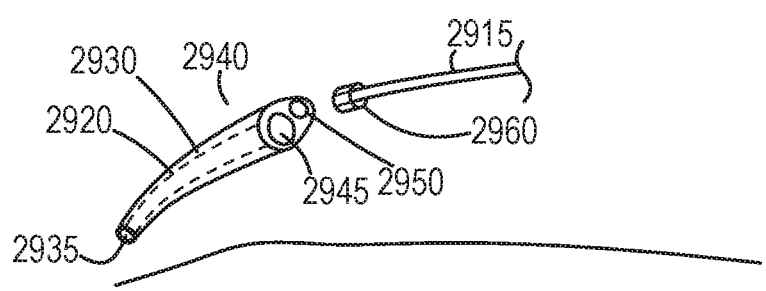

FIGS. 29a and 29b illustrates a configuration of a nasal LLLT device of the present invention. In FIG. 29a, assembled nasal device 2905 is shown placed in patient nose 2910. First light transmission portion 2915 is engaged with second light transmission portion 2920 at connection 2925. In use, first light transmission portion 2915 is in operational and optical engagement with a PBM control module [not shown]. Second light transmission portion 2920 is shown with interior diameter 2935 for allowing air to flow into patient's nose 2910 when second light transmission portion 2920 is engaged with first light transmission portion 2915.

As shown in FIG. 29b, first and second light transmission portions 2915 and 2920 can be in an unconnected configuration 2940. Opening 2945 is proximal to magnetized portion 2950 whereby first light transmission end 2960 is magnetically engageable therewith. Use of a magnet as shown herewith has been found to enhance operability and patient compliance by enabling connection 2925 between portions 2915 and 2920 to be created and broken easily and substantially without requiring twisting or snapping action that might result in pain to patient or disruption of healing processes.

Figure 30A:
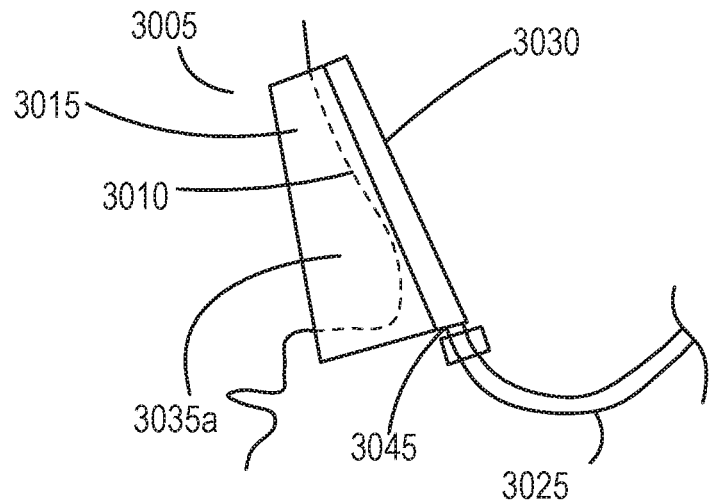
FIGS. 30A-30B illustrate a LLLT device for treatment of a bridge of a nose.
Figure 30B:
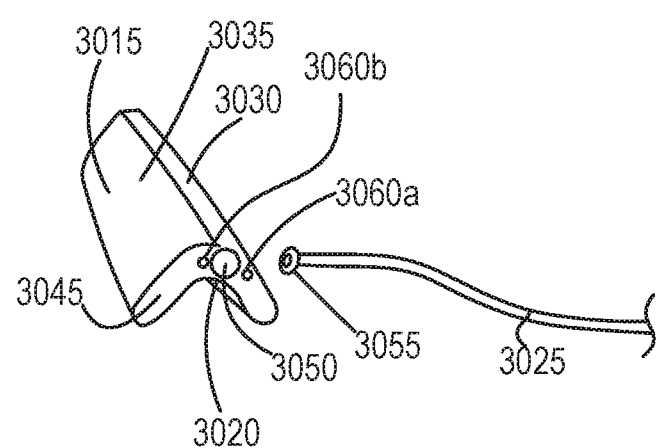

FIGS. 30a and 30b illustrate a nasal LLLT treatment device 3005 that is placeable over patient's outer nose 3010 in conjunction with a septoplasty or rhinoplasty, for example. Device 3005, which is suitably fabricated from bio-compatible material that is light transmissive, has support structure 3015 having inner surface 3020 that remains light transmissive, wherein 3015 is shaped to fit over patient's nose 3010. First light transmission portion 3025 can be a fiber optic component or the like, as discussed previously. Second light transmission portion 3030 has first exterior side 3035 and second exterior side 3040 [not shown] that are reflectively coated to reduce light exiting from sides 3035 and 3040. Together, 3035 and 3040 approximates the shape of the bridge [not shown] of nose 3010. Device 3005 has connection 3045 configured to engage with support end engagement port 3050. Connection 3045 is made by engagement of first transmission portion end 3055 with engagement port 3050 to allow light to be transmitted into support structure 3015 in use. Engagement port 3050 can be magnetized by including magnets, such as shown in 3060a and 3060b, proximal to engagement port 3050. First transmission portion end 3055 can comprise suitable material to be magnetically engageable with engagement port 3050. When first light transmission portion 3025 is suitably engaged with support 3015 to form connection 3045 and portion 3025 is operationally and optically engaged with a PBM module [not shown] LLLT will be emitted to areas proximal to the skin and bridge [not shown] of nose 3010.

FIG. 31 illustrates an implementation for a nasal insert 3105 configured to distribute LLLT treatment to areas proximal to the nostrils [not shown] and nasal cavity [not shown] and keep the airway path [not shown] from closing by providing support to the surrounding tissue [not shown], such as after a rhinoplasty, for example. Nasal insert 3105 comprises a first nasal insert portion 3110 configured to be engagable with a first light transmission portion [not shown], which can be fiber optic, that is configurable to transmit light from a PBM control module [not shown] via suitable connections [not shown]. First nasal insert portion 3110 can be cladded with material, such as a polymer of lower refractive index or via metal vapor deposition to be substantially non-transmissive to light. First nasal insert potion 3110 is engageable at end 3115 with second nasal insert portion 3120 at second nasal insert portion end 3125. Second nasal insert portion, made from light transmissive material, has first nasal stem 3130 and second nasal stem 3135 from which LLLT treatment can be delivered when nasal insert 3105 is configured for use. First and second nasal stems 3130 and 3135 are engaged at bend 3140. First nasal stem end 3130 is configured with air hole 3150 in communication with air hole 3160. Second nasal stem 3135 is configured with air hole 3155 in communication with air hole 3165.

Figure 31A:
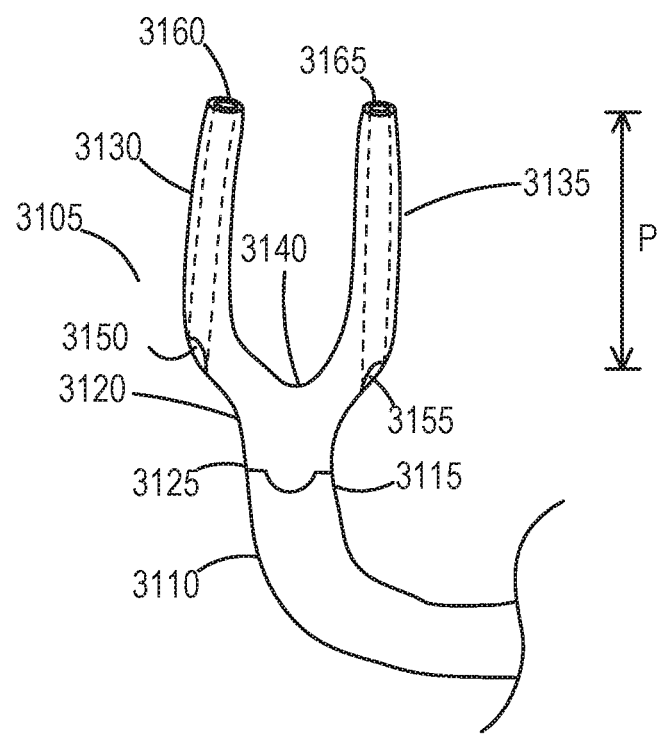
FIGS. 31A-31B illustrate componentry for use in a LLLT device for treatment of a nasal cavity and proximal regions.
Figure 31B:
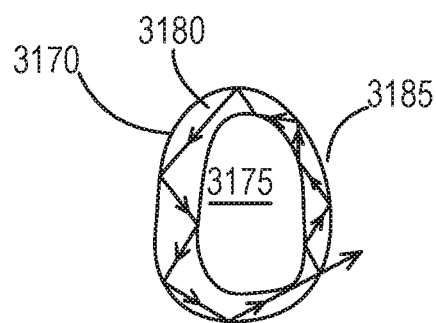

FIG. 31b illustrates a cross section 3170 of a nasal stem in accordance with FIG. 31a whereby inner diameter 3175 is configured to allow air flow in use, and the area 3180 between inner diameter 3175 and outer diameter 3170 is configured to allow light to travel therein and to exit at surface 3185, for example, to allow patient nasal tissue [not shown] to be suitably treated with LLLT treatment in use. Nasal insert 3105 is sized for patient comfort while still allowing suitable LLLT treatment. In this regard, nasal stems 3130 and 3135 can be configured from flexible material having light transmission functionality therefrom, such as silicone polymer having a Shore Hardness of from about 20 to about 65.

Figure 32A:
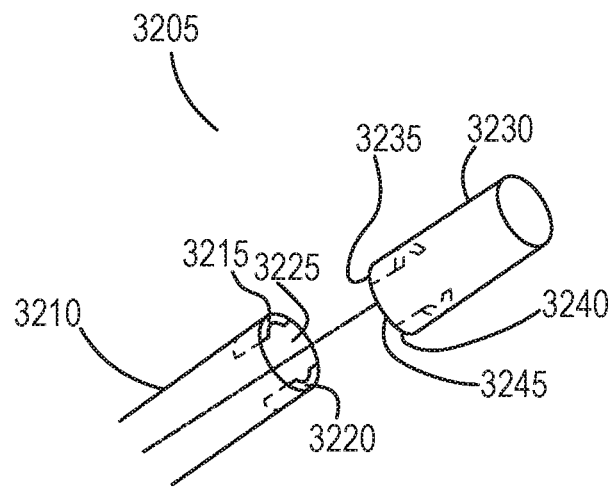
FIGS. 32A-32B illustrate connection of LLLT componentry via an optical connector.
Figure 32B:
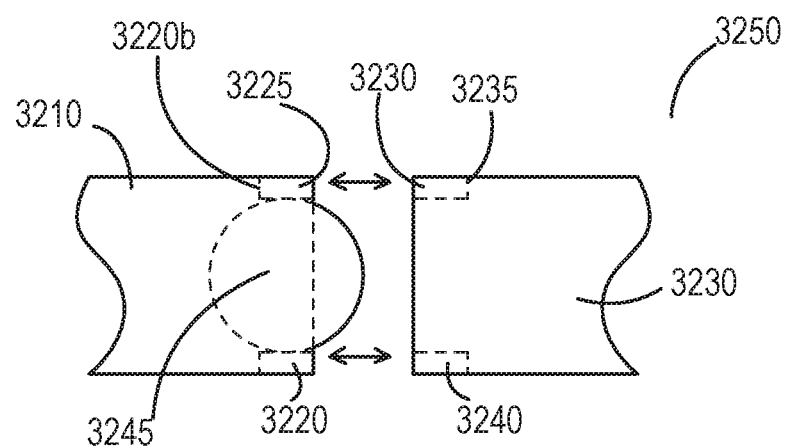

FIGS. 32a and 32b show a quick connect and low loss optical coupling connector for providing treatment dosage to a PBM control module to for delivery to a patient. In one application with an engagement configuration 3205 for connecting light guide sections 3210 and 3230. Engagement configuration 3205 has alignment features 3215 and 3220 configured within light guide interior 3225 and alignment features 3235 and 3240 configured within light guide interior 3245. Alignment features 3215, 3220, 3235, and 3240 are configured to assist in aligning light guide section 3210 and with light guide section 3230. In one aspect, the alignment is achieved by the location of magnets 3215 (N) and 3320 (S) to match the polarity of magnets 3235 (S) and 3240 (N). Other mechanical alignment can be used such as pin and hole arrangements. In FIG. 32b, engagement of light guides 3210 and 3230 is shown with optical connector core 3245, made of a pliable and light transmissive material, to generate an efficient optical coupling connection [not shown] by substantially eliminating or minimizing optical loss from air gaps at the point of connection. Such substantially air free connections generated from a pliable optical connector is used in this and other embodiments of the present invention.

Figure 33:
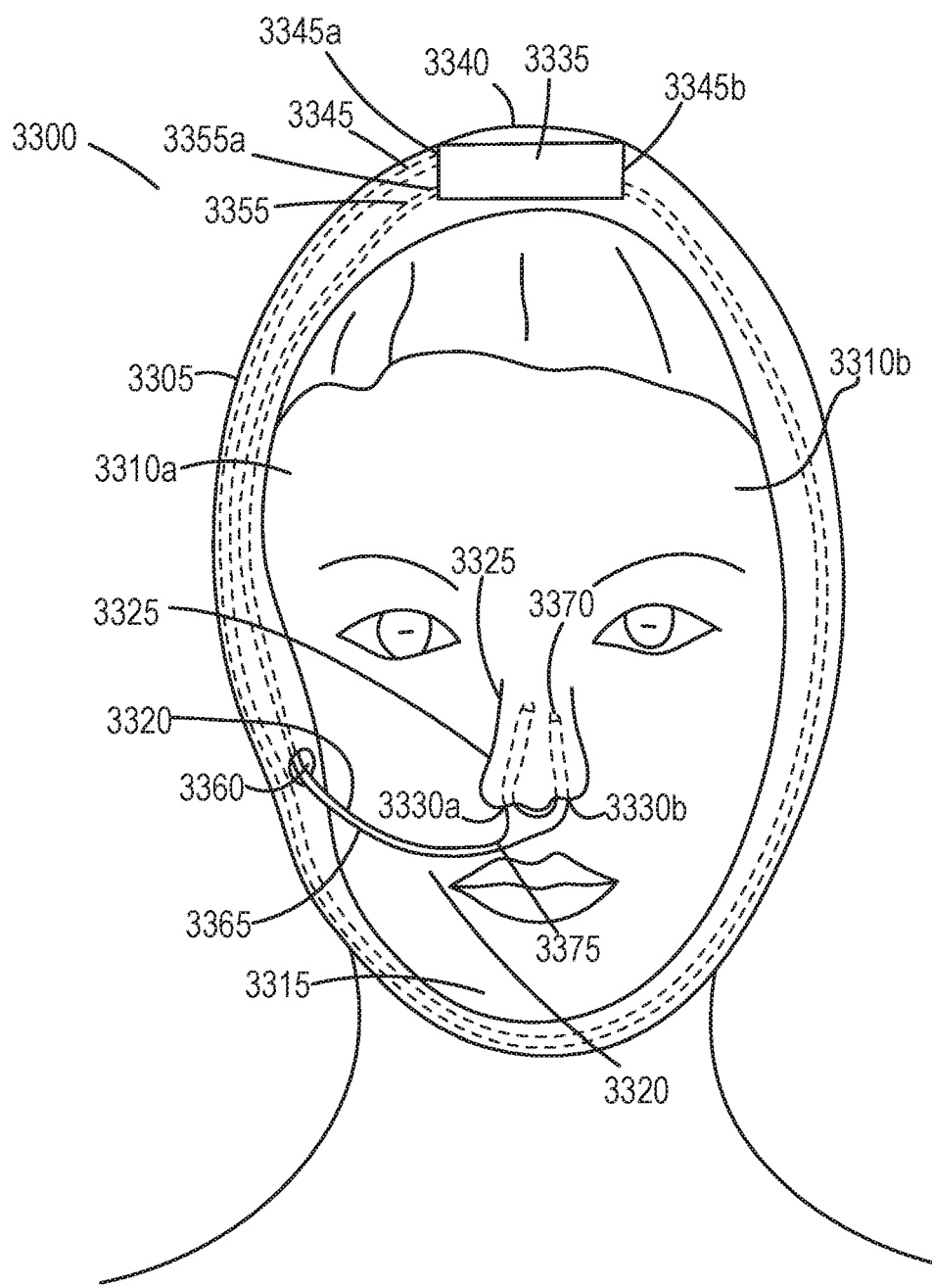
FIG. 33 illustrates componentry for use in a LLLT device for treatment of facial and nasal cavity regions.

FIG. 33 illustrates a combination LLLT treatment comprising a patient 3300 with a first LLLT treatment device 3305 configured around patient head sides 3310a and 3310b and chin 3315 in conjunction with nasal LLLT treatment device 3320 configured in patient nose 3325 within nostrils 3330 and 3330b. PBM control module 3335 can be positioned proximally to patient crown 3340, for example, or other suitable area. Light guide arrangement 3345 is engaged at engagement port 3345a via optical connector [not shown] with PBM control module 3335 so as to deliver a dosage of LLLT treatment to patient 3300 from patient facing side 3350 [not shown] of treatment device 3305 at head side 3310a around chin area 3315 to head area 3310b to be further engagable with PBM control module 3335 at 3345b. Light guide arrangement 3355 is engageable with PBM control module 3335 at 3355a and configured to engage with connection 3360 which is, in turn, engaged with first light transmission portion 3365, which can be a fiber optic. Light transmission portion 3365 is engaged with nasal insert 3370 at connection 3375 to provide a path for LLLT treatment as detailed elsewhere herein when nasal insert 3370 is inserted into patient nostrils 3330a and 3330b and PBM module 3335 is operationally and optically engaged therewith. As shown, one PBM control module and a plurality of light guide arrangements 3345 and 3355 are configured with 3305, but different PBM control module and light guide arrangements are contemplated.

Figure 34A:
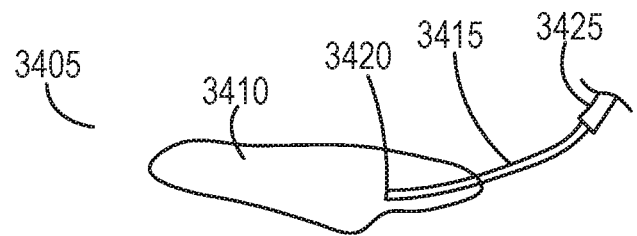
FIGS. 34A-34D illustrate componentry for use in a LLLT treatment device having cooling or cushioning functionality.

FIG. 34a illustrates a LLLT treatment device configuration 3405 comprising a treatment component 3410 fabricated from a substantially soft material, such as that having a Shore A hardness of greater than 0 to less than about 30. Component 3410 is fabricated from a light transmissive material, such as silicone polymer. Light transmission portion 3415, which can be a fiber optic or polymeric light guide, has interior end 3420 embedded in component 3410 for distributing LLLT treatment therefrom for further transmission into and from an interior [not shown] of component 3410. Light transmission portion 3415 is operationally and optically engageable to a PBM control module [not shown] via connection 3425.

Figure 34B:
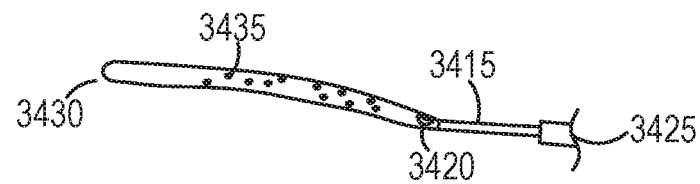
Figure 34C:
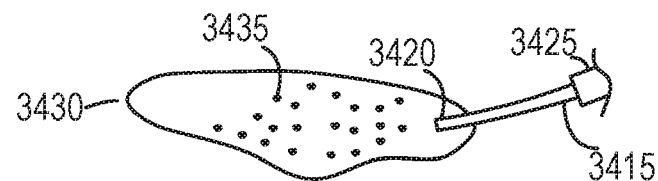

FIGS. 34b and 34c show a variation 3430 having discontinuities 3435 in component 3430 that function to scatter light from 3430. Such discontinuities 3435 can be in the interior of 3430 and/or can be placed on the surface of 3430. FIG. 34b is a side view, and FIG. 34c is a top view of 3430, each of which show exemplary placement of discontinuities 3435.

Figure 34D:
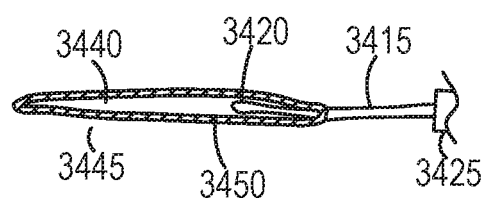

In a further variation, FIG. 34d shows a clear liquid or gel filling is incorporated in an interior area 3440 of component 3445 to provide a soft and resilient (e.g., "pillow-like") feel thereto. Light transmission portion 3415 having end 3420 is operationally and optically engaged with a PBM control module [not shown] via connection 3425. Component 3445 can be fabricated from a soft material that is light transmitting. An optical fiber interior end 3420 is incorporated in 3440 and in contact with exposed to the liquid or gel filling therein. Surface discontinuities [not shown] for light scattering can be incorporated in either or both the interior 3440 or in the surface 3450 of component 3445. Such design can be beneficial as water or gel is highly transmissive and conforms well with complex body contours, such as on the face to provide comfort, and can be used in combination with hot and cold therapy to the same area, for example.

Figure 35A:
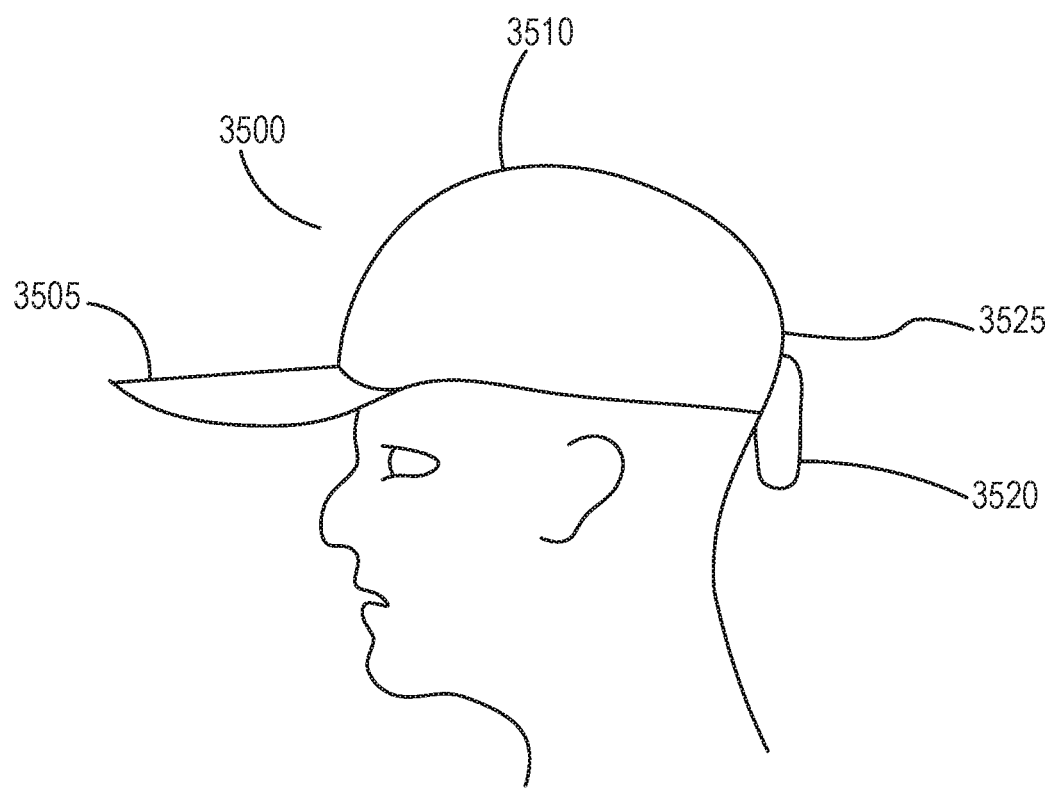
FIGS. 35A-35B illustrate a configuration of a LLLT device for scalp area treatment.
Figure 35B:
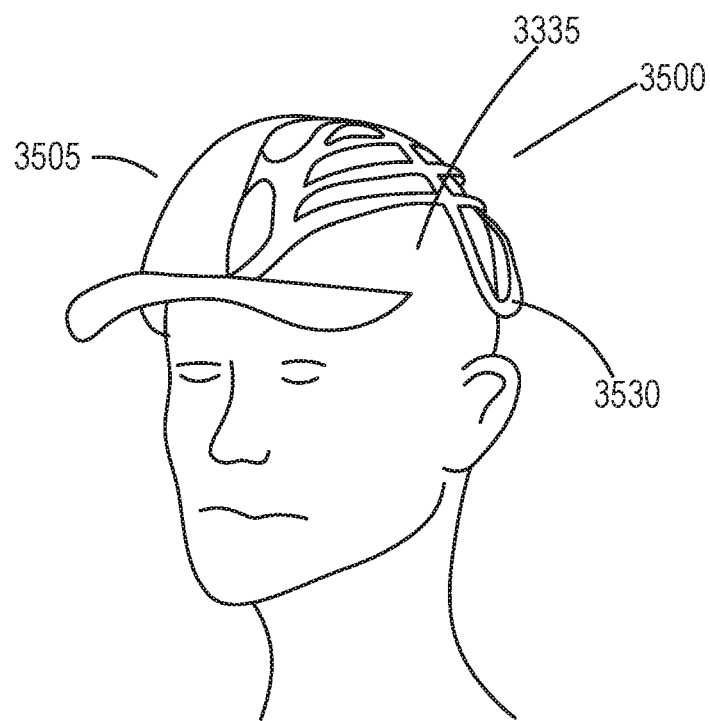

A LLLT treatment device for human head hair growth, restoration and/or scalp healing (collectively scalp LLLT treatment device) is illustrated in FIG. 35a. Patient 3500 is wearing LLLT scalp treatment device 3505 having an exterior surface 3510 and a scalp facing side 3515 [not shown]. PBM control module 3520 is configured to be removably mountable or permanently mountable to cap 3505, such as at a rear portion 3525. PBM control module 3520 is operationally and optically engageable with light guide arrangement 3330, here shown with cap 3505 partially cut away in FIG. 35b. Light guide arrangement 3330 is configured to treat substantially most or all of scalp 3335 with LLLT treatment being delivered from a patient facing side 3340 [not shown] of light guide arrangement 3330. As shown, scalp LLLT treatment device 3505 is configured as a baseball cap, however, it is to be understood that any cap or hat configuration can be used, as long as the intended scalp LLLT treatment can be effected therefrom. PBM control module 3520 is visible as a housing at rear portion 3525 in FIG. 35a. However, more discrete configurations, such as with a smaller format PBM control module design [not shown] or by embedding various componentry in a flexible housing [not shown] that could be fully hidden inside cap 3505.

Notably, unlike prior art hair growth/restoration LLLT hat configurations, the LLLT treatment is delivered via light guide arrangement directly and with substantially no electrical connections are in contact with the scalp or areas proximal thereto. Still further, the light source(s) [not shown] are substantially separated from the location where the LLLT treatment is delivered to the patient's scalp, such as being configured to be wholly generated from a light source(s) that is incorporated in housing or other containment structure that is separate and connectable to a light guide arrangement configured to deliver LLLT therefrom.

Figure 36A:
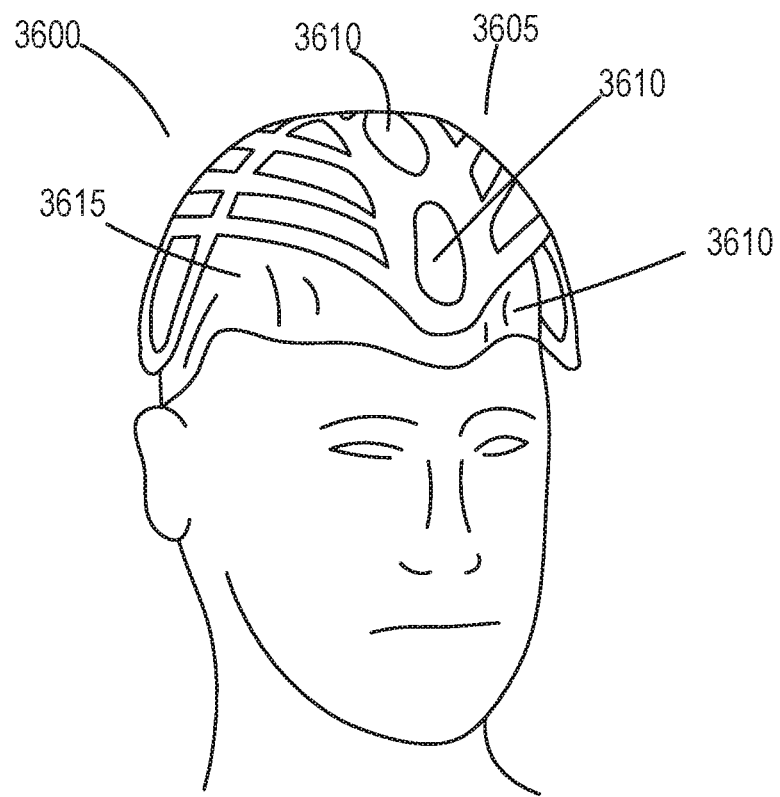
FIGS. 36A-36B illustrate a configuration of a light guide arrangement for use in a scalp area treatment.
Figure 36B:
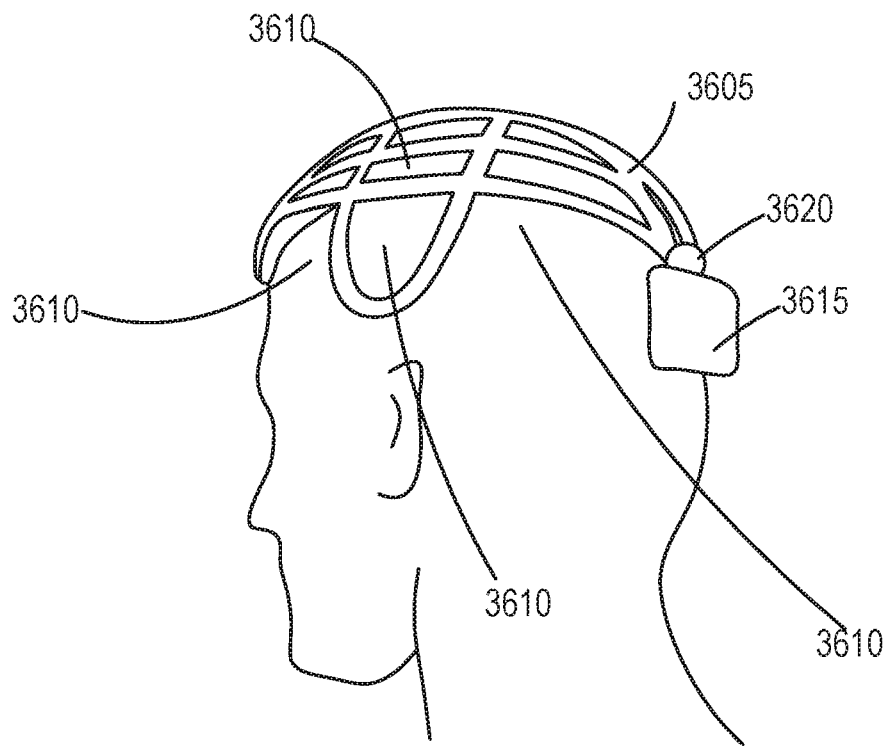

FIG. 36 illustrates an exemplary configuration of a light guide configuration to provide LLLT treatment to patient 3600 with light guide arrangement 3605 positioned proximal to patient scalp area 3610. Light guide arrangement 3605 is configured to deliver light to substantially all of scalp area 3610 on patient 3600, as shown in FIGS. 36a and 36b. The light guide arrangement side 3605 facing away from the scalp area 3610 can be coated with optically reflective material, and the scalp facing side [not shown] can be configured to contact with or be adhered to light transmissive particles, synthetic microfibers, fiber segments, or can comprise surface discontinuities sufficient to cause light scattering during delivery of LLLT treatment to scalp 3610. In FIG. 36b, PBM control module 3615 is shown engaged with light guide arrangement 3605 at connection 3620.

Figure 37:
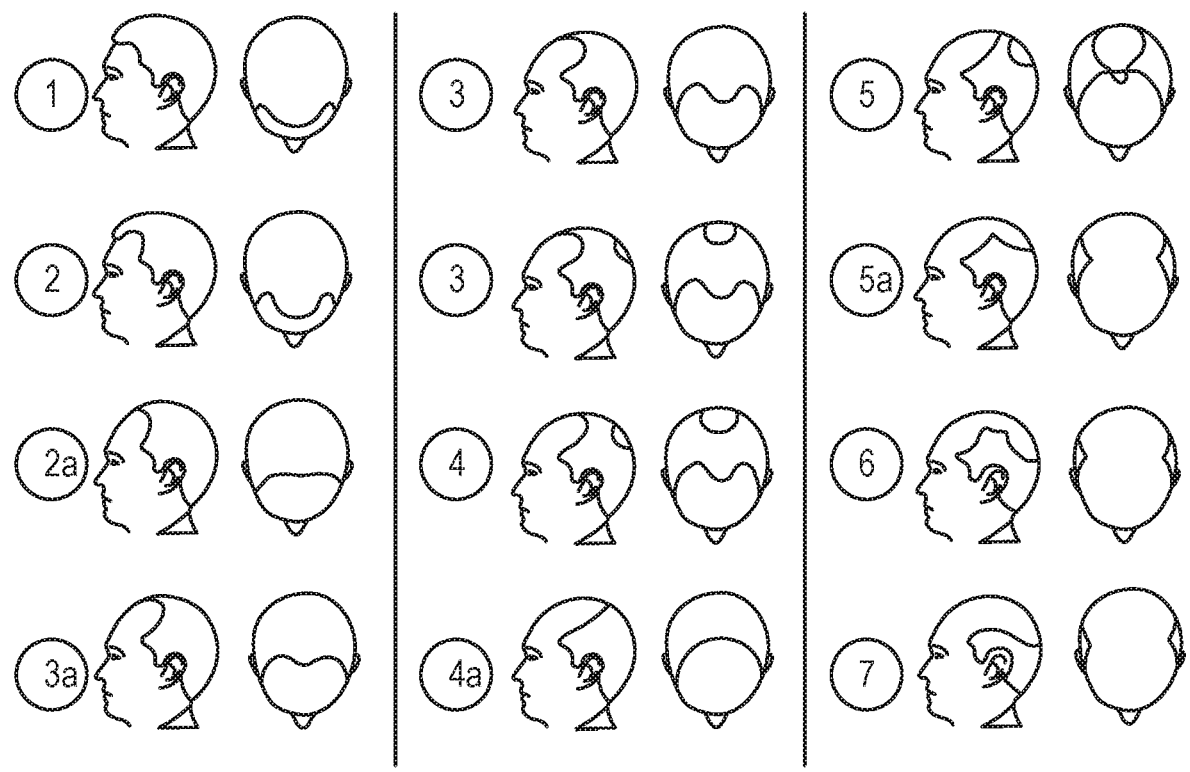
FIG. 37 illustrates the Norwood Scale of hair loss measurement (prior art).

FIG. 37 shows the Norwood Scale, which is a standardized prior art method for assessing for assessing the amount, type, and pattern of hair loss. In one aspect of the present invention, a patient's hair loss can be determined according to a standardized assessment such as the Norwood scale, and a light guide arrangement having a light delivery pattern appropriate to deliver LLLT treatment to the patient in substantially all locations associated with the determined hair loss.

Methodology associated with the present invention comprises selecting an amount of hair loss in a patient according to the Norwood Scale or other standardized methodology and defining a LLLT treatment protocol to provide a therapeutic treatment therefore. Beneficial dosages for promoting hair growth with red and/or near-infrared light wavelengths can be in the range of about 0.5 J/cm$^2$/day to 10 J/cm$^2$/day depending on the degree of hair loss, hair thickness, color of existing hair, and other factors. The non-invasive and discrete nature of the scalp area LLLT treatment device of the present invention allows the device to be worn as needed by a patient, thus enhancing the usability and effectiveness of the scalp treatment protocols in the present invention.

Figure 38A:
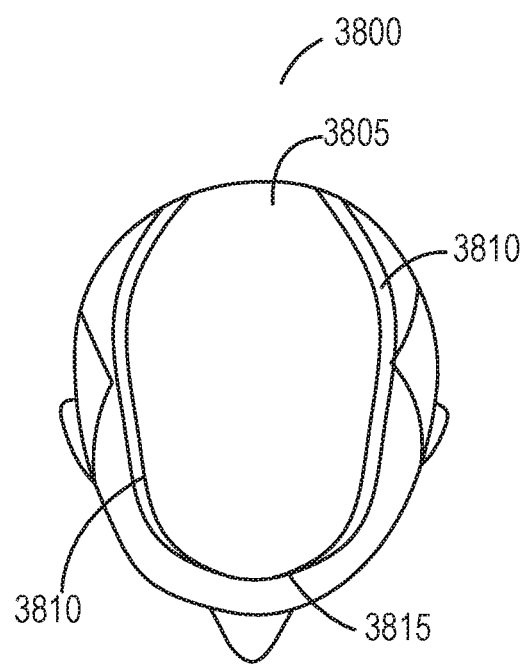
FIGS. 38A-38B illustrate a hair loss configuration and a light guide arrangement for treatment thereof.
Figure 38B:
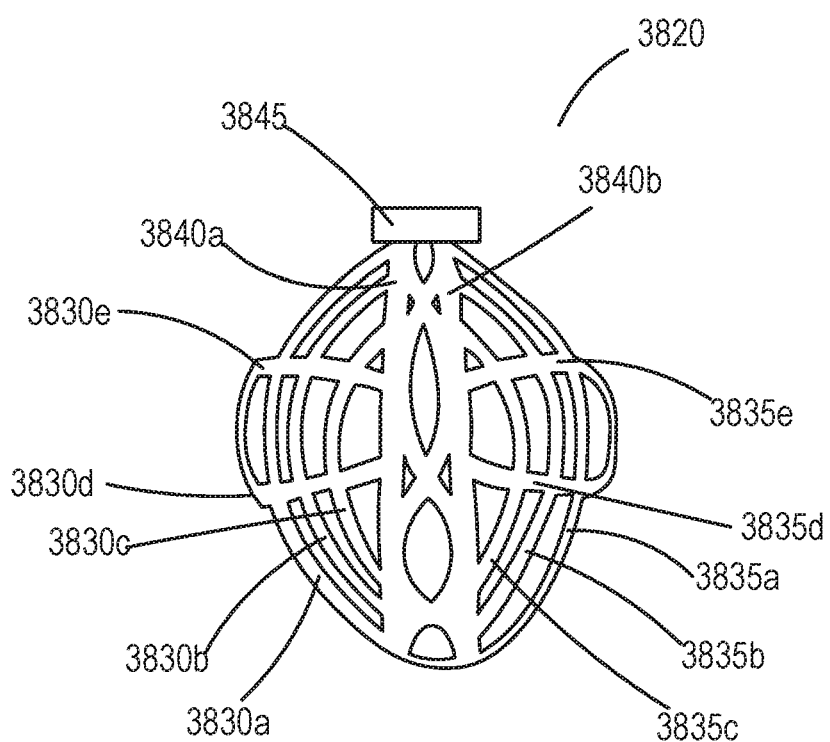

FIG. 38a shows patient 3800 having a level of male pattern baldness on the Norwood Scale as shown in FIG. 37 of about 5 as seen by the amount of scalp 3805 and forehead 3815 that are free of hair 3810 covering. FIG. 38b illustrates an exemplary light guide arrangement 3820 having a plurality of light guide arrangement elements 3830a, 3830b, 3830c, 3830d, 3830e, 3835a, 3835b, 3835c, 3835d, and 3835e configured with central light guide arrangements components 3840a and 3840b to delivery LLLT treatment to patient scalp area 3805 [not shown] in a pattern substantially similar to the determined degree of patient 3000's hair loss on a standardized scale, such as the Norwood Scale. Central light guide arrangement components 3840a and 3840b are removably or permanently engageable with PBM control module 3845 at engagement ports 3850a and 3850b [not shown]. Other light guide arrangements and engagements to one or more PBM control modules are contemplated.

Figure 39:
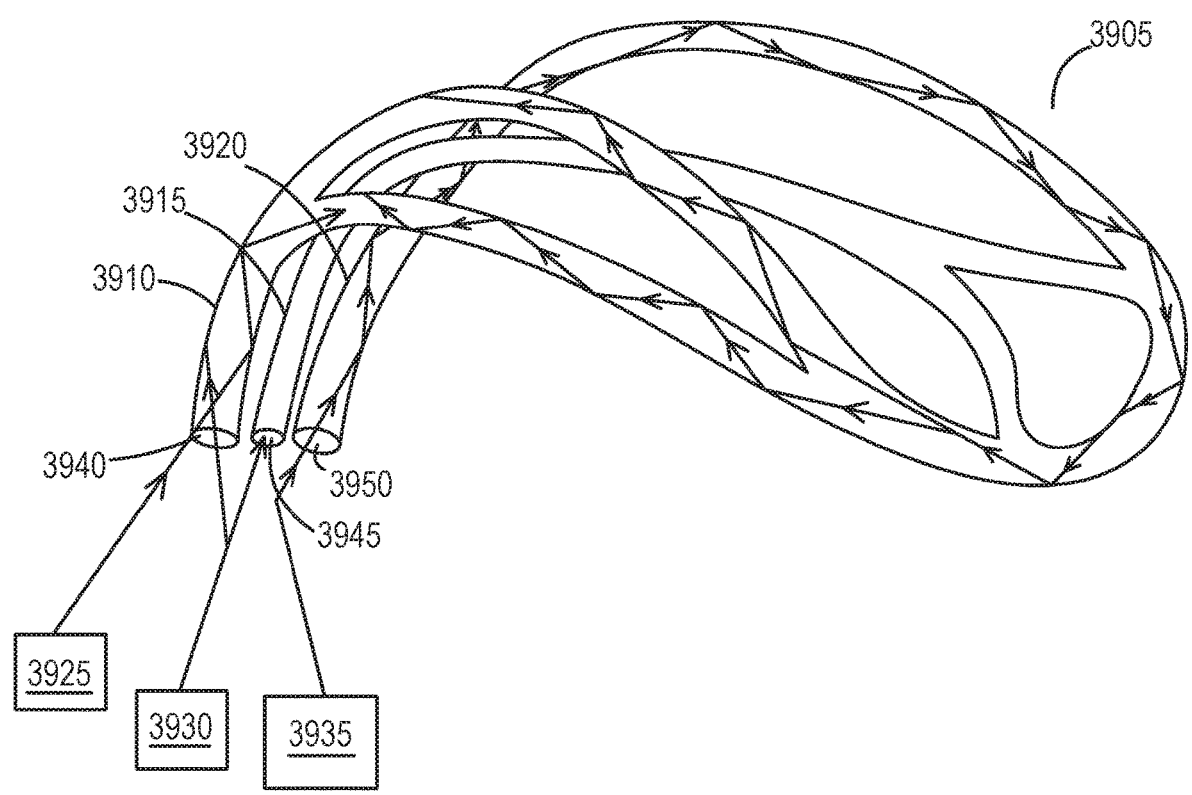
FIG. 39 illustrates a configuration of a light guide arrangement and light travel patterning therein.

FIG. 39 discloses a further implementation of a light guide arrangement 3905 that can be used to treat the scalp area of a patient [not shown] in need of treatment. Light guide elements 3910, 3915, and 3920 are configured to comprise light guide arrangement 3905 so as to deliver LLLT treatment to a substantial portion of a patient's scalp [not shown] in use. Light guide elements 3910, 3915, and 3920, which are in communication with each other at one or more locations, are operationally and optically engageable with light sources 3925, 3930, and 3935, which can be three lasers, LEDs or SLDs, for example. Such light sources 3925, 3930, and 3925 can be configured in a single PBM control module [not shown] or two or more PBM control modules [not shown]. When light guide arrangement 3905 is operationally and optically engaged with light sources 3925, 3930, and 3935 at light guide element ends 3940 3945, and 3950, a therapeutic amount of LLLT treatment is deliverable to a patient [not shown]. Use of more than one, such as two or three, light sources can be beneficial to better ensure that the entire patient scalp area is exposed to enough LLLT treatment while at the same time minimizing heat generation that could cause discomfort or overheat the componentry. In this regard, additional light sources can increase the total amount of light energy available to be distributed to the patient's scalp area during a treatment without requiring the use of a single light source that has enough power, and the associated power requirements therefore, to be able to fully distribute light through the full surface area of a light guide arrangement such as 3905. Such light energy is shown traveling through at least part of light elements 3910 and 3920. More or fewer light sources can suitably be used.

Light guide arrangement 3905 can be configured in various shapes from optically suitable polymer (such as TPX™ Polymethylpentene (PMP) from Mitsui Chemicals America, or Thermoplastic polyurethane (TPU)) or silicone (Dow Corning's line of optical moldable silicones) to achieve the objectives of the present invention. Side emitting fiber optics can also be used. Light guide arrangements can be custom designed for a patient by measuring the scalp area of a patient and fabricating a light guide arrangement that delivers LLLT treatment from a patient facing side thereof in an amount that covers substantially all of the surface area of the scalp area in need of treatment.

Light guide arrangement 3905 and any individual light guide elements, such as 3910, 3915, and 3920, associated therewith are configurable to substantially evenly distribute light to a patient's scalp for treatment thereof. In further implementations, one or more parts of light guide arrangement 3905 and associated light guide elements such as 3910, 3915 and 3920) are configurable for collecting the reflection of light from the scalp for analysis of treatment progress and dosage response. Progress of scalp area treatment can be monitored from time to time in this regard. In this regard, light guide arrangement 3905 can be engagable to a filtered photo-sensor [not shown] associated with PBM control module [not shown] for detecting reflected or emitted light generated from the patient scalp or hair [not shown]. Further, a magnifying digital imager [not shown] can be incorporated into device 3905 to be in communication with a PMB control [not shown] to generate images of the patient scalp during a treatment. Such imaging information can be useful for remote improving treatment compliance, and remote monitoring of scalp conditions, as well as dosage and response optimization.

Figure 40A:
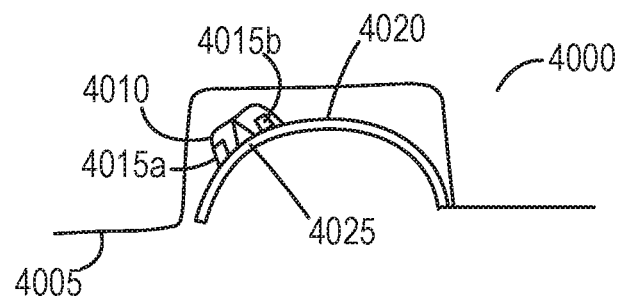
FIGS. 40A-40C illustrate a configuration for a light guide arrangement for a scalp area LLLT treatment device.
Figure 40B:
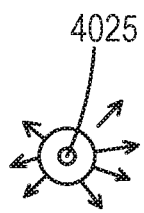
Figure 40C:
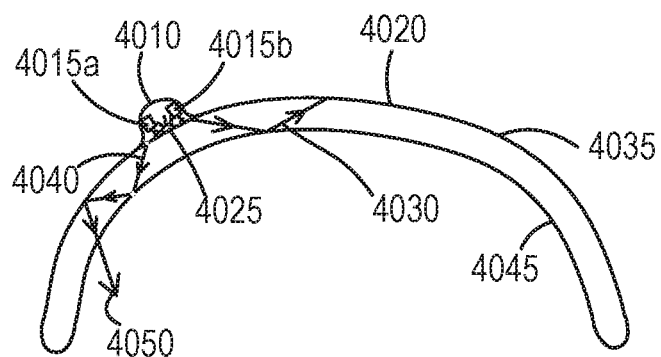

FIG. 40 illustrates a further implementation of the present invention suitable for hair growth or similar treatments. Referring to FIGS. 40*a* and 40*c*, scalp area treatment device 4000 configured to fit within a hat 4005 as illustrated. PBM control module 4010 is configured with at least one light source, shown here as laser diodes 4015*a* and 4015*b*, can also comprise two or more, or three or more, or four or more, or five or more, or seven or more diodes, LEDs or SLDs. Light sources 4015*a* and 4015*b* are shown operationally and optically engaged with light guide arrangement 4020 with mirror 4025 suitably configured to optically transmit light from 4015*a* and 4015*b* into and from light guide arrangement 4020 to a scalp area [not shown] in use. In this regard, mirror 4025 is shown as cone shaped in FIG. 40*a*, where such shape has been found to enhance light delivery from light guide arrangement 4020. Light guide arrangement 4020 is made from material that is light transmissive from treatment side 4045 (FIG. 40*c*), substantially flexible and suitably shaped to conform to areas proximal to the top of a patient's head [not shown] so as to allow LLLT treatment to be delivered from treatment side 4045.

Referring to FIGS. 40*b* and 40*c*, for purpose of illustration, light guide arrangement 4020, is optically engaged to mirror 4025. Mirror 4025 is configured to receive light emitted from at least one light source, here shown as 4015*a* and 4015*b*. When a light beam such as shown by 4030, which is generated from at least one light source 4015*a* and 4015*b* at the instruction of PBM control module 4010 and is transmitted within light guide arrangement 4020, reaches interior light guide arrangement surface 4035 at a greater angle of incidence than the critical angle, light beam 4030 will be reflected back into light guide arrangement 4020 to for further travel therein. When a light beam such as 4040 reaches treatment side 4045 at an angle less than the critical angle, or at a designated scattering area, it will travel through light guide arrangement surface 4050, to reach the scalp so as to deliver therapeutic LLLT treatment to a patient in need thereof. In another example, interior light guide arrangement surface 4035 can be coated with reflective material form designated scattering spots or areas configured to increase amount of light deliverable to light guide arrangement surface 4050 so as to increase the amount of light reaching the patient's scalp area.

Figure 41B:
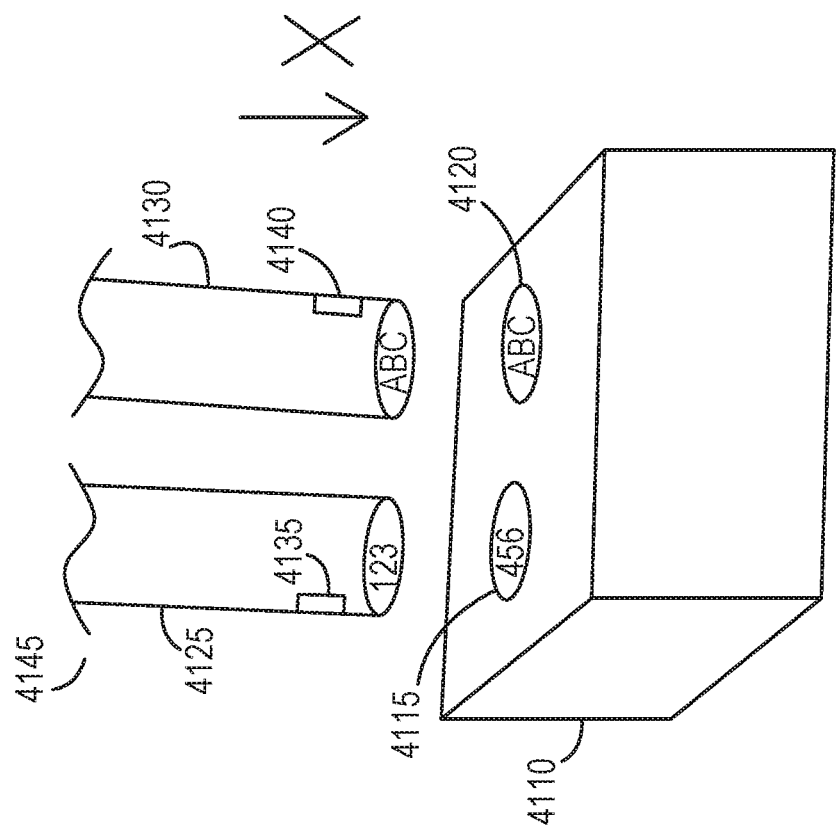
FIGS. 41A-41B show a framework for validation of light guide elements for engagement ports in the LLLT treatment control module.
Figure 41A:
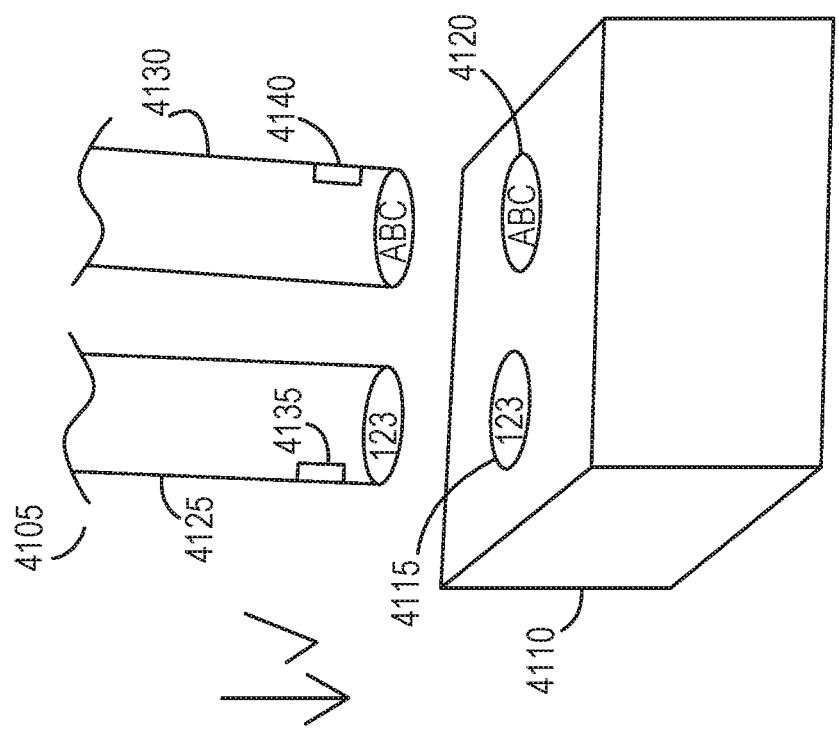

FIG. 41 illustrates a further implementation of the present invention comprising light guide arrangement validation functionality to confirm that a light guide arrangement is properly matched with an associated PBM control module and to generate any associated LLLT treatment dosage, deliver appropriate personalized treatment, activate monitoring sensors, log treatment history, and provide treatment instructions. FIG. 41*a* shows a simplified light guide/module diagram 4105 with PBM control module 4110 having engagement ports 4115 and 4120. Engagement ports 4115 and 4120 are configurable to recognize and validate only light guide elements, here shown as 4125 and 4130, that are properly configured for engagement with PBM control module 4110. In this regard, light guide elements 4125 and 4130 each, independently, comprise validation signaling capability 4135 and 4140 that is readable by componentry [not shown] associated with PBM control module 4010. Such validation signaling capability 4135 and 4130 can comprise RFID, bar code scanning, holographic scanning, physical patterns, mechanical patterns, defraction gratings, QR codes, color coding, direct connection circuits (e.g., wires directly connected between the machine and a small chip on the mold), physical (such as physical teeth and groves as a key on a light guide) etc. In one implementation, instructions associated with PBM control module 4010 can require that a signal provided by 4135 and 4140 match an expected signal defined by the software instructions, for example. If the signal matches, and when 4125 and 4130 are inserted into engagement ports 4115 and 4120, PBM control module 4110 will be configurable to activate the componentry therein, so as to generate operational and optical engagement between PBM control module 4110 and light guide elements 4125 and 4130 so as to allow LLLT treatment to be delivered to a patient [not shown] who is wearing a LLLT treatment device [not shown] having 4105 associated therewith. In contrast, 4145 shows an implementation where validation does not occur and, therefore, LLLT treatment is not delivered to a patient [not shown] who is wearing a LLLT treatment device [not shown] associated with 4145. In this regard, software instructions associated with PBM control module 4110 have configured engagement ports 4115 and 4120 to expect a first signal 456 from light guide element 4125 and a second signal XYZ from light guide element 4130. However, first light guide signal componentry 4135 is generating signal 123 and second light guide signaling componentry 4140 is generating signal ABC. When light guide elements 4125 and 4130 are engaged with engagement ports 4115 and 4120, the signal mismatch will be recognized by PBM control module 4110, and 4110 will not activate to generate operational and optical engagement with light guide elements 4125 and 4130. In other words, the LLLT delivery device will not function with such a signal mismatch. While each of light guide elements 4125 and 4130 are shown having signaling capability, in some implementations, at least one light guide element end is validatable with a corresponding engagement port in an associable PBM control module.

As would be recognized, such validation capability can better ensure that desired LLLT treatment is delivered at a predetermined dosage to a patient only when a defined/ prescribed amount of LLLT treatment is matched to a specific patient. Moreover, such matching can better ensure that treatment effectiveness and patient compliance can be monitored. PBM control modules can also be used with multiple LLLT delivery elements, whereby software instructions provided to a PBM control module can be automatically and intelligently configured for different LLLT delivery elements and/or light guide arrangements.

Figure 42:
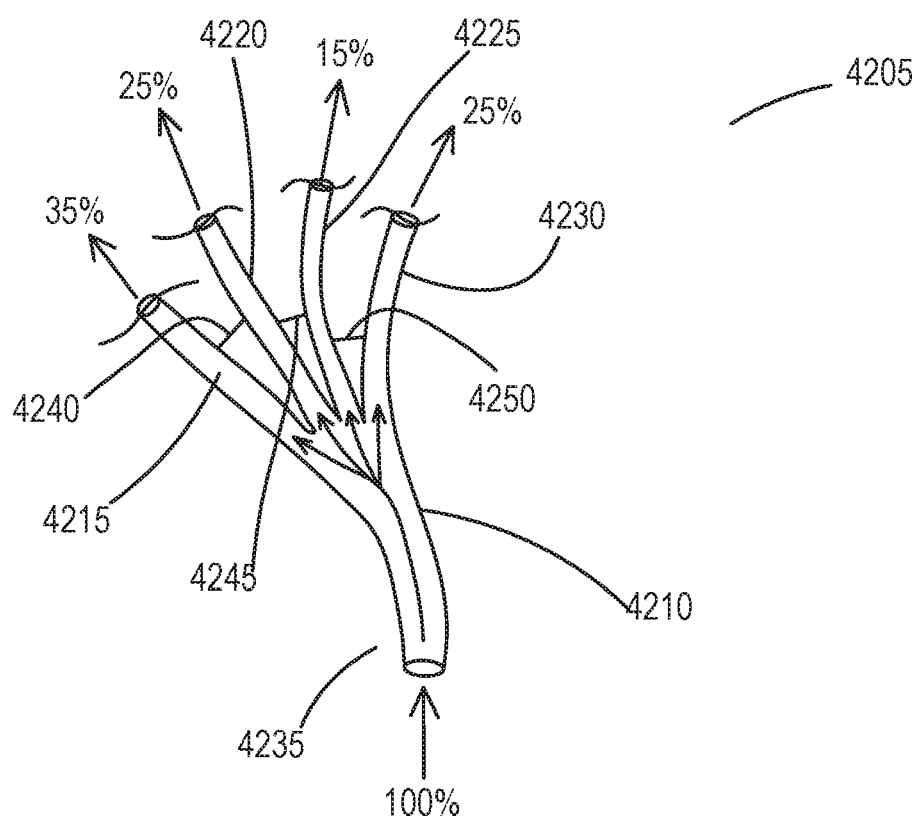
FIG. 42 illustrates a light guide element configuration suitable for some implementations of the present invention.

FIG. 42 illustrates a light guide arrangement 4205 configured to allow light provided from a PBM control module [not shown] by way of single light guide engagement stem 4210 to be delivered to a LLLT delivery element [not shown] by way of a plurality of light guide stems, such as with 4215, 4220, 4225, and 4230 that branch from stem 4210. As shown, light enters light guide stem end 4235 by way of operational and optical engagement with a PBM control module [not shown] at an 100% energy level as delivered from one or more light sources [not shown] associated therewith. A partial amount of this light energy is delivered to each of light guide stems 4215, 4220, 4225, and 4230 and travels along the lengths of each for delivery to a patient [not shown] via an associated LLLT delivery element [not shown]. As shown light energy delivered to 4215, 4220, 4225, and 4230 is at 35%, 25%, 15%, and 25%, respectively, as measured by the original 100% light energy delivered from the PBM control module [not shown] at stem end 4235 when end 4235 is operationally and optically engaged therewith. The amount of energy delivered to each of 4215, 4220, 4225, and 4230 can be modified by changing the angle of separation and/or the distances between each of 4215, 4220, 4225, and 4230 as shown, for example, by 4240, 4245 and 4250. The amount of light energy delivered into each of stem 4215, 4220, 4225, and 4230 and, therefore, to the patient [not shown] can also be modified by variation in one or more cross-sectional areas thereof, application of and/or variations in reflective coatings thereto, creating variations in attenuation, and application of light scattering characteristics thereto, such as by adding discontinuities to the interiors or surfaces as discussed elsewhere herein. More or fewer stems can also be generated, which will affect the amount of light transmitted through each stem, as would be recognized from FIG. 42.

Figure 43:
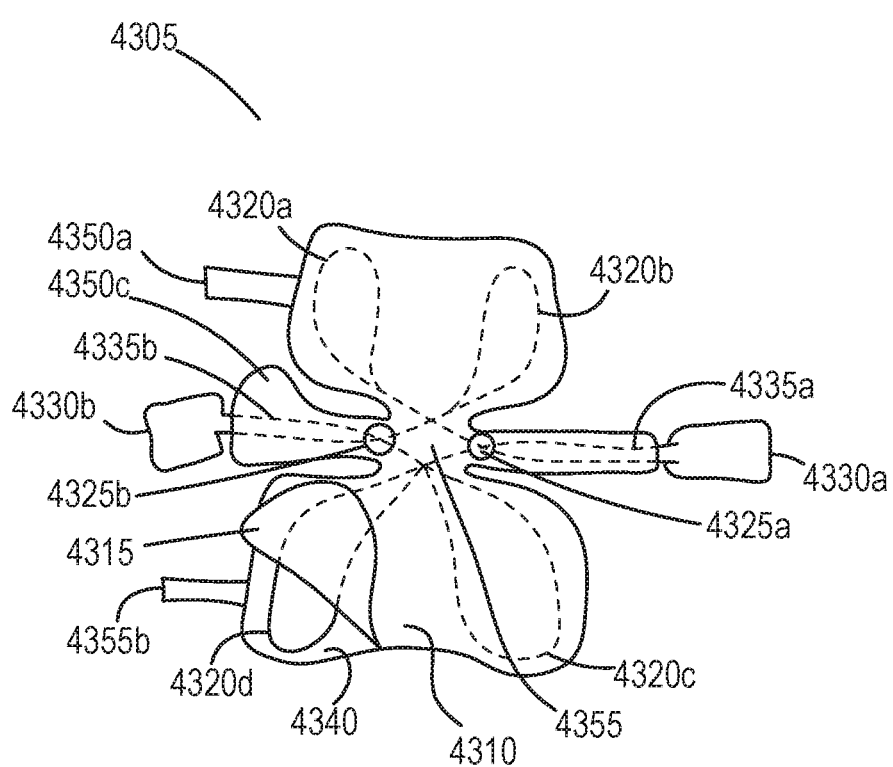
FIG. 43 illustrates a LLLT treatment device suitable for a knee or leg area.

FIG. 43 illustrates a LLLT treatment device for postoperative care after a surgery of the leg, such as a total knee arthroplasty, or TKA. Device 4305 comprises a patient facing side 4310, comprising a transparent or translucent first cover material 4315 beneath which four light guide elements 4320*a*, 4320*b*, 4320*c*, and 4320*d* are configurable. Each of 4320*a* and 4320*d* are operationally and optically engageable with each other at connection 4325*a* and further in operational and optical engagement with PBM control module 4330*a* via light guide element 4335*a*. Each of 4320*b* and 4320*c* are operationally and optically engageable with each other at connection 4325*b* and further in operational and optical engagement with PBM control module 4330*b* via light guide element 4335*b*. First cover material 4315 comprises patient facing side 4310 is a transparent or translucent material comprising light transmissive fibers suitable to engage with light guides for light scattering and contact with the skin of the patient to allow LLLT to be delivered to the patient's leg and knee areas [not shown] and associated "healing vital areas" [not shown], as discussed previously. Second cover material 4340 can comprise a fabric material or the like. On an outer surface 4345 [not shown] of device 4305, fasteners 4350*a*, 4350*b*, and 4350*c* can be configured in the form of, for example, Velcro®, elastic straps, clips, hooks etc. When device 4305 is secured to a patient's knee area, patient knee area [not shown] is proximal to incision light delivery area 4355, whereby the patient's incision [not shown] will be treated with LLLT delivered by light guide elements 4335*a* and 4335*b*, while the rest of the leg will be treated with LLLT delivered by light guide elements 4320*a*, 4320*b*, 4320*c*, and 4320*d*. In use, PBM control modules 4330*a* and 4330*b* can be removably or permanently mountable to device 4305 and configured to fit comfortably proximal to back of patient's leg [not shown] or the like. More or fewer light guide elements and/or PBM control modules can suitably be used.

Figure 44A:
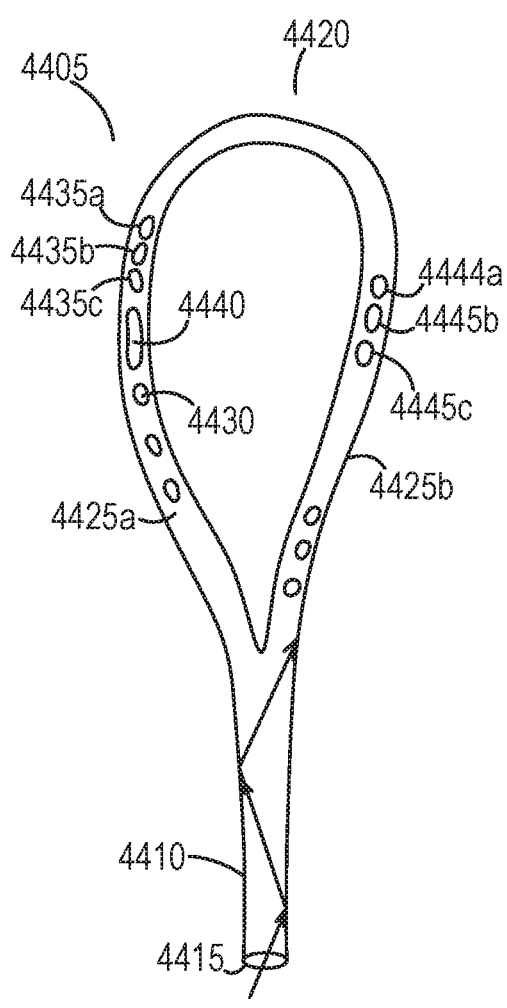
FIGS. 44A-44C illustrate a light guide element configuration suitable for some implementations of the present invention.
Figure 44B:
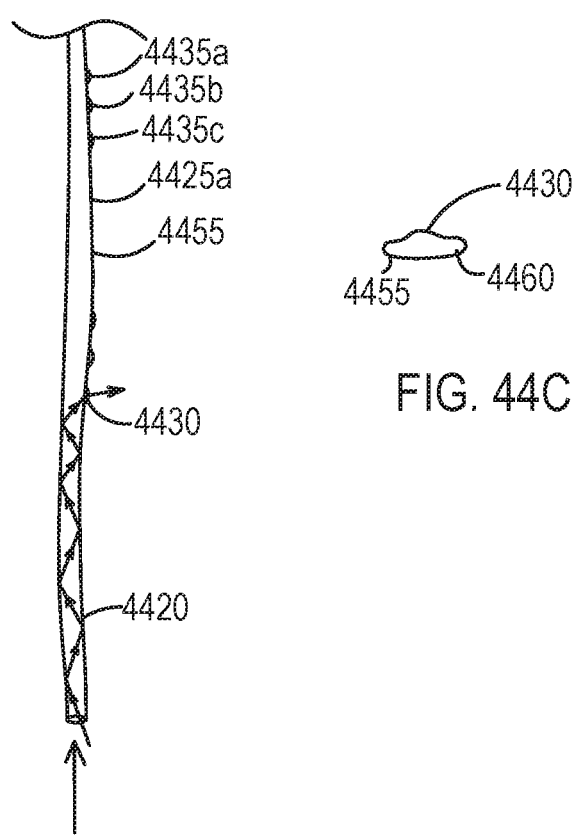
Figure 44C:
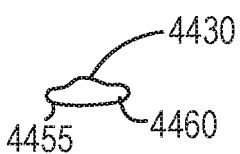

FIGS. 44*a*, 44*b*, and 44*c* show an exemplary configuration of a light guide element 4405 that can be used in the LLLT treatment device illustrated in FIG. 43. Front, side, and cross-sectional views, respectively, are provided for illustration in FIGS. 44*a*, 44*b*, and 44*c*. Referring to FIG. 44*a*, light guide element 4405 has first section 4410 having end 4415. Light guide element 4405 is further configured in the shape of a loop at a second end 4420. Looped second end 4420 has sides 4425*a* and 4425*b* that comprise, for example, light delivery scattering areas 4430, 4435*a*, 4435*b*, 4435*c*, 4440, 4445*a*, 4445*b*, and 4445*c*, as well as others. A wide variety of variations in the placement and configuration of the light delivery scattering areas can be generated in light guide elements depending on the needs of the patient being treated and the design of a LLLT treatment appropriate for the patient. For example, groupings of light delivery scattering areas can be provided in various locations on a patient on each of loop sides 4425*a* and 4425*b*, as shown with 4435*a*, *b* and *c* and 4445*a*, *b*, and *c*, respectively. Smaller or larger light delivery scatterings can be provided as shown with 4430 and 4440, respectively. In use, end 4415 is operationally and optically engaged with a PBM control module, as discussed elsewhere herein. In one aspect, the loop section of light guide element 4405 can be configured from light transmissive material having lower durometers, for example, Shore A hardness of about 30 to enhance patient comfort and functionality, which the section near end 4415 can be configured from light transmissive material having lower durometers, for example Shore A hardness of about 90 to enhance connectablity of end 4415 with a PBM control module. Such multi-hardness light guide design is contemplated for other sizes and shapes of light guide arrangement. In this regard, a light guide or light guide arrangement can be configured with two or more Shore A hardness ratings, where a higher Shore A hardness is present at or near a connection end thereof.

As shown by the side view of 4405 in FIG. 44*b*, light guide element side view 4420 has a low height profile as compared to the width. For example, the height can be from about 1 mm to about 3 mm and the width from about 5 to about 12 mm. The delivery scattering areas can also be suitably raised from surface 4455 of loop side 4425*a*, for example. FIG. 44*c* further illustrates this raised profile with light delivery opening 4430. In use, LLLT treatment will be delivered from a PBM control module [not shown] into end 4415 to travel through 4410 and into 4420*a* and 4420*b*. When the LLLT reaches a light delivery scattering area, such as 4430, the light will exit light guide element 4405 to provide LLLT treatment to a portion of the patient's body area being treated. A lower height to width ratio improves the comfort and safety to the patient in use, and also operates to reduce the occurrence of pressure injuries to the skin. In addition, a reflective coating [not shown] can be present on all or part of outer surface 4460 of light guide element 4405 to enhance light transmission through and out of the various light delivery openings.

Figure 45A:
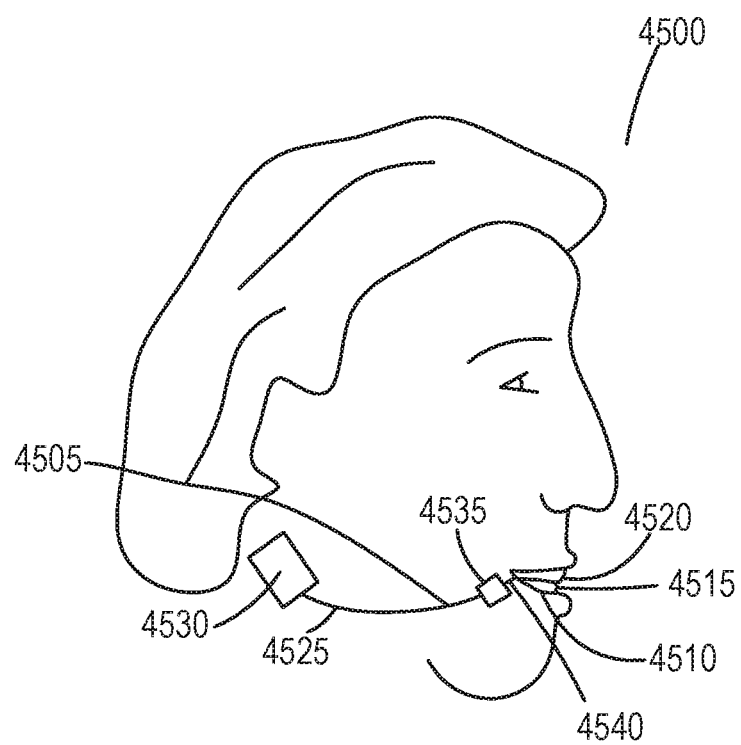
FIGS. 45A-45C illustrate a mouth area LLLT treatment device.

Referring to FIG. 45, wearable LLLT devices for treatment on the teeth in conjunction with procedures such as tonsillectomy, orthodontia, dental implants, bone grafting, gingival flap and other mouth area procedures are illustrated. As shown in FIG. 45*a*, patient 4500 is shown with device 4505 positioned in mouth 4510 and having lower mouthpiece 4515 and upper mouthpiece 4520. First light transmission portion 4525, which can be a fiber optic or other suitable light conveyance material, is in operational and optical engagement with PBM control module 4530. First light transmission portion 4525 is operationally and optically engaged at connection 4535 to second light transmission portion 4540 with second light transmission portion 4540 being suitably operationally and optically engaged and detachably attached to a rim [not shown] of either or both of lower and upper mouthpieces 4515 and 4520 so the such second light transmission portion 4540 can substantially move as one piece when the mouth opens and closes without 4520 dangling from mouthpieces 4515 and 4520. Connection 4535 can comprise a magnetic connection, as discussed previously. Lower mouthpiece 4515 is configurable to fit over or be positioned proximally to the lower teeth (if present) [not shown] and gums [not shown] of mouth 4510 to deliver LLLT treatment to one or more of patient gums, teeth, gums, lower surface of tongue etc. Upper mouthpiece 4520 is configurable to fit over, or to be positioned proximally to the upper teeth [not shown] or be positioned proximally to the upper teeth (if present) [not shown], gums [not shown], and/or palate [not shown]. To enable LLLT treatment to be delivered from mouthpieces 4515 and 4520, each are independently, made from optically transmissive material with hardness in the range of Shore A Hardness of about 20 to about 95. Mouthpieces 4515 and 4520 can be suitably used together to provide treatment to an upper and lower portion of patient mouth 4510. In this regard, each of 4515 and 4520 can be operationally and optically engaged with PBM control module 4530, such as by providing two light transmission portion engagement ports [not shown] or by configuring an additional PBM control module [not shown] to engage with 4515 or 4520, as appropriate.

Figure 45B:
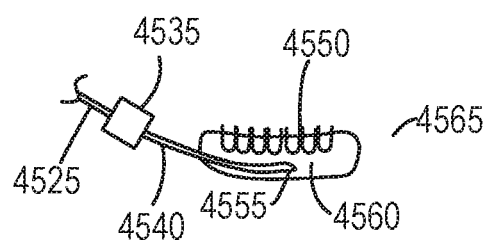

Either of lower and upper mouthpieces 4515 and 4520 can be configured with grooves 4550 on a tooth facing side, as shown on FIG. 45*b*. Further in relation to FIG. 45*b*, second light transmission portion end 4555 is in operational and optical engagement with the interior 4560 of mouthpiece 4565. Mouthpiece 4565 can be fabricated from a softer material, for example, from Shore D hardness of about 20 to about 80 so as to facilitate one form of placement of 4565 of on patient teeth [not shown] via grooves 4550. On the other hand, harder materials, such as those in the Shore D hardness range of about 70 to about 95 can be more suitable for clear and less visible braces, which are designed to have groove(s) 4550 that fit tightly to the teeth for orthodontal alignments. Although only one mouthpiece 4565 is illustrated for placement of grooves 4550, two of the mouth pieces, each engaged with a dosed light source, can be designed and used simultaneously for both the upper and lower teeth for LLLT treatment.

Figure 45C:
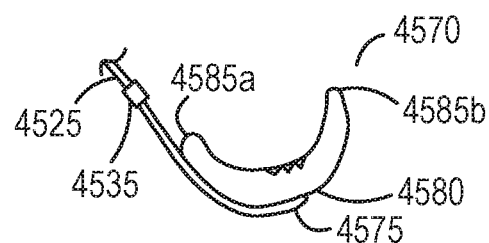

FIG. 45*c* illustrates mouthpiece 4570 wherein second light transmission portion 4575 can be configured on an outer surface of 4570, and is in operational and optical engagement with PBM control module 4530 [not shown] so as to deliver LLLT treatment into an interior of 4570 to be delivered to mouth areas [not shown] proximal thereto. At least some of the interior [not shown] of either or both of mouthpieces 4565 and 4570 can comprise a reflective coating enhance LLLT transmission therefrom. As discussed previously, reflective materials or discontinuities can be incorporated on or in the mouthpiece configurations to further enhance light transmission therefrom.

LLLT mouth device configurations can be optimized to treat various conditions. For example, when an entire mouthpiece surface is configured to transmit light delivered from a PBM control module, the mouthpiece can function as clear braces to enhance correction of the teeth position. Upper and lower mouthpieces can be configured to allow light to be delivered from a single PBM control module. When red light is applied to the mouth interior at from about 640 nm to about 670 nm dosed at about 0.2 to about 1 J/cm²/day, LLLT treatment can speed up teeth movement as well as reduce the pain and discomfort from wearing braces. For another example, when ends 4585*a* and 4585*b* of mouth piece 4570 comprise discontinuity or scattering areas while the rest of surface 4580 is opaque, delivery of red light at from about 640 nm to about 670 nm dosed at from about 0.5 to about 1.5 J/cm²/day, can reduce the pain and swelling after surgeries to the uvula, tonsils and palate. For a third example, when the side 4560 of mouthpiece 4565 comprises discontinuity or scattering areas while the rest of the surfaces are opaque, by delivering red light at from about 640 nm to about 670 nm dosed at about 0.2 to about 0.8 J/cm²/day, LLLT can reduce the pain and swelling after surgeries to the gum, or as ongoing treatment to gingivitis.

Table 2 below provides general parameters for a LLLT treatment device of the present invention.

TABLE 2

| Battery Power | | |
| --- | --- | --- |
| Charging time hour | 4 | H |
| Battery Capacity | 2 | AH |
| Avg Battery Voltage | 5 | V |
| Battery Power | 36000 | J |
| Avg Laser Power | 120 | mW |
| Delivered Energy to Patient | 311.04 | J |
| Avg Energy Density | 1.5552 | J/cm² |

EXAMPLES

The following examples illustrate various aspects of the disclosure. It will be apparent to those skilled in the art that many modifications, both to materials and methods, may be practiced without departing from the scope of the disclosure.

Example 1

Dentalveolar Surgery—Third Molar Extraction

Eight patients having impacted third molars were treated with LLLT treatment delivered proximal to the point of extraction with an inventive mouth area treatment device as described further herein. The LLLT treatment protocol was application of light at 650 nm and 880 nm delivered at 160 mW over an 120 cm² area adjacent to the extraction site of each patient. Each patient was subjected to daily LLLT treatment, 3 times each day, with 28 minutes of light exposure each treatment.

Results: Treated patients had no observable swelling at post-operative 72 hours. Patients reported less pain than average patients without LLLT treatment in the opinions of the attending clinicians.

Example 2

Abdominoplasty

Two patients with abdominoplasty were subjected to LLLT at wavelengths of 650 nm delivered at 160 mW over an area of 300 cm² with an inventive abdominal area treatment device as described further herein. Patients were exposed to these wavelength 3 times a day with 32 minutes light exposure each treatment period.

Results: Treated patients had minimum bruising at postoperative 96 hours. Patients reported less pain than average patients without LLLT in the opinions of the attending clinicians.

Example 3

Cesarean Section

Two patients with Cesarean deliveries were treated with LLLT post-delivery at a wavelength of 650 nm delivered over an area of 160 mW over an area proximal to the Cesarean delivery incision with an inventive pelvic area treatment device as described further herein. Patients were exposed to LLLT treatment 3 times per day, with 36 minutes light exposure for each treatment.

Results: Treated patients had minimal bruising at post-operative day 7. Reported significantly less pain than average patients without LLLT treatment in the opinions of the attending clinicians.

Example 4

Total Knee Arthroplasty (TKA)

One patient with a TKA incision was treated with LLLT treatment post-surgery at 650 nm and 810 nm delivered at 320 mW over an area of 560 cm$^2$ proximal to the incision area with an inventive knee and leg area treatment device as described further herein. Daily LLLT treatments were given to the patient 3 times each day, with 40 minutes light exposure each treatment.

Results: The treated patient had a minimum of bruising and started walking unassisted since at post-operative day 3. Patient reached a range of motion of 0-120 degrees by post-operative day 28. Patient reported significantly less pain than expected in the opinion of the attending clinicians.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A method of generating information about scalp hair amounts in a plurality of persons comprising:
   providing a device comprising:
   a) a cap configured in a shape of a human scalp, wherein the cap comprises:
   (1) a control module comprising:
      (a) a microprocessor;
      (b) a battery power source;
      (c) a memory comprising a set of instructions which upon execution by the microprocessor operates the control module;
      (d) a communications circuitry configured to communicate with an external device;
      (e) a housing encasing the microprocessor, the battery power source, the memory, and the communications circuitry; and
   (2) at least one light source configured on a scalp facing cap side, wherein the at least one light source operably coupled to the control module, the at least one light source configured to generate light in a predetermined spectrum for light therapy;
   wherein the cap further comprises:
      a light guide for delivering the light to a scalp area, the light guide comprises:
         at least one conduit curved to a substantially U shape, the at least one conduit has a first end and an opposite second end, and
         a branch tube that has a bifurcated end and an opposite third end, wherein the bifurcated end of the branch tube is continuous with the at least one conduit such that the branch tube is in optical communication with the at least one conduit,
      wherein a first laser source of the at least one light source is coupled to the first end of the at least one conduit, a second laser source of the at least one light source coupled to the second end of the at least one conduit, and a third laser source of the at least one light source coupled to the third end of the branch tube.

* * * * *